(12) United States Patent
Ptacin et al.

(10) Patent No.: US 12,318,431 B2
(45) Date of Patent: Jun. 3, 2025

(54) CYTOKINE CONJUGATES FOR THE TREATMENT OF PROLIFERATIVE AND INFECTIOUS DISEASES

(71) Applicant: Synthorx, Inc., La Jolla, CA (US)

(72) Inventors: Jerod Ptacin, San Diego, CA (US); Carolina E. Caffaro, San Diego, CA (US); Marcos Milla, Carlsbad, CA (US)

(73) Assignee: SYNTHORX, INC., Bridgewater, NJ (US)

( * ) Notice: Subject to any disclaimer, the term of this patent is extended or adjusted under 35 U.S.C. 154(b) by 0 days.

(21) Appl. No.: 18/327,535

(22) Filed: Jun. 1, 2023

(65) Prior Publication Data

US 2024/0082359 A1    Mar. 14, 2024

Related U.S. Application Data

(60) Continuation of application No. 16/803,816, filed on Feb. 27, 2020, now Pat. No. 11,701,407, which is a division of application No. 16/434,999, filed on Jun. 7, 2019, now Pat. No. 10,610,571, which is a continuation of application No. PCT/US2018/045257, filed on Aug. 3, 2018.

(60) Provisional application No. 62/540,781, filed on Aug. 3, 2017.

(51) Int. Cl.
| | | |
|---|---|---|
| A61K 38/00 | (2006.01) | |
| A61K 38/20 | (2006.01) | |
| A61K 47/54 | (2017.01) | |
| A61K 47/60 | (2017.01) | |
| A61K 47/61 | (2017.01) | |
| A61K 47/64 | (2017.01) | |
| A61K 47/65 | (2017.01) | |
| A61K 47/68 | (2017.01) | |
| C07K 14/55 | (2006.01) | |
| C07K 14/715 | (2006.01) | |

(52) U.S. Cl.
CPC ........ *A61K 38/2013* (2013.01); *A61K 47/542* (2017.08); *A61K 47/60* (2017.08); *A61K 47/61* (2017.08); *A61K 47/643* (2017.08); *A61K 47/644* (2017.08); *A61K 47/65* (2017.08); *A61K 47/68* (2017.08); *C07K 14/55* (2013.01); *C07K 14/7155* (2013.01); *A61K 38/00* (2013.01)

(58) Field of Classification Search
CPC .. A61K 38/2013; A61K 47/542; A61K 47/60; A61K 47/6813; C07K 14/55; C07K 14/7155
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,667,025 A | 5/1987 | Miyoshi et al. |
| 4,683,195 A | 7/1987 | Mullis et al. |
| 4,683,202 A | 7/1987 | Mullis et al. |
| 4,762,779 A | 8/1988 | Snitman |
| 4,766,106 A | 8/1988 | Katre et al. |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,849,513 A | 7/1989 | Smith et al. |
| 4,851,512 A | 7/1989 | Miyaji et al. |
| 4,876,335 A | 10/1989 | Yamane et al. |
| 4,902,502 A | 2/1990 | Nitecki et al. |
| 4,904,582 A | 2/1990 | Tullis |
| 4,910,300 A | 3/1990 | Urdea et al. |
| 4,931,544 A | 6/1990 | Katre et al. |
| 4,948,882 A | 8/1990 | Ruth |
| 4,958,013 A | 9/1990 | Letsinger |
| 4,965,188 A | 10/1990 | Mullis et al. |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,089,261 A | 2/1992 | Nitecki et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |

(Continued)

FOREIGN PATENT DOCUMENTS

| | | |
|---|---|---|
| CN | 102665754 A | 9/2012 |
| CN | 104231068 A | 12/2014 |

(Continued)

OTHER PUBLICATIONS

Jiang et al. Role of IL-2 in cancer immunotherapy. Oncoimmunology 5(6):e1163462 (2016).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).

(Continued)

*Primary Examiner* — Jeanette M Lieb
(74) *Attorney, Agent, or Firm* — McNeill PLLC

(57) ABSTRACT

Disclosed herein are interleukin (IL) conjugates (e.g., IL-2 conjugates) and use in the treatment of one or more indications. Also described herein are pharmaceutical compositions and kits comprising one or more of the interleukin conjugates (e.g., IL-2 conjugates).

21 Claims, 21 Drawing Sheets

Specification includes a Sequence Listing.

(56) References Cited

U.S. PATENT DOCUMENTS

| | | |
|---|---|---|
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,206,344 A | 4/1993 | Katre et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,229,109 A | 7/1993 | Grimm et al. |
| 5,232,841 A | 8/1993 | Hashimoto et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,268,273 A | 12/1993 | Buckholz |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,370,995 A | 12/1994 | Hennecke et al. |
| 5,371,241 A | 12/1994 | Brush |
| 5,389,529 A | 2/1995 | Panayotatos et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,719 A | 11/1995 | Meng et al. |
| 5,470,967 A | 11/1995 | Huie et al. |
| 5,476,925 A | 12/1995 | Etsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,899 A | 1/1997 | Sato et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,612,199 A | 3/1997 | Western et al. |
| 5,614,185 A | 3/1997 | Koths et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,643,564 A | 7/1997 | Hamaguchi et al. |
| 5,645,985 A | 7/1997 | Froehler et al. |
| 5,646,265 A | 7/1997 | McGee |
| 5,648,247 A | 7/1997 | Picataggio et al. |
| 5,656,493 A | 8/1997 | Mullis et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,712,114 A | 1/1998 | Mankovich et al. |
| 5,714,331 A | 2/1998 | Buchardt et al. |
| 5,719,262 A | 2/1998 | Buchardt et al. |
| 5,747,646 A | 5/1998 | Hakimi et al. |
| 5,750,692 A | 5/1998 | Cook et al. |
| 5,763,588 A | 6/1998 | Matteucci et al. |
| 5,830,653 A | 11/1998 | Froehler et al. |
| 5,834,594 A | 11/1998 | Hakimi et al. |
| 5,846,818 A | 12/1998 | Robinson et al. |
| 5,888,732 A | 3/1999 | Hartley et al. |
| 5,932,474 A | 8/1999 | Tsien et al. |
| 6,005,096 A | 12/1999 | Matteucci et al. |
| 6,008,378 A | 12/1999 | Tsien et al. |
| 6,010,871 A | 1/2000 | Takahara et al. |
| 6,013,526 A | 1/2000 | Takahara et al. |
| 6,054,271 A | 4/2000 | Tsien et al. |
| 6,124,090 A | 9/2000 | Rose et al. |
| 6,143,557 A | 11/2000 | Hartley et al. |
| 6,171,861 B1 | 1/2001 | Hartley et al. |
| 6,261,797 B1 | 7/2001 | Sorge et al. |
| 6,268,490 B1 | 7/2001 | Imanishi et al. |
| 6,270,969 B1 | 8/2001 | Hartley et al. |
| 6,277,608 B1 | 8/2001 | Hartley et al. |
| 6,288,302 B1 | 9/2001 | Yu et al. |
| 6,294,323 B1 | 9/2001 | Ullman et al. |
| 6,365,375 B1 | 4/2002 | Dietmaier et al. |

(56) References Cited

U.S. PATENT DOCUMENTS

| | | |
|---|---|---|
| 6,391,544 B1 | 5/2002 | Salituro et al. |
| 6,451,569 B1 | 9/2002 | Tsien et al. |
| 6,525,191 B1 | 2/2003 | Ramasamy |
| 6,670,461 B1 | 12/2003 | Wengel et al. |
| 6,720,140 B1 | 4/2004 | Hartley et al. |
| 6,770,748 B2 | 8/2004 | Imanishi et al. |
| 6,794,499 B2 | 9/2004 | Wengel et al. |
| 6,906,170 B1 | 6/2005 | Lider et al. |
| 6,955,807 B1 | 10/2005 | Shanafelt et al. |
| 7,034,133 B2 | 4/2006 | Wengel et al. |
| 7,045,337 B2 | 5/2006 | Schultz et al. |
| 7,053,207 B2 | 5/2006 | Wengel |
| 7,105,653 B2 | 9/2006 | Shanafelt et al. |
| 7,393,632 B2 | 7/2008 | Cheo et al. |
| 7,399,845 B2 | 7/2008 | Seth et al. |
| 7,427,672 B2 | 9/2008 | Imanishi et al. |
| 7,625,717 B2 | 12/2009 | Chin et al. |
| 7,670,823 B1 | 3/2010 | Hartley et al. |
| 7,741,457 B2 | 6/2010 | Seth et al. |
| 7,744,861 B2 | 6/2010 | Zhao et al. |
| 7,803,777 B2 | 9/2010 | DeFrees |
| 8,012,465 B2 | 9/2011 | Elias et al. |
| 8,252,743 B2 | 8/2012 | Guyon et al. |
| 8,273,833 B2 | 9/2012 | Bentley et al. |
| 8,420,792 B2 | 4/2013 | Tian et al. |
| 8,501,805 B2 | 8/2013 | Seth et al. |
| 8,546,556 B2 | 10/2013 | Seth et al. |
| 8,557,776 B2 | 10/2013 | Lehmann et al. |
| 8,609,383 B2 | 12/2013 | Young et al. |
| 9,089,614 B2 | 7/2015 | Lin et al. |
| 9,682,934 B2 | 6/2017 | Stafford et al. |
| 9,732,134 B2 | 8/2017 | Gavin et al. |
| 9,840,493 B2 | 12/2017 | Yang et al. |
| 9,861,705 B2 | 1/2018 | Bossard et al. |
| 9,938,516 B2 | 4/2018 | Zimmerman et al. |
| 9,988,619 B2 | 6/2018 | Zimmerman et al. |
| 10,610,571 B2 | 4/2020 | Ptacin et al. |
| 10,851,144 B2 | 12/2020 | Butz et al. |
| 10,960,079 B2 | 3/2021 | Bossard et al. |
| 11,077,195 B2 | 8/2021 | Ptacin et al. |
| 11,622,993 B2 | 4/2023 | Ptacin et al. |
| 11,701,407 B2 | 7/2023 | Ptacin et al. |
| 2002/0001804 A1 | 1/2002 | Mitchell et al. |
| 2002/0007051 A1 | 1/2002 | Cheo et al. |
| 2003/0083373 A1 | 5/2003 | Tsien et al. |
| 2004/0171570 A1 | 9/2004 | Allerson et al. |
| 2005/0112590 A1 | 5/2005 | Boom et al. |
| 2005/0118623 A1 | 6/2005 | Belousov et al. |
| 2005/0130923 A1 | 6/2005 | Bhat et al. |
| 2006/0035254 A1 | 2/2006 | Manoharan et al. |
| 2006/0074035 A1 | 4/2006 | Hong et al. |
| 2006/0084136 A1 | 4/2006 | Kudlicki et al. |
| 2006/0160187 A1 | 7/2006 | Denis-Mize et al. |
| 2006/0234205 A1 | 10/2006 | Cao et al. |
| 2006/0263771 A1 | 11/2006 | Hirao et al. |
| 2007/0287831 A1 | 12/2007 | Seth et al. |
| 2008/0025947 A1 | 1/2008 | Gillies et al. |
| 2008/0039618 A1 | 2/2008 | Allerson et al. |
| 2008/0300163 A1 | 12/2008 | Cho et al. |
| 2009/0155844 A1 | 6/2009 | Yokoyama et al. |
| 2010/0316595 A1 | 12/2010 | Elias et al. |
| 2010/0323364 A1 | 12/2010 | Sekine et al. |
| 2012/0022013 A1 | 1/2012 | Sinclair et al. |
| 2012/0077252 A1 | 3/2012 | Picataggio et al. |
| 2012/0244112 A1 | 9/2012 | Ast et al. |
| 2012/0315245 A1 | 12/2012 | Leon et al. |
| 2013/0333068 A1 | 12/2013 | Coffin |
| 2014/0046026 A1 | 2/2014 | Garcia et al. |
| 2014/0255345 A1 | 9/2014 | Grabstein et al. |
| 2014/0314864 A1 | 10/2014 | Cheng et al. |
| 2014/0315245 A1 | 10/2014 | Yam et al. |
| 2014/0328791 A1 | 11/2014 | Bossard et al. |
| 2016/0168187 A1 | 6/2016 | Romesberg et al. |
| 2017/0029829 A1 | 2/2017 | Romesberg et al. |
| 2017/0044229 A1 | 2/2017 | Garcia et al. |
| 2017/0260137 A1 | 9/2017 | Stafford et al. |
| 2017/0283469 A1 | 10/2017 | Thanos et al. |
| 2017/0313753 A1 | 11/2017 | Gavin et al. |
| 2017/0369871 A1 | 12/2017 | Ptacin et al. |
| 2018/0051065 A1 | 2/2018 | Yin |
| 2018/0086734 A1 | 3/2018 | Yang et al. |
| 2020/0181220 A1 | 6/2020 | Ptacin et al. |
| 2020/0188484 A1 | 6/2020 | Ptacin et al. |
| 2020/0231644 A1 | 7/2020 | Ptacin et al. |
| 2020/0299349 A1 | 9/2020 | Garcia et al. |
| 2020/0368293 A1 | 11/2020 | Olle |
| 2020/0399338 A1 | 12/2020 | Caffaro et al. |
| 2021/0023230 A1 | 1/2021 | Bossard et al. |
| 2021/0024602 A1 | 1/2021 | Sprogøe et al. |
| 2021/0046160 A1 | 2/2021 | Ptacin et al. |
| 2021/0054040 A1 | 2/2021 | Caffaro et al. |
| 2021/0060169 A1 | 3/2021 | Ikeda et al. |
| 2021/0070827 A1 | 3/2021 | Ptacin et al. |
| 2021/0139554 A1 | 5/2021 | Butz et al. |
| 2021/0196796 A1 | 7/2021 | Penaflor-Aspuria et al. |
| 2021/0221863 A1 | 7/2021 | Kang et al. |
| 2021/0299222 A1 | 9/2021 | Rodriguez et al. |
| 2021/0338829 A1 | 11/2021 | Caffaro et al. |
| 2022/0016249 A1 | 1/2022 | Ptacin et al. |
| 2022/0016252 A1 | 1/2022 | Abbadessa et al. |
| 2022/0273767 A1 | 9/2022 | Caffaro et al. |
| 2022/0324792 A1 | 10/2022 | Aerni et al. |
| 2023/0265148 A1 | 8/2023 | Hu et al. |
| 2023/0277627 A1 | 9/2023 | Caffaro et al. |
| 2023/0302089 A1 | 9/2023 | Caffaro et al. |
| 2023/0416327 A1 | 12/2023 | Caffaro et al. |

FOREIGN PATENT DOCUMENTS

| | | |
|---|---|---|
| EA | 025851 B1 | 2/2017 |
| EP | 0154316 A2 | 9/1985 |
| EP | 0614907 A1 | 9/1994 |
| EP | 0629633 A2 | 12/1994 |
| EP | 0811385 A2 | 12/1997 |
| EP | 2130835 A4 | 6/2010 |
| EP | 2581450 B1 | 8/2018 |
| EP | 2382228 B1 | 8/2020 |
| EP | 3280725 B1 | 8/2020 |
| EP | 4011388 A1 | 6/2022 |
| EP | 4209503 A1 | 7/2023 |
| JP | 861225199 A | 10/1986 |
| JP | 2007510401 A | 4/2007 |
| WO | 9213869 A1 | 8/1992 |
| WO | 9414226 A1 | 6/1994 |
| WO | 9422890 A1 | 10/1994 |
| WO | 9735869 A1 | 10/1997 |
| WO | 9914226 A2 | 3/1999 |
| WO | 9921013 A1 | 4/1999 |
| WO | 9962923 A2 | 12/1999 |
| WO | 0023456 A1 | 4/2000 |
| WO | 0074724 A2 | 12/2000 |
| WO | 0105801 A1 | 1/2001 |
| WO | 0132887 A1 | 5/2001 |
| WO | 0236626 A1 | 5/2002 |
| WO | 02062816 A1 | 8/2002 |
| WO | 02068216 A1 | 9/2002 |
| WO | 02070533 A2 | 9/2002 |
| WO | 03031464 A2 | 4/2003 |
| WO | 03055898 A1 | 7/2003 |
| WO | 03070918 A2 | 8/2003 |
| WO | 2004007713 A1 | 1/2004 |
| WO | 2004060300 A2 | 7/2004 |
| WO | 2004106356 A1 | 12/2004 |
| WO | 2005007121 A2 | 1/2005 |
| WO | 2005021570 A1 | 3/2005 |
| WO | 2005026187 A1 | 3/2005 |
| WO | 2005092928 A1 | 10/2005 |
| WO | 2005045015 A3 | 12/2005 |
| WO | 2004099231 A3 | 3/2006 |
| WO | 2006049297 A1 | 5/2006 |
| WO | 2006081510 A2 | 8/2006 |
| WO | 2006082184 A2 | 8/2006 |
| WO | 2007015557 A1 | 2/2007 |
| WO | 2007066737 A1 | 6/2007 |

(56) References Cited

FOREIGN PATENT DOCUMENTS

| | | |
|---|---|---|
| WO | 2007090071 A2 | 8/2007 |
| WO | 2007093599 A1 | 8/2007 |
| WO | 2007085485 A3 | 9/2007 |
| WO | 2007134181 A3 | 1/2008 |
| WO | 2008067825 A1 | 6/2008 |
| WO | 2008101157 A1 | 8/2008 |
| WO | 2008106186 A3 | 10/2008 |
| WO | 2008150729 A3 | 12/2008 |
| WO | 2008154401 A3 | 12/2008 |
| WO | 2009006478 A2 | 1/2009 |
| WO | 2009123216 A1 | 10/2009 |
| WO | 2009155102 A2 | 12/2009 |
| WO | 2010023670 A2 | 3/2010 |
| WO | 2010085495 A1 | 7/2010 |
| WO | 2011043385 A1 | 4/2011 |
| WO | 2011053065 A2 | 5/2011 |
| WO | 2011139699 A3 | 11/2011 |
| WO | 2012065086 A1 | 5/2012 |
| WO | 2012146628 A1 | 11/2012 |
| WO | 2015021432 A1 | 2/2015 |
| WO | 2015038426 A1 | 3/2015 |
| WO | 2015157555 | 10/2015 |
| WO | 2016025385 A1 | 2/2016 |
| WO | 2016115168 A1 | 7/2016 |
| WO | 2016164937 A3 | 1/2017 |
| WO | 2017106767 A1 | 6/2017 |
| WO | 2017112825 A2 | 6/2017 |
| WO | 2017223528 A1 | 12/2017 |
| WO | 2019014267 A1 | 1/2019 |
| WO | 2019028419 A1 | 2/2019 |
| WO | 2019028425 A1 | 2/2019 |
| WO | 2019165453 A1 | 8/2019 |
| WO | 2019173832 A2 | 9/2019 |
| WO | 2020020783 A1 | 1/2020 |
| WO | 2020056066 A1 | 3/2020 |
| WO | 2020097325 A1 | 5/2020 |
| WO | 2020146221 A1 | 7/2020 |
| WO | 2020163532 A1 | 8/2020 |
| WO | 2020201095 A1 | 10/2020 |
| WO | 2020219943 A1 | 10/2020 |
| WO | 2020252418 A2 | 12/2020 |
| WO | 2021030374 A1 | 2/2021 |
| WO | 2021030483 A1 | 2/2021 |
| WO | 2021030602 A1 | 2/2021 |
| WO | 2021030706 A1 | 2/2021 |
| WO | 2021041206 A1 | 3/2021 |
| WO | 2021050554 A1 | 3/2021 |
| WO | 2021091986 A1 | 5/2021 |
| WO | 2021093633 A1 | 5/2021 |
| WO | 2021133839 A1 | 7/2021 |
| WO | 2021140416 A2 | 7/2021 |
| WO | 2021263026 A1 | 12/2021 |
| WO | 2022076853 A1 | 4/2022 |
| WO | 2022076859 A1 | 4/2022 |
| WO | 2022174101 A1 | 8/2022 |
| WO | 2022256538 A1 | 12/2022 |
| WO | 2023122750 A1 | 6/2023 |
| WO | 2023137401 A1 | 7/2023 |

OTHER PUBLICATIONS

Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Juncosa-Ginesta et al. Improved efficiency in site-directed mutagenesis by PCR using a Pyrococcus sp. GB-D polymerase. Biotechniques 16:820-823 (1994).
Jung et al., Synthesis of phosphonate derivatives of uridine, cytidine, and cytosine arabinoside, Bioorg Med Chem, vol. 8, pp. 2501-2509, 2000.
Kabanov et al., A new class of antivirals: antisense oligonucleotides combined with a hydrophobic substituent effectively inhibit influenza virus reproduction and synthesis of virus-specific proteins in MOCK cells, FEBS Lett vol. 259, pp. 327-330, 1990.
Kandimalla et al., Effect of chemical modifications of cytosine and guanine in a CpG-motif of oligonucleotides: structure-immunostimulatory activity relationships, Bioorg. Med. Chem., vol. 9, pp. 807-813, 2001.
Kappler et al., Isozyme-specific enzyme inhibitors. 11. L-homocysteine-ATP S-C5' covalent adducts as inhibitors of rat methionine adenosyltransferases, J Med Chem, vol. 29, pp. 1030-1038, 1986.
Kappler et al., Species- or isozyme-specific enzyme inhibitors. 8. Synthesis of disubstituted two-substrate condensation products as inhibitors of rat adenylate kinases, J Med Chem, vol. 25, pp. 1179-1184, 1982.
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Kim et al. Stability and polymerase recognition of pyridine nucleobase analogues: role of minor-groove H-bond acceptors. Angew Chem Int Ed Engl 45(46):7809-12 (2006).
Kimoto et al. Generation of high-affinity DNA aptamers using an expanded genetic alphabet. Nat. Biotech. 31 (5):453-458 (2013).
Kivimae et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimae et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based Immunocytokines. Oncoimmunology 6(3):e1277306 (2017).
Knab et al. Nucleotide parasitism by Simkania negevensis (Chlamydiae). J. Bacterial. 193:225-235 (2011).
Koshkin et al., LNA (locked nucleic acids): synthesis of the adenine, cytosine, guanine 5-methylcytosine, thymine and uracil bicyclonucleoside monomers, oligomerisation, and unprecedented nucleic acid recognition, Tetrahedron, vol. 54(14), pp. 3607-3630, 1998.
Kranaster et al. Increased single-nucleotide discrimination in allele-specific polymerase chain reactions through primer probes bearing nucleobase and 2'-deoxyribose modifications. Chem EurJ 13(21):6115-6122 (2007).
Krieg et al. Improved IL-2 immunotherapy by selective stimulation of IL-2 receptors on lymphocytes and endothelial cells. PNAS USA 107:11906-11911 (2010).
Kroschwitz. The Concise Encyclopedia of Polymer Science and Engineering. (pp. 858-859) (1990).
Kubelka et al. Synthesis of 2,6-disubstituted pyridin-3-yl C-2'-deoxyribonucleosides through chemoselective transformations of bromo-chloropyridine C-nucleosides. Org. Biomol. Chem. 11:4702-4718 (2013).
Kumar et al., The First Analogues of LNA (Locked Nucleic Acids): Phosphorothioate LNA and 2'-Thio-LNA, Bioorg Med Chem Lett, vol. 8, pp. 2219-2222, 1998.
Kutyavin. Use of base-modified duplex-stabilizing deoxynucleoside 5'-triphosphates to enhance the hybridization properties of primers and probes in detection polymerase chain reaction. Biochemistry 4 (51):13666-13673 (2008).
Kwoh et al. Transcription-based amplification system and detection of amplified human immunodeficiency virus type 1 with a bead-based sandwich hybridization format. PNAS USA 86:1173-1177 (1989).
Landy. Mechanistic and structural complexity in the site-specific recombination pathways of Int and FLP. Curr Opin Genet Dev. 3(5):699-707 (1993).
Langowski et al. The CD122-biased immunostimulatory cytokine NKTR-214 combined with checkpoint blockade leads to mobiliza-

(56) References Cited

OTHER PUBLICATIONS tion of anti-tumor immunity and synergistic activity. Poster Abstract 311. 2016 CR-CIMT-EATIR-AACR Cancer Immunotherapy Conference (2016).
Lavergne et al. FRET Characterization of Complex Conformational Changes in a Large 16S Ribosomal RNA Fragment Site-Specifically Labeled Using Unnatural Base Pairs. ACS Chem Biol 11 (5): 1347-53 (2016).
Lavergne et al. Major groove substituents and polymerase recognition of a class of predominantly hydrophobic unnatural base pairs. Chem. Eur. J. 18:1231-1239 (2012).
Lavergne et al., Expanding the scope of replicable unnatural DNA: Stepwise optimization of a predominantly hydrophobic base pair, JAGS, vol. 135, pp. 5408-5419, 2013.
Lazear et al. Targeting of IL-2 to cytotoxic lymphocytes as an improved method of cytokine-driven immunotherapy. Oncoimmunology 6(2):e1265721 (2017).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127 (36): 124 70-1 (2005).
Leconte et al. Selective Inactivation of the 3' to 5' exonuclease activity of *Escherichia coli* DNA polymerase I by heat. Nucl Acids Res 11 :7505-7515 (1983).
Ledbetter et al. Editorial overview: Expanding the genetic alphabet and code. Curr Opin Chem Biol 46:A1-A2 (2018).
Ledbetter et al. Site-Specific Labeling of DNA via PCR with an Expanded Genetic Alphabet. Methods Mol Biol 1973:193-212 (2019).
Ledbetter et al., Reprograming the Replisome of a Semisynthetic Organism for the Expansion of the Genetic Alphabet, J Am Chem Soc, vol. 140, pp. 758-765, 2018.
Letourneau et al. IL-2/anti-IL-2 antibody complexes show strong biological activity by avoiding interaction with IL-2 receptor alpha subunit CD25. PNAS USA 107:2171-2176 (2010).
Letsinger et al., Cholesteryl-conjugated oligonucleotides: Synthesis, properties, and activity as inhibitors of replication of human immunodeficiency virus in cell culture, PNAS, vol. 86, pp. 6553-6556, 1989.
Levin et al. Exploiting a natural conformational switch to engineer an Interleukin-2 superkine. Nature 484 (7395):529-533 (Mar. 25, 2012). doi: 10.1038/nature10975.
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Feldman et al. Chemical Stabilization of Unnatural Nucleotide Triphosphates for the in Vivo Expansion of the Genetic Alphabet. J Am Chem Soc 139(6):2464-2467 (2017).

Feldman et al. Optimization of Replication, Transcription, and Translation in a Semi-Synthetic Organism. J Am Chem Soc 141:10644-10653 (2019).
Feldman et al., In Vivo Structure-Activity Relationships and Optimization of an Unnatural Base Pair for Replication in a Semi-Synthetic Organism, J Am Chem Soc, vol. 139, pp. 11427-11433, 2017.
Feldman. Expansion of the Genetic Alphabet: A Chemist's Approach to Synthetic Biology. Ace Chem Res 51 (2):394-403 (2018).
Fersht. Enzyme Structure and Mechanism, 2nd ed., W. H. Freeman & Co., New York (pp. 350-351) (1985).
Fidanza et al. Site-specific labeling of DNA sequences containing phosphorothioate diesters. JAGS 114 (14):5509-5517 (2002).
Fisher et al. Chlamydia trachomatis Transports NAD via the Npt1 ATP/ADP Translocase. Journal of Bacteriology 195 (15):3381-3386 (2013).
Fi Danza et al. Functionalization of oligonucleotides by the incorporation of thio-specific reporter groups. In Protocols for Oligonucleotide Conjugates. Protocols for Oligonucleotide Conjugates: Synthesis and Analytical Techniques 26:121-143 (1994).
Floros et al. Anticancer Cytokines: Biology and Clinical Effects of Interferon-a2, Interleukin (IL)-2, IL-15, IL-21, and L-12. Semin Oncol 42(4):539-548 (2015).
Fourrey et al. Photo Rearrangement of Phenyl Selenide Derivatives Access to Selenium Substituted C Nucleosides. Tetrahedron Letters 21 :455-458 (1980).
Friedhoff et al. Quantitative polymerase chain reaction with oligodeoxynucleotide ligation assay/enzyme-linked Immunosorbent assay detection. Anal Biochem 215(1):9-16 (1993).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of 13-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279 (12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Gong et al., Recent advances in bioorthogonal reactions for site-specific protein labeling and engineering, Tetrahedron Letters, vol. 56, pp. 2123-2131, 2015.
Goodman. Error-prone repair DNA polymerases in prokaryotes and eukaryotes. Annu. Rev. Biochem. 71:17-50 (2002).
Guatelli et al. Isothermal, in vitro amplification of nucleic acids by a multienzyme reaction modeled after retroviral replication. PNAS USA 87(5):1874-1878 (1990).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbial. 60:1534-1545 (2006).
Hampton et al., Design of substrate-site-directed inhibitors of adenylate kinase and hexokinase. Effect of substrate substituents on affinity on affinity for the adenine nucleotide sites, J Med Chem, vol. 19, pp. 1371-1377, 1976.
Hampton et al., Design of substrate-site-directed irreversible inhibitors of adenosine 5'- phosphate aminohydrolase. Effect of substrate substituents on affinity for the substrate site, J Med Chem, vol. 19(8), pp. 1029-1033, 1976.

(56) References Cited

OTHER PUBLICATIONS

Hampton et al., Synthesis of 6'-cyano-6'-deoxyhomoadenosine-6'-phosphonic acid and its phosphoryl and pyrophosphoryl an hydrides and studies of their interactions with adenine nucleotide utilizing enzymes, J Am Chem Soc, vol. 95(13), pp. 4404-4414, 1973.
Hancock et al. Expanding the Genetic Code of Yeast for Incorporation of Diverse Unnatural Amino Acids via a Pyrrolysyl-tRNA Synthetase/tRNA Pair. JAGS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacterial. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125 (32):9638-9646 (2003).
Hinnisdaels et al. Direct cloning of PCR products amplified with Pwo DNA polymerase. Biotechniques 20:186-188 (1996).
Hirao et al. An unnatural base pair between imidazolin-2-one and 2-amino-6-(2-thienyl)purine in replication and transcription. Nucleic Acids Res Suppl. 2(1):37-38 (2002).
Hirao et al., Unnatural base pair systems toward the expansion of the genetic alphabet in the central dogma. Proceedings of the Japan Academy, Series B, Phys Biol Sci. 88:345-367 (2012).
Horn et al. Bacterial endosymbionts of free-living amoebae. J. Eukaryot. Microbial. 5:509-514 (2004).
Hu et al. The Generation of Low Toxicity Interleukin-2 Fusion Proteins Devoid of Vasopermeability Activity. Blood 101 (12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al., From Phosphate to Bis(methylene) Sulfone: Non-Ionic Backbone Linkers in DNA, Helvetica Chimica Acta, vol. 85, pp. 2777-2806, 2002.
Hwang et al. Polymerase recognition and stability of fluorosubstituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and salvation. Nucleic Acids Res 37(14):4757-4763 (2009).
Hwang et al. Unnatural substrate repertoire of A, B, and X family DNA polymerases. J Am Chem Soc 130 (44):14872-14882 (2008).
Imran et al. Influence of architecture of high molecular weight linear and branched poly glycerolspolyglycerols on their biocompatibility and biodistribution. Biomaterials 33:9135-914 7 (2012).
Insight-Esprit Study Group et al. Interleukin-2 Therapy in Patients with HIV Infection. N Engl J Med. 361 (16):1548-59 (2009).
Ishizuka et al. Site-specific functionalization of RNA molecules by an unnatural base pair transcription system via click chemistry. Chem. Comm. 48:10835-10837 (2012).
Jager et al., Oligonucleotide N-alkylphosphoramidates: synthesis and binding to polyn ucleotides, Biochemistry, vol. 27, pp. 7247-7246, 1988.
Emerson et al., "NMR Characterization of Interleukin-2 in Complexes with the IL-2R Receptor Component, and with Low Molecular Weight Compounds that Inhibit the IL-2/IL-R interaction", Protein Science, vol. 12 (Dec. 31, 2003).
Ghelani et al., "Defining the Threshold IL-2 Signal Required for Induction of Selective Treg Cell Responses Using Engineered IL-2 Muteins", Frontiers in Immunology, vol. 11, Article 1106, figure 2, (Jun. 30, 2020).
Lawrence et al., "How PEGylation influences protein conformational stability", Current Opinion in Chemical Biology, Current Biology Ltd, London, GB, vol. 34, pp. 88-94 (Aug. 28, 2016).
Levin et al., "Exploiting a Natural Conformational Switch to Engineer an Interleukin-2 Superkine", Nature, vol. 484, No. 7359, (Apr. 26, 2012).
Mei et al., "Site-Mutation of Hydrophobic Core Residues Synchronically Poise Super Interleukin 2 for Signaling: Identifying Distant Structural Effects through Affordable Computations", International Journal of Molecular Science, vol. 19, No. 3, Article 916 (Mar. 20, 2018).
Prometheus Laboratories Inc., FDA Label for Proleukin (Aldesleukin), 19 pages (2011).
Ptacin et al., "A CD25-biased interleukin-2 for autoimmune therapy engineered via a semi-synthetic organism", Communications Medicine, 4:58, pp. 1-16, (2024).
Rao et al., "Interleukin-2 Mutants with Enhanced A-Receptor Subunit Binding Affinity", Protein Engineering, vol. 16, No. 12, (Dec. 31, 2003).
Chen et al., Selective chemical labeling of proteins, Org. Biomol. Chem., vol. 14, p. 5417, 2016.
Chien et al. Deoxyribonucleic acid polymerase from the extreme thermophile Thermus aquaticus. J Bacteriol 127:1550-1557 (1976).
Cleary et al. Production of complex nucleic acid libraries using highly parallel in situ oligonucleotide synthesis. Nat Methods 1 (3):241-248 (2004).
Collingwood et al., The Synthesis and Incorporation in Oligonucleotides of a Thymidine Dimer Containing an internucleoside Phosphinate Linkage, Synlett vol. 7, pp. 703-705, 1995.
Co-pending U.S. Appl. No. 16/634,479, filed Jan. 27, 2020.
Co-pending U.S. Appl. No. 16/634,487, filed Jan. 27, 2020 also cited herein as US Publication No. 20200231644.
Co-pending U.S. Appl. No. 16/634,487, filed Jan. 27, 2020.
Co-pending U.S. Appl. No. 16/803,816, filed Feb. 27, 2020 also cited herein as US Publication No. 20200188484.
Co-pending U.S. Appl. No. 16/993,967, filed Aug. 14, 2020 also cited herein as US Publication No. 20210046160.
Co-pending U.S. Appl. No. 16/999,638, filed Aug. 21, 2020 also cited herein as US Publication No. 20210054040.
Co-pending U.S. Appl. No. 17/001,965, filed Aug. 25, 2020 also cited herein as US Publication No. 20200399338.
Co-pending U.S. Appl. No. 17/016,003, filed Sep. 9, 2020 also cited herein as US Publication No. 20210070827.
Co-pending U.S. Appl. No. 17/313,579, filed May 6, 2021.
Co-pending U.S. Appl. No. 17/350,672, filed Jun. 17, 2021.
Co-pending U.S. Appl. No. 17/357,615, filed Jun. 24, 2021.
Co-pending U.S. Appl. No. 16/413,209, filed May 15, 2019.
Co-pending U.S. Appl. No. 16/413,219, filed May 15, 2019.
Co-pending U.S. Appl. No. 16/518,715, filed Jul. 22, 2019.
Co-pending U.S. Appl. No. 16/530,742, filed Aug. 2, 2019.
Co-pending U.S. Appl. No. 16/535,992, filed Aug. 8, 2019.
Crooke et al., Pharmacokinetic properties of several novel oligonucleotide analogs in mice, J Pharmacol Exp Ther, vol. 277, pp. 923-937, 1996.
Dahl et al. Discovery and validation of a series of aryl sulfonamides as selective inhibitors of tissue-nonspecific alkaline phosphatase (TNAP). J Med Chem 52(21):6919-6925 (2009).
De Mesmaeker et al., Amide-Modified Oligonucleotides with Preorganized Backbone and Furanose Rings: Highly Increased Thermodynamic Stability of the Duplexes Formed with their RNA and DNA Complements, Synlett, vol. 11, pp. 1287-1290, 1997.

(56) References Cited

OTHER PUBLICATIONS

Deiters et al. Site-specific PEGylation of proteins containing unnatural amino acids. Bioog Med Chem Lett 14:57 43-57 45.
Dhami et al., Systematic exploration of a class of hydrophobic unnatural base pairs yields multiple new candidates for the expansion of the genetic alphabet, Nucleic Acids Res, vol. 42, pp. 10235-10244, 2014.
Diab et al. NKTR-214 (CD-122-biased agonist) plus nivolumab in patients with advanced solid tumors: Preliminary phase 1/2 results of Pivot. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al., Progress Toward a Semi-Synthetic Organism with an Unrestricted Expanded Genetic Alphabet, J Am Chem Soc., vol. 140, pp. 16115-16123, 2018.
Dozier et al. Site-Specific PEGylation of Therapeutic Proteins, Int. J Mol Sci. Oct. 2015; 16(10):25831-25864.
Dranoff. Cytokines in cancer pathogenesis and cancer therapy. Nature Reviews Cancer 4:11-22 (2004).
Dufour. THOR-707, an engineered not-alpha IL-2, for the treatment of solid tumors induces strong immunological responses in vivo. CSCO Immunotherapy Seminar Mar. 22-23, 2019 Shanghai, China (12 pgs).
Dumas et al., Designing logical codon reassignment—Expanding the chemistry in biology, Chem Sci, vol. 6, pp. 50-69 2015.
Dupradeau et al. Differential salvation and tautomer stability of a model base pair within the minor and major grooves of DNA. J Am Chem Soc 127(44):15612-7 (2005).
Eggertsson et al. Transfer ribonucleic acid-mediated suppression of termination codons in *Escherichia coli*. Microbial Rev 52(3):354-374 (1988).
Egholm et al. PNA hybridizes to complementary oligonucleotides obeying the Watson-Crick hydrogen-bonding rules. Nature 365(6446):566-568 (1993).
El Yacoubi et al. Biosynthesis and function of posttranscriptional modifications of transfer RNAs. Annu Rev Genet 16:69-95 (2012).
Elayadi et al., Application of PNA and LNA oligomers to chemotherapy, Curr Opinion Invens Drugs, vol. 2, pp. 558-561, 2001.
Ellington et al. In vitro selection of RNA molecules that bind specific ligands. Nature 346:818-822 (1990).
Enablement Decision Tree, Example F, situation 1. http://www.USPTO.gov/web/offices/pac/dapp/1 pecba.htnn#7 >. accessed Aug. 18, 2019 (72 pgs).
Engleerg-Kukla et al. Chapter 60: Suppression of Termination Codons. *Escherichia coli* and *Salmonella* Cellular and Molecular Biology (pp. 909-921) (1996).
Englisch et al., Chemically Modified Oligonucleotides as Probes and Inhibitors, Angew. Chem. Int. Ed. Eng., vol. 30, pp. 613-629, 1991.
Eppacher et al., Synthesis and Incorporation of C(5')-Ethynylated Uracil-Derived Phosphoramidites into RNA, Helvetica Chimica Acta, vol. 87, pp. 3004-3020, 2004.
Extended European Search Report, European Patent Application No. 18840856.1, 10 pages, Mar. 29, 2021.
Fa et al. Expanding the substrate repertoire of a DNA polymerase by directed evolution. J Am Chem Soc 126 (6):1748-54 (2004).

Fairhurst et al., Synthesis and Hybridisation Properties of Phosphonamidate Ester Modified Nucleic Acid, Synlett, vol. 4, pp. 467-472, 2001.
Fan et al. Rationally evolving IRNAPyl for efficient incorporation of noncanonical amino acids. Nucleic Acids Res 43 (22):e156 (2015).
Feldman et al. A Tool for the Import of Natural and Unnatural Nucleoside Triphosphates into Bacteria. J Am Chem Soc 140(4):1447-1454 (2018).
Li et al. Synthesis of linear polyether polyol derivatives as new materials for bioconjugation. Bioconjugate ChemChem 20:780-789 (2009).
Liu et al. Adding new chemistries to the genetic code. Annu Rev Biochem 79:413-444 (2010).
Lizardi et al. Exponential amplification of recombinant-RNA hybridization probes. Nature Biotechnology 6:1197-1202 (1988).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. Sci BX 3(27):2 pgs (2010).
Ludwig et al. Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Lyon et al. Self-hydrolyzing maleimides improve the stability and pharmacological properties of antibody-drug conjugates. Nat. Biotechnol. 32(10):1059-1062 (2014).
Malyshev et al. PCR with an Expanded Genetic Alphabet. JACS 131 (41):14620-14621 (2009).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Malyshev et al., A semi-synthetic organism with an expanded genetic alphabet, Nature, vol. 509(7500), pp. 385-388, 2014.
Malyshev et al., Efficient and sequence-independent replication of DNA containing a third base pair establishes a functional six-letter genetic alphabet, PNAS USA, vol. 109, pp. 12005-12010, 2012.
Manoharan et al., Chemical Modifications to Improve Uptake and Bioavailability of Antisense Oligonucleotides, Ann N.Y. Acad. Scie, vol. 660, pp. 306-309, 1992.
Manoharan et al., Cholic Acid-Oligonucleotide Conjugates for Antisense Applications, Bioorg. Med. Chem. Let., vol. 4, pp. 1053-1060, 1994.
Manoharan et al., Introduction of a Lipophilic Thioether in the Minor Groove of Nucleic Acids for Antisense Applications, Bioorg. Med. Chem. Let., vol. 3, pp. 2765-2770, 1993.

(56) References Cited

OTHER PUBLICATIONS

Manoharan et al., Lipidic Nucleic Acids, Tetrahedron Lett, vol. 36, pp. 3651-3654, 1995.
Manoharan et al., Oligonucleotide Conjugates: Alteration of the Pharmacokinetic Properties of Antisense Agents, Nucleosides & Nucleotides, vol. 14, pp. 969-973, 1995.
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129 (17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128 (19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci, Oligonucleotide Analogs: an Overview, Oligonucleotides as therapeutic agents, Chadwick and Cardew ed., Ciba Foundation Symposium 209, pp. 5-18, 1997.
McMinn et al. Efforts toward Expansion of the Genetic Alphabet: DNA Polymerase Recognition of a Highly Stable, Self-Pairing Hydrophobic Base. J. Am. Chem. Soc. 121 :11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15RI3/yc Receptor. J Immunol 198(12):4563-4568 (2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Meyers et al. Optimal alignments in linear space. Cabios 4:11-17 (1989).
Micklefield, Backbone Modification of Nucleic Acids: Synthesis, Structure and Therapeutic Applications, Current Medicinal Chemistry, vol. 8, pp. 1157-1179, 2001.
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al., Substrate Properties of C'-Methylnucleoside and C'-Methyl-2'-deoxynucleoside 5'-Triphosphates in RNA and DNA Synthesis Reactions Catalysed by RNA and DNA Polymerases, Nucleosides & Nucleotides, vol. 10 (1-3), pp. 339-343, 1991.
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al., Conformation and interaction of dinucleoside mono- and diphosphates. V. Syntheses and properties of adenine and thymine nucleoside alkyl phosphotriesters, the neutral analogs of dinucleoside monophosphates, JAGS, vol. 93, pp. 6657-6665, 1971.
Miroux et al. Over-production of proteins in *Escherichia coli*: mutant hosts that allow synthesis of some membrane proteins and globular proteins at high levels. J Mol Biol 260:289-298 (1996).
Mishra et al., Improved leishmanicidal effect of phosphorotioate antisense oligonucleotides by LDL-mediated delivery, Biochem Biophys Acta, vol. 1264, pp. 229-237, 1995.

Montero et al. Nucleosides de synthese XVI: Sur une synthese selective de divers ribofuranosyl-1-purines. Journal of Heterocyclic Chemistry 15(6):929-935 (1978) (English Abstract).
Morris et al. Synthetic Biology Parts for the Storage of Increased Genetic Information in Cells. ACS Synth Biol 6 (10):1834-1840 (2017).
Mulligan et al. Expression of a bacterial gene in mammalian cells. Science 209:1422-1427 (1980).
Mullis et al. Specific enzymatic amplification of DNA in vitro the polymerase chain reaction. Cold Spring Harbor Symp. Quant. Biol. 51 :263 (1986).
Myers et al. Reverse transcription and DNA amplification by a Thermus thermophilus DNA polymerase. Biochemistry 30:7661-7666 (1991).
Nakazawa et al. UV and skin cancer: specific p53 gene mutation in normal skin as a biologically relevant exposure measurement. PNAS USA 91 (1):360-364 (1994).
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon, Chapter 8: Oligonucleotide Phosphorothioates in Protocols for Oligonucleotides and Analogs, Synthesis and Properties. Humana Press, pp. 165-190, 1993.
U.S. Appl. No. 15/302,874 Office Action dated Jul. 27, 2018.
U.S. Appl. No. 15/302,874 Office Action dated Jun. 19, 2019.
U.S. Appl. No. 15/302,874 Office Action dated Mar. 13, 2018.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,219 Office Action dated Aug. 22, 2019.
Vaishampayan et al. A Phase 1 Trial of ALKS 4230, an Engineered Cytokine Activator of NK and Effector T Cells, in Patients with Advanced Solid Tumors. Poster for Abstract #TPS3111 (Asco 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Vazquez-Lomardi et al., "Potent antitumour activity of interleukin-2-Fc fusion proteins requires Fc-mediated depletion of regulatory T-cells", Nature Communications, vol. 8, May 12, 2017.
Vazquez-Lombardi et al. Potent antitumour activity of the interleukin-2-Fc fusion proteins requires Fc-mediated depletion of regulatory T-cells. Nat Comm 8:15373 (2017).
Verma. Retroviral vectors for gene transfer. In: Microbiology (Leive Let al., eds., Ann. Soc. Microbial) American Society of Microbiology, Washington, DC, p. 229-232 (1985).
Verma. The reverse transcriptase. Biochim Biophys Acta. 473:1-38 (1977).
Vrudhula et al., Isozyme-specific enzyme inhibitors. 13. S-[5'(R)-[(N-triphosphoamino)methyl]adenosyl]-L-homocysteine, a potent inhibitor of rat methionine adenosyltransferases, J Med Chem, vol. 30, pp. 888-894, 1987.
Wahlestedt et al., Potent and nontoxic antisense oligonucleotides containing locked nucleic acids, PNAS USA, vol. 97, pp. 5633-5638, 2000.
Waldmann et al. The Shared and Contrasting Roles of IL2 and IL 15 in the Life and Death of Normal and Neoplastic Lymphocytes: Implications for Cancer Therapy. Cancer Immunol Res 3(3):219-227 (2015).

(56) References Cited

OTHER PUBLICATIONS

Walker et al. Combination of NKTR-214 and Radiotherapy (RT) to reverse anergy and expand specific CD8 T cells. Poster (SITC 2017).
Wan et al. Pyrrolysyl-tRNAPyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its a, Is, and ye Receptors. Science 310:1159-63 (2005).
Wang et al., Biophysical and biochemical properties of oligodeoxynucleotides containing 4'-C-and 5'-C-substituted thymidines, Bioorg Med Chem Lett, vol. 9, pp. 885-890, 1999.
Wang et al., Synthesis of Azole Nucleoside 5 '-Monophosphate Mimics (P1 Ms) and Their Inhibitory Properties of IMP Dehydrogenases, Nucleosides Nucleotides & Nucleic Acids, vol. 23(1 & 2), pp. 317-337, 2004.
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251 :389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Reverse transcriptase. CRC Grit Rev Biochem 3:289-347 (1975).
Wu et al. Synthesis of Site-Specific Radiolabeled Antibodies for Radioimmunotherapy via Genetic Code Expansion. Bioconjugate Chem. 27:2460-2468 (2016).
Wu et al., Functionalization of the sugar moiety of oligoribonucleotides on solid support, Bioconjugate Chem, vol. 10, pp. 921-924, 1999.
Wu et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, vol. 83, pp. 1127-1143, 2000.
Wurm et Al. Squaric acid mediated synthesis and biological activity of a library of linear and hyperbranched poly (glycerol)-protein conjugates. Biomacromolecules 13: 1161-1171 (2012).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J Immunol 145:873-877 (1990).
Yamashige et al. Highly specific unnatural base pair systems as a third base pair for PCR amplification. Nucleic Acids Res. 40:2793-2806 (2012).
Yan et al. Nucleoside monophosphate kinases: structure, mechanism, and substrate specificity. Adv. Enzymol. Relat. Areas Mol. Biol. 73:103-134 (1999).
Young et al., Beyond the canonical 20 amino acids: expanding the genetic lexicon, J Biol Chem, vol. 285, pp. 11039-11044, 2010.
Yu et al. Polymerase recognition of unnatural base pairs. Angew Chem Int Ed Engl 41 (20):3841-4 (2002).
Zalevsky. Jefferies 2016 Global Healthcare Conference. PowerPoint presentation (Nov. 16, 2016).
Zhang et al. Semisynthetic Organisms with Expanded Genetic Codes. Biochemistry 57:2177-2178 (20180.
Zhang et al. Studies of nucleoside transporters using novel autofluorescent nucleoside probes. Biochemistry 45 (4):1087-1098 (2006).
Zhang et al., "Site-specific PEGylation of interleukin-2 enhances immunosuppression via the sustained activation of regulatory T cells," Nature Biomed. Engin., 5: 1288-1305 (2021).
Zhang et al., A semisynthetic organism engineered for the stable expansion of the genetic alphabet, PNAS USA, vol. 114(6), pp. 1317-1322, 2017.
Zhang et al., A Semi-Synthetic Organism that Stores and Retrieves Increased Genetic Information, Nature, vol. 551 (7682), pp. 644-647, 2017.
Saha et al., 5'-Methyl-DNA-A New Oligonucleotide Analog: Synthesis and Biochemical Properties, J Org Chem, vol. 60, pp. 788-789, 1995.
Saison-Behmoaras et al., Short modified antisense oligonucleotides directed against Ha-ras point mutation induce selective cleavage of the mRNA and inhibit T24 cells proliferation, EMBO J, vol. 10, pp. 1111-1118, 1991.
Sakaguchi et al. Immunologic self-tolerance maintained by activated T cells expressing IL-2 receptor alpha-chains (CD25). Breakdown of a single mechanism of self-tolerance causes various autoimmune diseases. J Immunol 155 (3):1151-64 1995).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schmied et al. Efficient Multisite Unnatural Amino Acid Incorporation in Mammalian Cells via Optimized Pyrrolysyl tRNA Synthetase/tRNA Expression and Engineered eRF1. JAGS 136:15577-15583 (2014).
Schultz et al., Oligo-2'-fluoro-2'-deoxynucleotide N3'—> PS' phosphoramidates: synthesis and properties, Nucleic Acids Res, vol. 24, pp. 2966-2973, 1996.
Search Report, Taiwan Application No. 107127148, Apr. 12, 2021.
Seo et al. Improved High-Efficiency Organic Solar Cells via Incorporation of a Conjugated Polyelectrolyte Interlayer. JAGS 133:8416-8419 (2011).
Seo et al. Major groove derivatization of an unnatural base pair. Chembiochem 10(14):2394-2400 (2009).
Seo et al. Optimization of an unnatural base pair toward natural-like replication. J Am Chem Soc 131 :3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JAGS 131 (14):5046-5047 (2009).
Shaloiko et al. Effective non-viral leader for cap-independent translation in a eukaryotic cell-free system. Biotechnology and Bioengineering 88(6):730-739 (2004).
Shanafelt et al., "A T-cell-selective interleukin 2 mutein exhibits potent antitumor activity and is well tolerated in vivo," Nature Biotechnology, vol. 18, No. 11, pp. 1197-1202, 2000.
Sharma et al. NKTR-214 enhances anti-tumor T cell immune responses induced by checkpoint blockade or vaccination. Poster (SITC 2017).
Shea et al. Synthesis, hybridization properties and antiviral activity of lipid-oligodeoxynucleotide conjugates. Nucl. Acids Res 18:3777-3783 (1990).
Shimizu et al. Cell-free translation systems for protein engineering. Febs J 273:4133-4140 (2006).
Sierzputowska-Gracz et al. Chemistry and structure of modified uridines in the anticodon, wobble position of transfer RNA are determined by thiolation. J Am Chem Soc 109:7171-7177 (1987).
Sim et al. IL2 Variant Circumvents ICOS+ Regulatory T-cell Expansion and Promotes NK Cell Activation. Cancer Immunol Res. 4(11):983-995 (2016).
Singh et al., LNA (locked nucleic acids): synthesis and high-affinity nucleic acid recognition, Chem Commun, vol. 4, pp. 455-456, 1998.

(56) References Cited

OTHER PUBLICATIONS

Singh et al., Synthesis of 2'-amino-LNA: A novel conformationally restricted high-affinity oligonucleotide analogues with a handle, J Bio Chem, vol. 63, pp. 10035-10039, 1998.
Sivakumar et al. Comparison of Vascular Leak Syndrome in Mice treated with IL21 or IL2. Comparative Medicine 63 (1 ): 13-21 (2013).
Slagle et al. Click Conjugation of Cloaked Peptide Ligands to Microbubbles. Bioconjug Chem 29(5):1534-1543 (2018).
Sockolosky et al. Selective targeting of engineered T cells using orthogonal IL-2 cytokine-receptor complexes. Science 359(6379):1037-1042 (Mar. 2, 2018).
Southern et al. Transformation of mammalian cells to antibiotic resistance with a bacterial gene under control of the SV40 early region promoter. J Mol Appl Genet 1 :327-341 (1982).
Spangler et al. Antibodies to Interleukin-2 Elicit Selective T Cell Subset Potentiation through Distinct Conformational Mechanism. Immunity 42:815-825 (2015).
Srivastava et al., Five- and six-membered conformationally locked 2',4'-carbocyclic ribo-thymidines: synthesis, structure, and biochemical studies, J Am Chem Soc, vol. 129(26), pp. 8362-8379, 2007.
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Svinarchuk et al., Inhibition of HIV proliferation in MT-4 cells by antisense oligonucleotide conjugated to lipophilic groups, Biochimie, vol. 75, pp. 49-54, 1993.
Switzer et al. Enzymatic recognition of the base pair between isocytidine and isoguanosine. Biochemistry 32(39): 10489-10496 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under The Securities Act of 1933 filed Nov. 27, 2018 (355 pgs.).
T Jalsma et al. Signal peptide-dependent protein transport in Bacillus subtilis: a genome-based survey of the secretome. Microbial Mol Biol Rev 64(3):515-547 (2000).
Tae et al. Efforts toward expansion of the genetic alphabet: replication of DNA with three base pairs. J. Am. Chem. Soc. 123:7439-7440 (2001).
Takagi et al. Characterization of DNA polymerase from Pyrococcus sp. strain KOD1 and its application to PCR. Appl Environ Microbiol 63(11):4504-4510 (1997).
Takai et al. A single uridine modification at the wobble position of an artificial tRNA enhances wobbling in an *Escherichia coli* cell-free translation system. FEBS Lett 447(1):1-4 (1999).

Tapp et al. Homogeneous scoring of single-nucleotide polymorphisms: comparison of the 5'-nuclease TaqMan assay and Molecular Beacon probes. Biotechniques 28(4):732-738 (Apr. 2000).
Tomizawa et al. Initiation of DNA synthesis in *Escherichia coli*. Annu. Rev. Biochem. 48:999-1034 (1979).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 14/910,203 Office Action dated Feb. 5, 2019.
U.S. Appl. No. 14/910,203 Office Action dated Sep. 13, 2018.
U.S. Appl. No. 15/302,874 Office Action dated Jan. 28, 2019.
Caffaro et al., Co-pending U.S. Appl. No. 18/179,198, filed Mar. 6, 2023; also cited herein as US 2023/0302089.
Caffaro et al., Co-pending U.S. Appl. No. 18/296,710, filed Apr. 6, 2023; also cited herein as US 2023/0277627.
Caffaro et al., Co-pending U.S. Appl. No. 18/296,711, filed Apr. 6, 2023.
Napolitano et al., Emergent rules for codon choice elucidated by editing rare argine codons in *Escherichia coli*, PNAS, vol. 113(38), pp. 5588-5597, 2016.
National Institute of Cancer-understanding and related topics. Accessed Aug. 18, 2019 at URL: https://www.cancer.gov/about-cancer/ understanding/what-is-cancer (9 pgs).
Nawrot et al., A novel class of DNA analogs bearing 5'-C-phosphonothymidine units: synthesis and physicochemical and biochemical properties, Oligonucleotides, vol. 16(1), pp. 68-82, 2006.
Needleman et al. A general method applicable to the search for similarities in the amino acid sequence of two proteins. J. Mol. Biol. 48:443-453 (1970).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nelson et al., N3'—> PS' Oligodeoxyribonucleotide Phosphoramidates: A New Method of Synthesis Based on a Phosphoramidite Amine-Exchange Reaction, J Org Chem, vol. 62, pp. 7278-7287, 1997.
Neumann et al., Encoding multiple unnatural amino acids via evolution of a quadruplet-decoding ribosome, Nature, vol. 464(7287), pp. 441-444, 2010.
Nguyen et al. Genetic Encoding and Labeling of Aliphatic Azides and Alkynes in Recombinant Proteins via a Pyrrolysyl-tRNA Synthetase/tRNACUA Pair and Click Chemistry. JAGS 131 :8720-8721 (2009).
Nicolini et al. The FAP-IL2v Immunocytokine is a Versatile Combination Partner for Cancer Immunotherapy. Poster (SITC 2018).
Nielsen et al., Sequence-selective recognition of DNA by strand displacement with a thymine-substituted polyamidem, Science, vol. 254, pp. 1497-1500, 1991.
Nordstrom et al. Characterization of bacteriophage T7 DNA polymerase purified to homogeneity by antithioredoxin Immunoadsorbent chromatography. J Biol Chem 256:3112-3117(1981).
Oberhauser et al., Effective incorporation of 2'-O-methyl-oligoribonucleotides into liposomes and enhanced cell association through modification with thiocholesterol, Nucl. Acids Res., vol. 20, pp. 533-538, 1992.
Office Action issued in JP Application No. 2020-503039, May 17, 2022, 4 pages.
Office Action, Taiwan Application No. 107127148, Apr. 13, 2021.
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Ohtsuki et al. Unnatural base pairs for specific transcription. PNAS USA 98(9):4922-4925 (2001).
Okamoto. Echo probes: a concept of fluorescence control for practical nucleic acid sensing. Chem. Soc. Rev. 40:5815-5828 (2011).

(56) References Cited

OTHER PUBLICATIONS

Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al., Locked nucleic acids: a promising molecular family for gene-function analysis and antisense drug development, Curr Opinion Mol Ther, vol. 3, pp. 239-243, 2001.
Osika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ostrov et al., Design, synthesis, and testing toward a 57-codon genome, Science, vol. 353(6301), pp. 819-822, 2016.
Owczarzy et al. Stability and mismatch discrimination of locked nucleic acid-DNA duplexes. Biochem. 50 (43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
Parrish et al. Functional anatomy of a dsRNA trigger: differential requirement for the two trigger strands in RNA Interference. Mol Cell 6(5):1077-1087 (2000).
Paulous et al. Comparison of the capacity of different viral internal ribosome entry segments to direct translation Initiation in poly(A)-dependent reticulocyte lysates. Nucleic Acids Res. 31(2):722-733 (2003).
PCT/US2014050423 International Search Report and Written Opinion dated Nov. 24, 2014.
PCT/US2015/025175 International Search Report and Written Opinion dated Oct. 13, 2015.
PCT/US2016/013095 International Search Report and Written Opinion dated Apr. 27, 2016.
PCT/US2018/041503 International Search Report and Written Opinion dated Nov. 7, 2018.
PCT/US2018/041509 International Search Report and Written Opinion dated Sep. 27, 2018.
PCT/US2018/045257 International Search Report and Written Opinion dated Nov. 21, 2018.
PCT/US2018/45257 Invitation to Pay Additional Fees dated Sep. 25, 2018.
PCT/US2018/45265 International Search Report and Written Opinion dated Nov. 30, 2018.
PCT/US2018/45265 Invitation to Pay Additional Fees dated Sep. 25, 2018.
Peyrottes et al., Oligodeoxynucleoside phosphoramidates (P-NH2): synthesis and thermal stability of duplexes with DNA and RNA targets, Nucleic Acids Res, vol. 24, pp. 1841-1848, 1996.
Pfannenstiel et al. A Novel, Individualized Xenograft Model of Cancer Immunotherapy and Tumor Growth Inhibition by ALKS 4230. Poster #P351 (SITC 2017).
Piccirilli et al. AC-nucleotide base pair: methylpseudouridine-directed incorporation of formycin triphosphate into RNA catalyzed by T7 RNA polymerase. Biochemistry 30(42):10350-10356 (1991).
Piccirilli et al. Enzymatic incorporation of a new base pair into DNA and RNA extends the genetic alphabet. Nature 343:33-37 (1990).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Ptacin et al., "Cytokine Conjugates for the Treatment of Autoimmune Diseases", U.S. Appl. No. 16/634,487, filed Jan. 27, 2020.
Quan et al. Circular polymerase extension cloning for high-throughput cloning of complex and combinatorial DNA libraries. Nat Protoc 6(2):242-251 (2011).
Rao et al., "High-affinity CD25-binding IL-2 mutants potently stimulate persistent T cell growth", Biochemistry, vol. 44, No. 31, Aug. 1, 2005, pp. 10696-10701.
Roessler et al. Cooperative interactions between the interleukin 2 receptor a and 13 chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1 :Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Acimovic et al. Molecular Evolution of the Equilibrative Nucleoside Transporter Family: Identification of Novel Family Members in Prokaryotes and Eukaryotes. Mol Biol Evol 12:2199-2210 (2002).
Acsadi et al. Human Dystrophin Expression in mdx Mice After Intramuscular Injection of DNA Constructs. Nature 352:815-818 (1991).
Adhikary et al. Adaptive Mutations Alter Antibody Structure and Dynamics During Affinity Maturation. Biochemistry 54(11):2085-93 (2015).
Aerni et al., Co-pending U.S. Appl. No. 17/845,495, filed Jun. 21, 2022; also cited herein as US 2022/0324792.
Agris. Decoding the genome: a modified view. Nucleic Acids Res 32:223-238 (2004).
Akbergenov et al. ARC-1, a sequence element complementary to an internal 18S rRNA segment, enhances translation efficiency in plants when present in the leader or intercistronic region of mRNAs. Nucleic Acids Res 32 (1):239-247 (2004).
Allen et al. Roles of DNA polymerase I in leading and lagging-strand replication defined by a high-resolution mutation footprint of ColE1 plasmid replication. Nucleic Acids Res. 39:7020-7033 (2011).
Alpert et al. ABRF 2003: Precipitation of Large, High-Abundance Proteins from Serum With Organic Solvents. Poster No. P111-W (10 pgs) (2003).
Ambrogell Yet al. Pyrrolysine is not hardwired fro cotranslational insertion at UAG condons. PNAS 104 (9):3141-3146 (2007).
Amiri et al. Deep origin of plastid/parasite ATP/ADP translocases. J. Mol. Evol. 56:137-150 (2003).
Arenas-Ramirez et al. Improved cancer immunotherapy by a CD25-mimobody conferring selectivity to human Interleukin-2. Sci Transl Med 8:367ra166 (2016).
Arie et al. Phylogenetic identification of n-alkane assimilating Candida yeasts based on nucleotide divergence in the 59 end of LSU rDNA gene. J Gen Appl Microbial. 46(5):257-262 (2000).
Ast et al. Diatom plastids depend on nucleotide import from the cytosol. PNAS USA 106:3621-3626 (2009).
Audia et al. Study of the five Rickettsia prowazekii proteins annotated as ATP/ADP translocases (Tic): Only Tlc1 transports ATP/ADP, while Tlc4 and T1c5 transport other ribonucleotides. J. Bacterial. 188:6261-6268 (2006).
Baba et al. Construction of *Escherichia coli* K-12 in-frame, single-gene knockout mutants: the Keio collection. Mol Syst Biol 2006. 0008 (2006).
Beigelman et al. Synthesis of 5'-C-Methyl-D-allo- & L-Talo-ribonucleoside 3'-0-Phosphoramidites & Their Incorporation into Hammerhead Ribozymes. Nucleosides and Nucleotides 14(3-5):901-905 (1995).
Bell et al., "Sustained in vivo signaling by long-lived IL-2 induces prolonged increases of regulatory T cells," Journal of Autoimmunity, vol. 56, pp. 66-80, 2015.
Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Berger et al. Stability and selectivity of unnatural DNA with five-membered-ring nucleobase analogues. J Am Chem Soc 124(7):1222-6 (2002).

(56) References Cited

OTHER PUBLICATIONS

Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28 (15):2911-2914 (2000).
Betz et al. KlenTaq polymerase replicates unnatural base pairs by inducing a Watson-Crick geometry. Nat Chem Biol 8:612-614 (2012).
Betz et al., Structural insights into DNA replication without hydrogen bonds, J Am Chem Soc, vol. 135, pp. 18637-18643, 2013.
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Bohringer et al., Synthesis of 5'-deoxy-5'-methylphosphonate linked thymidine oligonucleotides, Tet Lett, vol. 34, pp. 2723-2726, 1993.
Bordo et al. Suggestions for "safe" residue substitutions in site-directed mutagenesis. J Mol Biol 217:721-729 (1991).
Boyman et al. Selective Stimulation of T Cell subsets with Antibody-Cytokine Immune Complexes. Science 311 :1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Braasch et al., Locked nucleic acid (LNA): fine-tuning the recognition of DNA and RNA, Chem Bio, vol. 8:1-7, 2001.
Branca. Rekindling cancer vaccines. Nat Biotechnol 34(10):1019-1025 (2016).
Brauns et al. Studies on Lignin and Related Compounds: XII. Methanol Lignin. Canadian Journal of Research 13b (1):28-34 (1935).
Caffaro et al., Co-pending U.S. Appl. No. 17/735,564, filed May 3, 2022; also cited herein as US 2022/0273767.
Cann et al. A heterodimeric DNA polymerase: Evidence that members of Euryarchaeota possess a distinct DNA polymerase. PNAS USA 95:14250 (1998).
Capone et al. Amber, ochre and opal suppressor tRNA genes derived from a human serine tRNA gene. EMBO J 4 (1): 213-221 (1985).
Cariello et al. Fidelity of Thermococcus litoralis DNA polymerase (VentTM) in PCR determined by denaturing gradient gel electrophoresis Nucl Acid Res 19:4193-4198 (1991).
Carmenate et al., "Human IL-2 mutein with higher antitumor efficacy than wild type IL-2", The Journal of Immunology, vol. 190, No. 12, pp. 6230-6238, Jun. 15, 2013.
Cassell et al., "Therapeutic Enhancement of IL-2 Through Molecular Design," Current Pharmaceutical Design, vol. 8, No. 24, pp. 2171-2183, 2002.
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Charych et al. Modeling the receptor pharmacology, pharmacokinetis, and pharmacodynamics of NKTR-214, a kinetically-controlled interleukin-2 (IL2) receptor agonist for cancer immunotherapy. PLoS One 12(7):e0179431 (2017).
Charych et al., "NKTR-214, an Engineered Cytokine with Biased IL2 Receptor Binding, Increased Tumor Exposure, and Marked Efficacy in Mouse Tumor Models", Clinical Cancer Research, vol. 22, No. 3, pp. 680-690, Feb. 1, 2016.
Chastgner et al. Lack of intermediate-affinity interleukin-2 receptor in mice leads to dependence on interkeukin-2 receptor a, 13 and y chain expression for T cell growth. Eur J Immunol 26:201-206 (1996).
Chatterjee et al. A Versatile Platform for Single- and Multiple-Unnatural Amino Acid Mutagenesis in *Escherichia coli*. Biochemistry 52(10):1828-1837 (2013).
Chaturvedi et al., Stabilization of triple-stranded oligonucleotide complexes: use of probes containing alternating phosphodiester and stereo-uniform cationic phosphoramidate linkages, Nucleic Acids Res., vol. 24, pp. 2318-2323, 1996.
Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. The expanding world of DNA and RNA. Curr Opin Chem Biol 34:80-87 (2016).
Chen et al., Phosphonate Analogues of Cytosine Arabinoside Monophosphate, Phosphorus, Sulfur and Silicon, vol. 177, pp. 1783-1786, 2002.
Abbadessa et al., Co-pending U.S. Appl. No. 18/524,157 filed on Jul. 11, 2024.
Caffaro et al., Co-pending U.S. Appl. No. 18/415,445 filed Jan. 17, 2024.
Caffaro et al., Co-pending U.S. Appl. No. 18/424,573 filed Jan. 26, 2024.
Ptacin et al., Co-pending U.S. Appl. No. 18/886,814 filed Sep. 16, 2024.

Mean (±SD) Plasma Concentration versus Time Profiles Following a Single IV Bolus Dose of aldesleukin or P65_30KD and E62_30KD, E62_5KD to Female C57BL/6 mice Sustained increase in peripheral blood pSTAT5+ CD8+ T in response to P65_30KD P65_30KD induced peripheral blood expansion of CD8+ T cells P65_30KD induced peripheral blood expansion of NK cell

P65_30KD did not induce the proliferation of CD4+ Tregs

P65_30KD induces CD8+ T effector memory cell expansion

CYTOKINE CONJUGATES FOR THE TREATMENT OF PROLIFERATIVE AND INFECTIOUS DISEASES

CROSS-REFERENCE

This application is a continuation of U.S. application Ser. No. 16/803,816, filed on Feb. 27, 2020, which is a divisional of U.S. application Ser. No. 16/434,999, filed on Jun. 7, 2019, which is a continuation of International Application No. PCT/US2018/045257, filed on Aug. 3, 2018, which claims the benefit of U.S. Provisional Application No. 62/540,781, filed on Aug. 3, 2017, all of which are incorporated herein by reference in their entirety.

SEQUENCE LISTING

The instant application contains a Sequence Listing which has been submitted electronically in XML format and is hereby incorporated by reference in its entirety. Said XML copy, created on May 31, 2023, is named "2023-05-31_01183-0067-03US_ST26.xml" and is 7,196 bytes in size.

BACKGROUND OF THE DISCLOSURE

Distinct populations of T cells modulate the immune system to maintain immune homeostasis and tolerance. For example, regulatory T (Treg) cells prevent inappropriate responses by the immune system by preventing pathological self-reactivity while cytotoxic T cells target and destroy infected cells and/or cancerous cells. In some instances, modulation of the different populations of T cells provides an option for treatment of a disease or indication.

SUMMARY OF THE DISCLOSURE

Disclosed herein, in certain embodiments, are cytokine conjugates and use in the treatment of one or more indication. In some embodiments, also described herein include interleukin 2 (IL-2) conjugates and use in the treatment of one or more indications. In some instances, the one or more indications comprise cancer or a pathogenic infection. In some cases, described herein are methods of modulating the interaction between IL-2 and IL-2 receptor to stimulate or expand specific T cell, Natural Killer (NK) cell, and/or Natural killer T (NKT) cell populations. In additional cases, further described herein are pharmaceutical compositions and kits that comprise one or more interleukin conjugates (e.g., IL-2 conjugates) described herein.

Disclosed herein, in certain embodiments, is an interleukin 2 (IL-2) conjugate comprising: an isolated and purified IL-2 polypeptide; and a conjugating moiety that binds to the isolated and purified IL-2 polypeptide at an amino acid position selected from K35, T37, R38, T41, F42, K43, F44, Y45, E61, E62, E68, K64, P65, V69, L72, and Y107, wherein the numbering of the amino acid residues corresponds to SEQ ID NO: 1. In some embodiments, the amino acid position is selected from T37, R38, T41, F42, F44, Y45, E61, E62, E68, K64, P65, V69, L72, and Y107. In some embodiments, the amino acid position is selected from T37, R38, T41, F42, F44, Y45, E61, E62, E68, P65, V69, L72, and Y107. In some embodiments, the amino acid position is selected from T37, T41, F42, F44, Y45, P65, V69, L72, and Y107. In some embodiments, the amino acid position is selected from R38 and K64. In some embodiments, the amino acid position is selected from E61, E62, and E68. In some embodiments, the amino acid position is at E62. In some embodiments, the amino acid residue selected from K35, T37, R38, T41, F42, K43, F44, Y45, E61, E62, E68, K64, P65, V69, L72, and Y107 is further mutated to lysine, cysteine, or histidine. In some embodiments, the amino acid residue is mutated to cysteine. In some embodiments, the amino acid residue is mutated to lysine. In some embodiments, the amino acid residue selected from K35, T37, R38, T41, F42, K43, F44, Y45, E61, E62, E68, K64, P65, V69, L72, and Y107 is further mutated to an unnatural amino acid. In some embodiments, the unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the IL-2 conjugate has a decreased affinity to IL-2 receptor α (IL-2Rα) subunit relative to a wild-type IL-2 polypeptide. In some embodiments, the decreased affinity is about 10%, 20%, 30%, 40%, 50%, 60%, 70%, 80%, 90%, 95%, 99%, or greater than 99% decrease in binding affinity to IL-2Rα relative to a wild-type IL-2 polypeptide. In some embodiments, the decreased affinity is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 500-fold, 1000-fold, or more relative to a wild-type IL-2 polypeptide. In some embodiments, the conjugating moiety impairs or blocks the binding of IL-2 with IL-2Rα. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis (succinimidyl-propionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl) amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), 1-(p-Azidosalicylamido)-4-(iodoacetamido)butane (AsIB), N-[4-(p-azidosalicylamido) butyl]-3'-(2'-pyridyldithio)propionamide (APDP), benzophenone-4-iodoacetamide, p-azidobenzoyl hydrazide (ABH), 4-(p-azidosalicylamido)butylamine (AsBA), or p-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl) cyclohexane-1-carboxylate (sulfo-sMCC). In some embodiments, the linker further comprises a spacer. In some embodiments, the spacer comprises p-aminobenzyl alcohol (PAB), p-aminobenzyoxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate.

Disclosed herein, in certain embodiments, is an interleukin 2 (IL-2) conjugate comprising: an isolated and purified IL-2 polypeptide; and a conjugating moiety; wherein the IL-2 conjugate has a decreased affinity to an IL-2 receptor α (IL-2Rα) subunit relative to a wild-type IL-2 polypeptide. In some embodiments, the conjugating moiety is bound to an amino acid residue that interacts with IL-2Rα. In some embodiments, the conjugating moiety is bound to an amino acid residue selected from K35, T37, R38, T41, F42, K43, F44, Y45, E61, E62, E68, K64, P65, V69, L72, and Y107, wherein the numbering of the amino acid residues corresponds to SEQ ID NO: 1. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly (oxyethylated polyol), poly(olefinic alcohol), poly(vinylpyrrolidone), poly(hydroxyalkylmethacrylamide), poly(hydroxyalkylmethacrylate), poly(saccharides), poly(α- hydroxy acid), poly(vinyl alcohol), polyphosphazene, polyoxazolines (POZ), poly(N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis (succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetypamino)hexanoyl]amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), 1-(ρ-Azidosalicylamido)-4-(iodoacetamido)butane (AsIB), N-[4-(ρ-azidosalicylamido) butyl]-3'-(2'-pyridyldithio)propionamide (APDP), benzophenone-4-iodoacetamide, ρ-azidobenzoyl hydrazide (ABH), 4-(ρ-azidosalicylamido)butylamine (AsBA), or ρ-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl) cyclohexane-1-carboxylate (sulfo-sMCC). In some embodiments, the linker further comprises a spacer. In some embodiments, the spacer comprises p-aminobenzyl alcohol (PAB), p-aminobenzyoxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate.

Disclosed herein, in certain embodiments, is an isolated and modified interleukin 2 (IL-2) polypeptide comprising at least one unnatural amino acid at a position on the polypeptide that reduces binding between the modified IL-2 polypeptide and interleukin 2 receptor α (IL-2Rα) but does not significantly impair binding with interleukin 2 βγ receptor (IL-2Rβγ) signaling complex to form an IL-2/IL-2Rβγ complex, wherein the reduced binding to IL-2Rα is compared to a binding between a wild-type IL-2 polypeptide and IL-2Rα. In some embodiments, the position of the at least one unnatural amino acid is selected from K35, T37, R38, T41, F42, K43, F44, Y45, E60, E61, E62, K64, P65, E68, V69, N71, L72, M104, C105, and Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the at least one unnatural amino acid: is a lysine analogue; comprises an aromatic side chain; comprises an azido group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the protein comprises a TLR agonist. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding affinity is about 10%, 20%, 30%, 40%, 50%, 60%, 70%, 80%, 90%, 95%, or 99% decrease in binding affinity to IL-2Rα relative to a wild-type IL-2 polypeptide. In some embodiments, the decrease in binding affinity is about 1-fold, 2-fold, 3-fold, 4-fold, 5-fold, 6-fold, 7-fold, 8-fold, 9-fold, 10-fold, or more relative to IL-2Rα relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO:

1. In some embodiments, the modified IL-2 polypeptide with the decrease in binding affinity to IL-2Rα is capable of expanding CD4+ helper cell, CD8+ effector naïve and memory cell, Natural Killer (NK) cell, Natural killer T (NKT) cell populations, or a combination thereof. In some embodiments, the conjugating moiety impairs or blocks the binding of IL-2 with IL-2Rα. In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide is not significantly different than activation of said cell population by a wild-type IL-2 polypeptide, and wherein the potency of the modified IL-2 polypeptide is at least 1-fold higher than a potency of the wild-type IL-2 polypeptide. In some embodiments, the modified IL-2 polypeptide expands CD4+ T regulatory (Treg) cells by less than 20%, 15%, 10%, 5%, 1%, or 0.1% when said activator is in contact with said cell population. In some embodiments, the modified IL-2 polypeptide does not expand Treg cells in said cell population.

Disclosed herein, in certain embodiments, is an isolated and modified interleukin 2 (IL-2) polypeptide comprising at least one unnatural amino acid at a position on the polypeptide that reduces binding between the modified IL-2 polypeptide and interleukin 2 receptor α (IL-2Rα) but retains significant binding with interleukin 2 βγ receptor (IL-2Rβγ) signaling complex to form an IL-2/IL-2Rβγ complex, wherein the reduced binding to IL-2Rα is compared to binding between a wild-type IL-2 polypeptide and IL-2Rα. In some embodiments, the difference in receptor signaling potency is less than 5-fold, less than 4-fold, less than 3-fold, less than 2-fold, or less than 1-fold. In some embodiments, the position of the at least one unnatural amino acid is selected from K35, T37, R38, T41, F42, K43, F44, Y45, E60, E61, E62, K64, P65, E68, V69, N71, L72, M104, C105, and Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the conjugating moiety comprises a TLR agonist. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding affinity is about 30%, 40%, 50%, 60%, 70%, 80%, 90%, 95%, 99%, or 100% decrease in binding affinity to IL-2Rα relative to a wild-type IL-2 polypeptide. In some embodiments, the decrease in binding affinity is about 3-fold, 4-fold, 5-fold, 6-fold, 7-fold, 8-fold, 9-fold, 10-fold, or more to IL-2Rα relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in binding affinity to IL-2Rα is capable of expanding CD4+ helper cell, CD8+ effector naïve and memory cell, Natural Killer (NK) cell, Natural killer T (NKT) cell populations, or a combination thereof. In some embodiments, the conjugating moiety or the unnatural amino acid impairs or blocks the binding of IL-2 with IL-2Rα. In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some embodiments, the receptor signaling potency of the modified IL-2 polypeptide to the IL-2Rβγ complex is higher than a receptor signaling potency of the wild-type IL-2 polypeptide to the IL-2Rβγ complex. In some embodiments, the receptor signaling potency of the modified IL-2 polypeptide the IL-2Rβγ complex is lower than a receptor signaling potency of the wild-type IL-2 polypeptide the IL-2Rβγ complex. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, or higher than the second receptor signaling potency. In some embodiments, the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some embodiments, the first receptor signaling potency of the modified IL-2 polypeptide is at least 1-fold lower than a receptor signaling potency of the wild-type IL-2 polypeptide.

Disclosed herein, in certain embodiments, is an isolated and modified interleukin 2 (IL-2) polypeptide comprising at least one unnatural amino acid, wherein the isolated and modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the difference in receptor signaling potency is less than 5-fold, less than 4-fold, less than 3-fold, less than 2-fold, or less than 1-fold. In some embodiments, the position of the at least one unnatural amino acid is selected from K35, T37, R38, T41, F42, K43, F44, Y45, E60, E61, E62, K64, P65, E68, V69, N71, L72, M104, C105, and Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargylphenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl) selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly (oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the conjugating moiety comprises a TLR agonist. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding affinity is about 30%, 40%, 50%, 60%, 70%, 80%, 90%, 95%, 99%, or 100% decrease in binding affinity to IL-2Rα relative to a wild-type IL-2 polypeptide. In some embodiments, the decrease in binding affinity is about 3-fold, 4-fold, 5-fold, 6-fold, 7-fold, 8-fold, 9-fold, 10-fold, or more to IL-2Rα relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in binding affinity to IL-2Rα is capable of expanding CD4+ helper cell, CD8+ effector naïve and memory cell, Natural Killer (NK) cell, Natural killer T (NKT) cell populations, or a combination thereof. In some embodiments, the conjugating moiety or the unnatural amino acid impairs or blocks the binding of IL-2 with IL-2Rα. In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some embodiments, the receptor signaling potency of the modified IL-2 polypeptide to the IL-2Rβγ complex is higher than a receptor signaling potency of the wild-type IL-2 polypeptide to the IL-2Rβγ complex. In some embodiments, the receptor signaling potency of the modified IL-2 polypeptide the IL-2Rβγ complex is lower than a receptor signaling potency of the wild-type IL-2 polypeptide the IL-2Rβγ complex. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, or higher than the second receptor signaling potency. In some embodiments, the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some embodiments, the first receptor signaling potency of the modified IL-2 polypeptide is at least 1-fold lower than a receptor signaling potency of the wild-type IL-2 polypeptide.

Disclosed herein, in certain embodiments, is an isolated and modified interleukin 2 (IL-2) polypeptide comprising at least one unnatural amino acid, wherein the isolated and modified IL-2 polypeptide provides a first EC50 value for activating IL-2βγ signaling complex and a second EC50 value for activating IL-2αβγ signaling complex, and wherein a difference between the first EC50 and the second EC50 value is less than 10-fold. In some embodiments, the difference is less than 5-fold, less than 4-fold, less than 3-fold, less than 2-fold, or less than 1-fold. In some embodiments, the difference in receptor signaling potency is less than 5-fold, less than 4-fold, less than 3-fold, less than 2-fold, or less than 1-fold. In some embodiments, the position of the at least one unnatural amino acid is selected from K35, T37, R38, T41, F42, K43, F44, Y45, E60, E61, E62, K64, P65, E68, V69, N71, L72, M104, C105, and Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the conjugating moiety comprises a TLR agonist. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding affinity is about 30%, 40%, 50%, 60%, 70%, 80%, 90%, 95%, 99%, or 100% decrease in binding affinity to IL-2Rα relative to a wild-type IL-2 polypeptide. In some embodiments, the decrease in binding affinity is about 3-fold, 4-fold, 5-fold, 6-fold, 7-fold, 8-fold, 9-fold, 10-fold, or more to IL-2Rα relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in binding affinity to IL-2Rα is capable of expanding CD4+ helper cell, CD8+ effector naïve and memory cell, Natural Killer (NK) cell, Natural killer T (NKT) cell populations, or a combination thereof. In some embodiments, the conjugating moiety or the unnatural amino acid impairs or blocks the binding of IL-2 with IL-2Rα. In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some embodiments, the receptor signaling potency of the modified IL-2 polypeptide to the IL-2Rβγ complex is higher than a receptor signaling potency of the wild-type IL-2 polypeptide to the IL-2Rβγ complex. In some embodiments, the receptor signaling potency of the modified IL-2 polypeptide the IL-2Rβγ complex is lower than a receptor signaling potency of the wild-type IL-2 polypeptide the IL-2Rβγ complex. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, or higher than the second receptor signaling potency. In some embodiments, the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some embodiments, the first receptor signaling potency of the modified IL-2 polypeptide is at least 1-fold lower than a receptor signaling potency of the wild-type IL-2 polypeptide.

Disclosed herein, in certain embodiments, is a pharmaceutical composition comprising: an IL-2 conjugate described above; and a pharmaceutically acceptable excipient. In some embodiments, the pharmaceutical composition is formulated for parenteral administration.

Disclosed herein, in certain embodiments, is a method of treating a proliferative disease or condition in a subject in need thereof, comprising administering to the subject a therapeutically effective amount of an isolated and modified IL-2 polypeptide described above, an IL-2 conjugate described above, an IL-2Rβγ binding protein described above, an activator of a CD4+ helper cell, CD8+ effector naïve and memory cell, Natural Killer (NK) cell, or Natural killer T (NKT) cell described above, or a pharmaceutical composition described above. In some embodiments, the proliferative disease or condition is a cancer. In some embodiments, the cancer is a solid tumor cancer. In some embodiments, the solid tumor cancer is bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some embodiments, the cancer is a hematologic malignancy. In some embodiments, the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the method further comprises administering an additional therapeutic agent. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition and the additional therapeutic agent are administered simultaneously. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition and the additional therapeutic agent are administered sequentially. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition is administered prior to the additional therapeutic agent. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition is administered after the administration of the additional therapeutic agent.

Disclosed herein, in certain embodiments, is a method of expanding a CD4+ helper cell, CD8+ effector naïve and memory cell, Natural Killer (NK) cell, or Natural killer T (NKT) cell population, comprising: contacting a cell population with an isolated and modified IL-2 polypeptide described above, an IL-2 conjugate described above, an IL-2Rβγ binding protein described above, an activator of a CD4+ helper cell, CD8+ effector naïve and memory cell, Natural Killer (NK) cell, or Natural killer T (NKT) cell described above, or a pharmaceutical composition described above for a time sufficient to induce formation of a complex with an IL-2Rβγ, thereby stimulating the expansion of the Teff and/or NK cell population. In some embodiments, the isolated and modified IL-2 polypeptide described above, the IL-2 conjugate described above, the IL-2Rβγ binding protein described above, the activator of a CD4+ helper cell, CD8+ effector naïve and memory cell, Natural Killer (NK) cell, or Natural killer T (NKT) cell described above, or the pharmaceutical composition described above expands CD4+ T regulatory (Treg) cells by less than 20%, 15%, 10%, 5%, or 1% in the CD3+ cell population compared to an expansion of CD4+ Treg cells in the CD3+ cell population contacted with a wild-type IL-2 polypeptide. In some embodiments, the isolated and modified IL-2 polypeptide described above, the IL-2 conjugate described above, the IL-2Rβγ binding protein described above, the activator of a CD4+ helper cell, CD8+ effector naïve and memory cell, Natural Killer (NK) cell, or Natural killer T (NKT) cell described above, or the pharmaceutical composition described above does not expand CD4+ Treg cells in the cell population. In some embodiments, the ratio of the Teff cells to Treg cells in the cell population after incubation with the isolated and modified IL-2 polypeptide described above, the IL-2 conjugate described above, the IL-2Rβγ binding protein described above, the activator of a CD4+ helper cell, CD8+ effector naïve and memory cell, Natural Killer (NK) cell, or Natural killer T (NKT) cell described above, or the pharmaceutical composition described above is about or at least 2:1, 3:1, 4:1, 5:1, 6:1, 7:1, 8:1, 9:1, 10:1, 20:1, 50:1, or 100:1. In some embodiments, the method is an in vivo method. In some embodiments, the method is an in vitro method. In some embodiments, the method is an ex vivo method.

Disclosed herein, in certain embodiments, is a method of expanding a CD4+ helper cell population, a CD8+ effector naïve and/or memory cell population, a Natural Killer (NK) cell population, a Natural killer T (NKT) cell population, or a combination thereof, comprising: (a) contacting a cell with an IL-2 conjugate described above; and (b) interacting the IL-2 with IL-2Rβγ and IL-2Rγ subunits to form an IL-2/IL-2Rβγ complex; wherein the IL-2 conjugate has a decreased affinity to IL-2Rα subunit, and wherein the IL-2/IL-2Rβγ complex stimulates the expansion of CD4+ helper cells, CD8+ effector naïve and/or memory cells, NK cells, NKT cells, or a combination thereof.

Disclosed herein, in certain embodiments, is a kit comprising an isolated and modified IL-2 polypeptide described above, an IL-2 conjugate described above, an IL-2Rβγ binding protein described above, an activator of a CD4+ helper cell, CD8+ effector naïve and memory cell, Natural Killer (NK) cell, or Natural killer T (NKT) cell described above, or a pharmaceutical composition comprising an IL-2 conjugate described above. In some embodiments, also described herein is a kit comprising a polynucleic acid molecule encoding an IL-2 polypeptide described above.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates exemplary lysine derivatives. FIG. 2B illustrates exemplary phenylalanine derivatives.

FIG. 3B—UAA #43-89; FIG. 3C—UAA #90-128; FIG. 3D—UAA #129-167). FIGS. 5A-5D are adopted from Table 1 of Dumas et al., *Chemical Science* 2015, 6, 50-69.

FIG. 4A shows SPR analysis of IL-2 variants binding to immobilized IL-2 Rα. FIG. 4B shows SPR analysis of IL-2 variants binding to immobilized IL-2 Rβ.

FIG. 5A-FIG. 5C show exemplary IL-2 variant dose response curves for pSTAT5 signaling in human LRS primary cell populations. FIG. 5A: native IL-2; FIG. 5B: E62_30kD; and FIG. 5C: P65_30kD.

FIG. 9A shows memory CD8+CD44+ T cell proliferation at 72, 96 and 120 hours. FIG. 9B shows flow cytometry analysis of those cells at the 120 h time point.

FIG. 10A shows percentage of NK, CD8+ T and CD4+ T reg cells in P65_30-treated vs untreated (vehicle) animals at Day 5 of treatment. FIG. 10B shows the ratio of CD8+/CD4+ Treg cells in P65_30-treated and control (vehicle) animals. Data were analyzed using unpaired Student t test. *** designate P values <0.001.

FIG. 11A shows cytokine levels for aldesleukin-dosed animals and FIG. 11B for P65_30-dosed animals.

DETAILED DESCRIPTION OF THE DISCLOSURE

Figure 1:
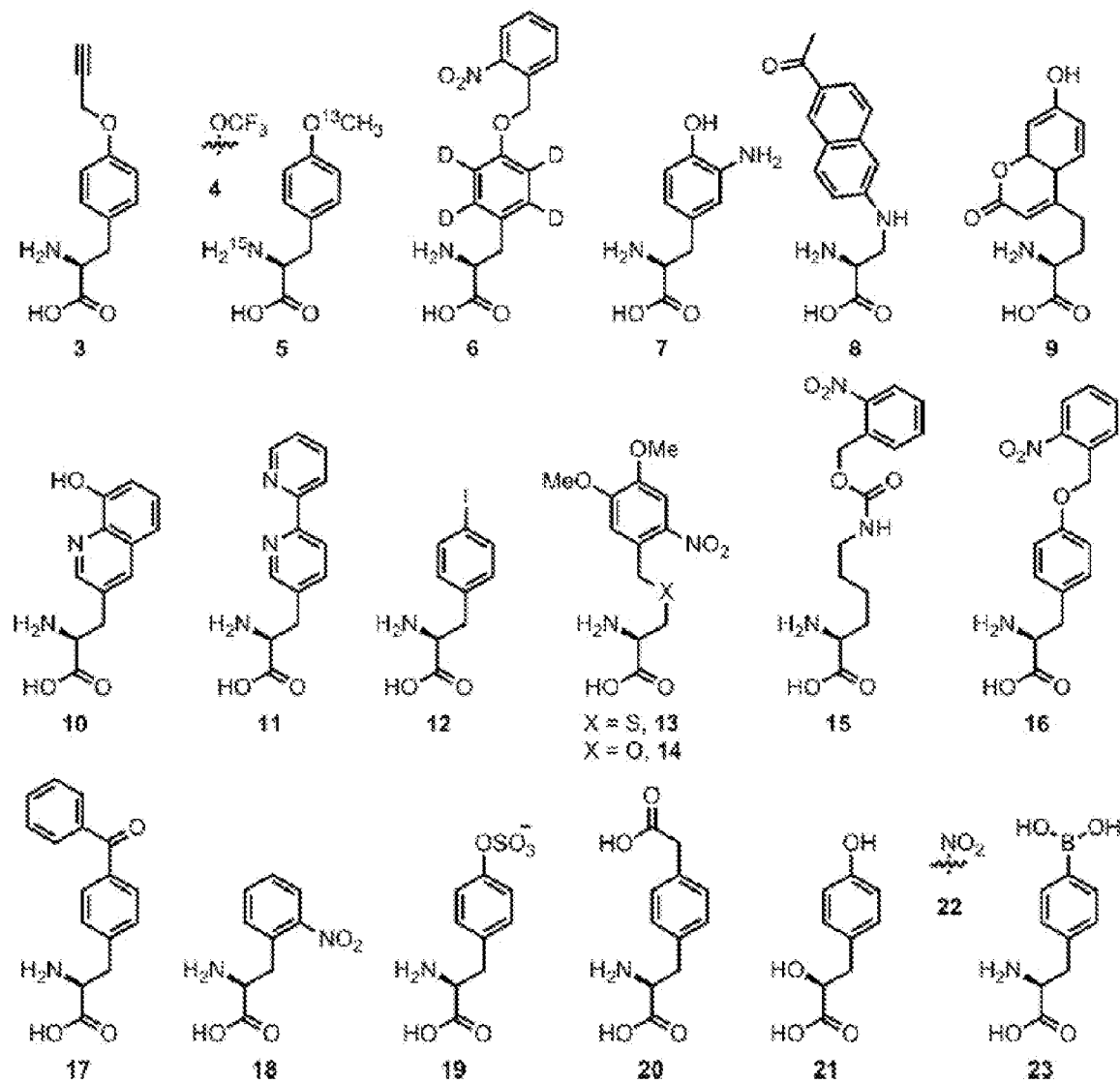
FIG. 1 shows exemplary unnatural amino acids. This figure is adapted from FIG. 2 of Young et al., "Beyond the canonical 20 amino acids: expanding the genetic lexicon," *J. of Biological Chemistry* 285(15): 11039-11044 (2010).

Cytokines comprise a family of cell signaling proteins such as chemokines, interferons, interleukins, lymphokines, tumor necrosis factors, and other growth factors playing roles in innate and adaptive immune cell homeostasis. Cytokines are produced by immune cells such as macrophages, B lymphocytes, T lymphocytes and mast cells, endothelial cells, fibroblasts, and different stromal cells. In some instances, cytokines modulate the balance between humoral and cell-based immune responses.

Interleukins are signaling proteins which modulate the development and differentiation of T and B lymphocytes, cell of the monocytic lineage, neutrophils, basophils, eosinophils, megakaryocytes, and hematopoietic cells. Interleukins are produced by helper CD4 T and B lymphocytes, monocytes, macrophages, endothelial cells, and other tissue residents. In some cases, there are about 15 interleukins, interleukins 1-13, interleukin 15, and interleukin 17.

Interleukin 2 (IL-2) is a pleiotropic type-1 cytokine whose structure comprises a 15.5 kDa four α-helix bundle. The precursor form of IL-2 is 153 amino acid residues in length, with the first 20 amino acids forming a signal peptide and residues 21-153 forming the mature form. IL-2 is produced primarily by CD4+ T cells post antigen stimulation and to a lesser extent, by CD8+ cells, Natural Killer (NK) cells, and Natural killer T (NKT) cells, activated dendritic cells (DCs), and mast cells. IL-2 signaling occurs through interaction with specific combinations of IL-2 receptor (IL-2R) subunits, IL-2Rα (also known as CD25), IL-2Rβ (also known as CD122), and IL-2Rγ (also known as CD132). Interaction of IL-2 with the IL-2Rα forms the "low-affinity" IL-2 receptor complex with a $K_d$ of about $10^{-8}$ M. Interaction of IL-2 with IL-2Rβ and IL-2Rγ forms the "intermediate-affinity" IL-2 receptor complex with a $K_d$ of about $10^{-9}$ M. Interaction of IL-2 with all three subunits, IL-2Rα, IL-2Rβ, and IL-2Rγ, forms the "high-affinity" IL-2 receptor complex with a $K_d$ of about $>10^{-11}$ M.

In some instances, IL-2 signaling via the "high-affinity" IL-2Rαβγ complex modulates the activation and proliferation of regulatory T cells. Regulatory T cells, or CD4+

CD25+Foxp3+ regulatory T (Treg) cells, mediate maintenance of immune homeostasis by suppression of effector cells such as CD4+ T cells, CD8+ T cells, B cells, NK cells, and NKT cells. In some instances, Treg cells are generated from the thymus (tTreg cells) or are induced from naïve T cells in the periphery (pTreg cells). In some cases, Treg cells are considered as the mediator of peripheral tolerance. Indeed, in one study, transfer of CD25-depleted peripheral CD4+ T cells produced a variety of autoimmune diseases in nude mice, whereas cotransfer of CD4+CD25+ T cells suppressed the development of autoimmunity (Sakaguchi, et al., "Immunologic self-tolerance maintained by activated T cells expressing IL-2 receptor alpha-chains (CD25)," *J. Immunol.* 155(3): 1151-1164 (1995)). Augmentation of the Treg cell population down-regulates effector T cell proliferation and suppresses autoimmunity and T cell anti-tumor responses.

IL-2 signaling via the "intermediate-affinity" IL-2Rβγ complex modulates the activation and proliferation of CD8+ effector T (Teff) cells, NK cells, and NKT cells. CD8+ Teff cells (also known as cytotoxic T cells, Tc cells, cytotoxic T lymphocytes, CTLs, T-killer cells, cytolytic T cells, Tcon, or killer T cells) are T lymphocytes that recognize and kill damaged cells, cancerous cells, and pathogen-infected cells. NK and NKT cells are types of lymphocytes that, similar to CD8+ Teff cells, target cancerous cells and pathogen-infected cells.

In some instances, IL-2 signaling is utilized to modulate T cell responses and subsequently for treatment of a cancer. For example, IL-2 is administered in a high-dose form to induce expansion of Teff cell populations for treatment of a cancer. However, high-dose IL2 further leads to concomitant stimulation of Treg cells that dampen anti-tumor immune responses. High-dose IL-2 also induces toxic adverse events mediated by the engagement of IL-2R alpha chain-expressing cells in the vasculature, including type 2 innate immune cells (ILC-2), eosinophils and endothelial cells. This leads to eosinophilia, capillary leak and vascular leak syndrome VLS).

Disclosed herein, in certain embodiments, is a method of selectively upregulating distinct population(s) of lymphocytes (e.g., CD4+ helper cells, CD8+ effector naïve and memory cells, NK cells, or NKT cells) through cytokine/cytokine receptor signaling. In some instances, the cytokine comprises an interleukin, an interferon, or a tumor necrosis factor. In some cases, the cytokine is a cytokine conjugate, e.g., an interleukin conjugate, an interferon conjugate, or a tumor necrosis factor conjugate. In additional cases, described herein comprise pharmaceutical compositions and kits comprising one or more cytokine conjugates described herein.

In some embodiments, also described herein is a method of selectively upregulating CD4+ helper cell, CD8+ effector naïve and memory cell, NK cell, and/or NKT cell populations through IL-2/IL-2R signaling. In some instances, IL-2 is an IL-2 conjugate, which interacts with the "intermediate-affinity" IL-2Rβγ complex, optionally with a similar potency as the IL-2Rαβγ complex, and with a weakened IL-2Rα interaction relative to wild-type IL-2. In some embodiments, further described herein are methods of treating a cancer with use of an IL-2 conjugate described herein. In additional embodiments, described herein are pharmaceutical compositions and kits which comprise one or more IL-2 conjugates described herein.

Cytokine Conjugates

In some embodiments, described herein are cytokine conjugates. In some instances, the cytokine comprises an interleukins, a tumor necrosis factor, an interferon, a chemokine, a lymphokine, or a growth factor. In some instances, the cytokine is an interleukin. In some cases, the cytokine is an interferon. In additional cases, the cytokine is a tumor necrosis factor. In further cases, the cytokine is a growth factor.

In some embodiments, described herein is an interleukin conjugate. Exemplary interleukins include, but are not limited to, interleukin 1β (IL-1β), interleukin 2 (IL-2), interleukin 7 (IL-7), interleukin 10 (IL-10), interleukin 12 (IL-12), interleukin 15 (IL-15), interleukin 18 (IL-18), and interleukin 21 (IL-21). In some instances, described herein is an interleukin conjugate, in which the interleukin is selected from IL-1β, IL-2, IL-7, IL-10, IL-12, IL-15, IL-18, and IL-21.

IL-2 Conjugates

In some embodiments, described herein are IL-2 conjugates modified at an amino acid position. In some instances, the modification is to a natural amino acid. In some instances, the modification is to an unnatural amino acid. In some instances, described herein is an isolated and modified IL-2 polypeptide that comprises at least one unnatural amino acid. In some instances, the IL-2 polypeptide is an isolated and purified mammalian IL-2, for example, a rodent IL-2 protein, or a human IL-2 protein. In some cases, the IL-2 polypeptide is a human IL-2 protein. In some cases, the IL-2 polypeptide comprises about 80%, 85%, 90%, 95%, 96%, 97%, 98%, or 99% sequence identity to SEQ ID NO: 1. In some cases, the IL-2 polypeptide comprises the sequence of SEQ ID NO: 1. In some cases, the IL-2 polypeptide consists of the sequence of SEQ ID NO: 1. In additional cases, the IL-2 polypeptide comprises about 80%, 85%, 90%, 95%, 96%, 97%, 98%, or 99% sequence identity to SEQ ID NO: 2. In additional cases, the IL-2 polypeptide comprises the sequence of SEQ ID NO: 2. In additional cases, the IL-2 polypeptide consists of the sequence of SEQ ID NO: 2.

In some instances, the IL-2 polypeptide is a truncated variant. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the IL-2 polypeptide comprises an N-terminal deletion of at least or about 1, 2, 3, 4, 5, 6, 7, 8, 9, 10, 11, 12, 13, 14, 15, 20, or more residues. In some cases, the IL-2 polypeptide comprises an N-terminal deletion of at least or about 1, 2, 3, 4, 5, 6, 7, 8, 9, or 10 residues. In some cases, the IL-2 polypeptide comprises an N-terminal deletion of at least or about 2 residues. In some cases, the IL-2 polypeptide comprises an N-terminal deletion of at least or about 3 residues. In some cases, the IL-2 polypeptide comprises an N-terminal deletion of at least or about 4 residues. In some cases, the IL-2 polypeptide comprises an N-terminal deletion of at least or about 5 residues. In some cases, the IL-2 polypeptide comprises an N-terminal deletion of at least or about 6 residues. In some cases, the IL-2 polypeptide comprises an N-terminal deletion of at least or about 7 residues. In some cases, the IL-2 polypeptide comprises an N-terminal deletion of at least or about 8 residues. In some cases, the IL-2 polypeptide comprises an N-terminal deletion of at least or about 9 residues. In some cases, the IL-2 polypeptide comprises an N-terminal deletion of at least or about 10 residues.

In some embodiments, the IL-2 polypeptide is a functionally active fragment. In some cases, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some cases, the functionally active fragment comprises IL-2 region 10-133, wherein the residue positions are in reference to the positions in SEQ ID NO: 1. In some cases, the functionally active fragment comprises IL-2 region 20-133, wherein the residue positions are in reference to the positions in SEQ ID NO: 1. In some cases, the functionally active fragment comprises IL-2 region 30-133, wherein the residue positions are in reference to the positions in SEQ ID NO: 1. In some cases, the functionally active fragment comprises IL-2 region 10-125, wherein the residue positions are in reference to the positions in SEQ ID NO: 1. In some cases, the functionally active fragment comprises IL-2 region 20-125, wherein the residue positions are in reference to the positions in SEQ ID NO: 1. In some cases, the functionally active fragment comprises IL-2 region 1-130, wherein the residue positions are in reference to the positions in SEQ ID NO: 1. In some cases, the functionally active fragment comprises IL-2 region 1-125, wherein the residue positions are in reference to the positions in SEQ ID NO: 1.

In some embodiments, described herein is an IL-2 conjugate that comprises an isolated, purified, and modified IL-2 polypeptide and a conjugating moiety. In some instances, the IL-2 conjugate has a decreased affinity to an IL-2 receptor α (IL-2Rα) subunit relative to a wild-type IL-2 polypeptide. In some cases, the conjugating moiety is bound to an amino acid residue that interacts with IL-2Rα (e.g., at the IL-2/IL-2Rα interface). In some cases, the conjugating moiety is bound to an amino acid residue that is proximal to the IL-2/IL-2Rα interface (e.g., about 5 Å, about 10 Å, about 15 Å, or about 20 Å away from the IL-2/IL-2Rα interface). As used herein, the residues involved in the IL-2/IL-2Rα interface comprise IL-2 residues that form hydrophobic interactions, hydrogen bonds, or ionic interactions with residues from the IL-2Rα subunit.

In some instances, the conjugating moiety is bound to an amino acid residue selected from an amino acid position Y31, K32, N33, P34, K35, T37, R38, T41, F42, K43, F44, Y45, P47, K48, Q57, E60, E61, E62, L63, K64, P65, E68, V69, N71, L72, Q74, S75, K76, N77, M104, C105, E106, Y107, A108, D109, E110, T111, or A112, in which the numbering of the amino acid residues corresponds to SEQ ID NO: 1. In some instances, the amino acid position is selected from Y31, K32, N33, P34, K35, T37, R38, T41, F42, K43, F44, Y45, P47, K48, E61, E62, E68, K64, P65, V69, L72, Q74, S75, K76, N77, M104, C105, E106, Y107, A108, D109, E110, T111, and A112. In some instances, the amino acid position is selected from N33, P34, K35, T37, R38, M39, T41, F42, K43, F44, Y45, Q57, E60, E61, E62, L63, K64, P65, E68, V69, N71, L72, M104, C105, E106, Y107, A108, D109, E110, T111, and A112. In some instances, the amino acid position is selected from K35, T37, R38, T41, F42, K43, F44, Y45, E61, E62, E68, K64, P65, V69, L72, and Y107. In some instances, the amino acid position is selected from T37, R38, T41, F42, F44, Y45, E61, E62, E68, K64, P65, V69, L72, and Y107. In some instances, the amino acid position is selected from T37, R38, T41, F42, F44, Y45, E61, E62, E68, P65, V69, L72, and Y107. In some instances, the amino acid position is selected from T37, T41, F42, F44, Y45, P65, V69, L72, and Y107. In some instances, the amino acid position is selected from R38 and K64. In some instances, the amino acid position is selected from E61, E62, and E68. In some cases, the amino acid position is at K35. In some cases, the amino acid position is at T37. In some cases, the amino acid position is at R38. In some cases, the amino acid position is at T41. In some cases, the amino acid position is at F42. In some cases, the amino acid position is at K43. In some cases, the amino acid position is at F44. In some cases, the amino acid position is at Y45. In some cases, the amino acid position is at E61. In some cases, the amino acid position is at E62. In some cases, the amino acid position is at K64. In some cases, the amino acid position is at E68. In some cases, the amino acid position is at P65. In some cases, the amino acid position is at V69. In some cases, the amino acid position is at L72. In some cases, the amino acid position is at Y107. In some cases, the amino acid position is at L72. In some cases, the amino acid position is at D109.

In some instances, the IL-2 conjugate further comprises an additional mutation. In some cases, the additional mutation is at an amino acid position selected from K35, T37, R38, T41, F42, K43, F44, Y45, E61, E62, E68, K64, P65, V69, L72, and Y107. In such cases, the amino acid is conjugated to an additional conjugating moiety for increase in serum half-life, stability, or a combination thereof. Alternatively, the amino acid is first mutated to a natural amino acid such as lysine, cysteine, histidine, arginine, aspartic acid, glutamic acid, serine, threonine, or tyrosine; or to an unnatural amino acid prior to binding to the additional conjugating moiety.

In some embodiments, the decreased affinity of the modified IL-2 polypeptide to an IL-2 receptor α (IL-2Rα) subunit relative to a wild-type IL-2 polypeptide without the unnatural amino acid modification (e.g., a wild-type IL-2 polypeptide) is about 10%, 20%, 30%, 40%, 50%, 60%, 70%, 80%, 90%, 95%, or 99%, or greater than 99%. In some cases, the decreased affinity is about 10%. In some cases, the decreased affinity is about 20%. In some cases, the decreased affinity is about 40%. In some cases, the decreased affinity is about 50%. In some cases, the decreased affinity is about 60%. In some cases, the decreased affinity is about 80%. In some cases, the decreased affinity is about 90%. In some cases, the decreased affinity is about 99%. In some cases, the decreased affinity is greater than 99%. In some cases, the decreased affinity is about 80%. In some cases, the decreased affinity is about 100%.

In some embodiments, the decreased affinity of the modified IL-2 polypeptide to an IL-2 receptor α (IL-2Rα) subunit relative to an equivalent IL-2 polypeptide without the unnatural amino acid modification (e.g., a wild-type IL-2 polypeptide) is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more. In some cases, the decreased affinity is about 1-fold. In some cases, the decreased affinity is about 2-fold. In some cases, the decreased affinity is about 4-fold. In some cases, the decreased affinity is about 5-fold. In some cases, the decreased affinity is about 6-fold. In some cases, the decreased affinity is about 8-fold. In some cases, the decreased affinity is about 10-fold. In some cases, the decreased affinity is about 30-fold. In some cases, the decreased affinity is about 50-fold. In some cases, the decreased affinity is about 100-fold. In some cases, the decreased affinity is about 300-fold. In some cases, the decreased affinity is about 500-fold. In some cases, the decreased affinity is about 1000-fold. In some cases, the decreased affinity is more than 1,000-fold.

In some cases, the modified IL-2 polypeptide does not interact with IL-2Rα. In some instances, the modified IL-2 polypeptide is further conjugated to a conjugating moiety. In some cases, the IL-2 conjugate does not interact with IL-2Rα.

In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 5-fold. In some instances, the difference is less than 9-fold, less than 8-fold, less than 7-fold, less than 6-fold, less than 5-fold, less than 4-fold, less than 3-fold, less than 2-fold, or less than 1-fold. In some instances, the modified IL-2 polypeptide is a partial agonist, e.g., an agonist that activates a receptor (e.g., an IL-2βγ signaling complex or an IL-2αβγ signaling complex) but has only a partial efficacy at the receptor relative to a full agonist. In some instances, the modified IL-2 polypeptide is a full agonist, e.g., an agonist that activates a receptor (e.g., an IL-2βγ signaling complex or an IL-2αβγ signaling complex) at a maximum response.

In some instances, the receptor signaling potency is measured by an EC50 value. In some instances, the modified IL-2 polypeptide provides a first EC50 value for activating IL-2βγ signaling complex and a second EC50 value for activating IL-2αβγ signaling complex, and wherein a difference between the first EC50 and the second EC50 value is less than 10-fold. In some instances, the modified IL-2 polypeptide provides a first EC50 value for activating IL-2βγ signaling complex and a second EC50 value for activating IL-2αβγ signaling complex, and wherein a difference between the first EC50 and the second EC50 value is less than 5-fold. In some cases, the difference is less than 9-fold, less than 8-fold, less than 7-fold, less than 6-fold, less than 5-fold, less than 4-fold, less than 3-fold, less than 2-fold, or less than 1-fold.

In some instances, the receptor signaling potency is measured by an ED50 value. In some instances, the modified IL-2 polypeptide provides a first ED50 value for activating IL-2βγ signaling complex and a second ED50 value for activating IL-2αβγ signaling complex, and wherein a difference between the first ED50 and the second ED50 value is less than 10-fold. In some instances, the modified IL-2 polypeptide provides a first ED50 value for activating IL-2βγ signaling complex and a second ED50 value for activating IL-2αβγ signaling complex, and wherein a difference between the first ED50 and the second ED50 value is less than 5-fold. In some cases, the difference is less than 9-fold, less than 8-fold, less than 7-fold, less than 6-fold, less than 5-fold, less than 4-fold, less than 3-fold, less than 2-fold, or less than 1-fold.

In some embodiments, the conjugating moiety is linked to the N-terminus or the C-terminus of an IL-2 polypeptide, either directly or indirectly through a linker peptide. In some cases, the conjugating moiety (e.g., a polymer, a protein, or a peptide) is genetically fused to the IL-2, at the N-terminus or the C-terminus of IL-2, and either directly or indirectly through a linker peptide. In some instances, the conjugating moiety is linked to the N-terminus or the C-terminus amino acid residue. In some instances, the conjugating moiety is linked to a reactive group that is bound to the N-terminus or C-terminus amino acid residue.

In some embodiments, the IL-2 conjugate with reduced binding affinity to IL-2Rα is capable of expanding CD4+ helper cell, CD8+ effector naïve and memory T cell, Natural Killer (NK) cell, or Natural killer T (NKT) cell populations. In some cases, the conjugating moiety impairs or blocks binding of IL-2 with IL-2Rα.

In some cases, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some instances, the activation by the modified IL-2 polypeptide is equivalent to that of the wild-type IL-2 polypeptide. In other instances, the activation by the modified IL-2 polypeptide is higher than that of the wild-type IL-2 polypeptide. In some cases, the receptor signaling potency of the modified IL-2 polypeptide to the IL-2Rβγ complex is higher than a receptor signaling potency of the wild-type IL-2 polypeptide to the IL-2Rβγ complex. In some cases, the receptor signaling potency of the modified IL-2 polypeptide is at least 1-fold higher than the respective potency of the wild-type IL-2 polypeptide. In some cases, the receptor signaling potency of the modified IL-2 polypeptide is about or at least 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 60-fold, 70-fold, 80-fold, 90-fold, 100-fold, 150-fold, 200-fold, 300-fold, 400-fold, 500-fold, 1,000-fold, or higher than the respective potency of the wild-type IL-2 polypeptide. In such cases, the dose or concentration of the modified IL-2 polypeptide used for achieving a similar level of activation of the CD4+ helper cell, CD8+ effector naïve and memory cell, Natural Killer (NK) cell, or Natural killer T (NKT) cell population as a wild-type IL-2 polypeptide is lower than a dose or concentration used for the wild-type IL-2 polypeptide.

In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population by a wild-type IL-2 polypeptide. In some cases, the receptor signaling potency of the modified IL-2 polypeptide the IL-2Rβγ complex is lower than a receptor signaling potency of the wild-type IL-2 polypeptide the IL-2Rβγ complex. In some cases, the receptor signaling potency of the modified IL-2 polypeptide is about or at least 1-fold, 2-fold, 3-fold, 4-fold, 5-fold, 10-fold, 20-fold, or 50-fold lower than the respective potency of the wild-type IL-2 polypeptide.

In some embodiments, the modified IL-2 polypeptide exhibits a first receptor signaling potency to IL-2Rβγ and a second receptor signaling potency to IL-2Rαβγ. In some instances, the first receptor signaling potency to IL-2Rβγ is an improved potency relative to a wild-type IL-2 polypeptide. In some instances, the second receptor signaling potency to IL-2Rαβγ is an impaired potency relative to the wild-type IL-2 polypeptide. In some embodiments, the modified IL-2 polypeptide exhibits a first receptor signaling potency to IL-2Rβγ and a second receptor signaling potency to IL-2Rαγβ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or higher than the second receptor signaling potency. In some instances, the first receptor signaling potency is at least 1-fold or higher than the second receptor signaling potency. In some instances, the first receptor signaling potency is at least 2-fold or higher than the second receptor signaling potency. In some instances, the first receptor signaling potency is at least 5-fold or higher than the second receptor signaling potency. In some instances, the first receptor signaling potency is at least 10-fold or higher than the second receptor signaling potency. In some instances, the first receptor signaling potency is at least 20-fold or higher than the second receptor signaling potency. In some instances, the first receptor signaling potency is at least 50-fold or higher than the second receptor signaling potency. In some instances, the first receptor signaling potency is at least 100-fold or higher than the second receptor signaling potency. In some instances, the first receptor signaling potency is at least 500-fold or higher than the second receptor signaling potency. In some instances, the first receptor signaling potency is at least 1000-fold or higher than the second receptor signaling potency. In some instances, the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some cases, both receptor signaling potencies are lower than their respective potencies in a wild-type IL-2 polypeptide. In other cases, both receptor signaling potencies are higher than their respective potencies in a wild-type IL-2 polypeptide.

In some embodiments, the IL-2 conjugate decreases a toxic adverse event in a subject administered with the IL-2 conjugate. Exemplary toxic adverse events include eosinophilia, capillary leak, and vascular leak syndrome (VLS). In some instances, the IL-2 conjugate decreases the occurrence of a toxic adverse event in the subject by about 10%, 20%, 30%, 40%, 50%, 60%, 70%, 80%, 90%, 95%, 99%, or about 100%, relative to a second subject administered with a wild-type IL-2 or aldesleukin. In some instances, the IL-2 conjugate decreases the severity of a toxic adverse event in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is eosinophilia. In some cases, the IL-2 conjugate decreases the occurrence of eosinophilia in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of eosinophilia in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is capillary leak. In some cases, the IL-2 conjugate decreases the occurrence of capillary leak in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of capillary leak in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is VLS. In some cases, the IL-2 conjugate decreases the occurrence of VLS in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of VLS in the subject by about 10%, 20%, 30%, 40%, 50%, 60%, 70%, 80%, 90%, 95%, 99%, or about 100%, relative to a second subject administered with a wild-type IL-2 or aldesleukin.

In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, or more. In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, or more. In some embodiments, the IL-2 conjugate comprises a plasma half-life of greater than 1 hour. In some embodiments, the IL-2 conjugate comprises a plasma half-life of greater than 2 hours. In some embodiments, the IL-2 conjugate comprises a plasma half-life of greater than 3 hours. In some embodiments, the IL-2 conjugate comprises a plasma half-life of greater than 4 hours. In some embodiments, the IL-2 conjugate comprises a plasma half-life of greater than 5 hours. In some embodiments, the IL-2 conjugate comprises a plasma half-life of greater than 6 hours. In some embodiments, the IL-2 conjugate comprises a plasma half-life of greater than 7 hours. In some embodiments, the IL-2 conjugate comprises a plasma half-life of greater than 8 hours. In some embodiments, the IL-2 conjugate comprises a plasma half-life of greater than 9 hours. In some embodiments, the IL-2 conjugate comprises a plasma half-life of greater than 10 hours. In some embodiments, the IL-2 conjugate comprises a plasma half-life of greater than 12 hours. In some embodiments, the IL-2 conjugate comprises a plasma half-life of greater than 18 hours. In some embodiments, the IL-2 conjugate comprises a plasma half-life of greater than 24 hours.

In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some embodiments, the IL-2 conjugate comprises a plasma half-life of at least 1 hour. In some embodiments, the IL-2 conjugate comprises a plasma half-life of at least 2 hours. In some embodiments, the IL-2 conjugate comprises a plasma half-life of at least 3 hours. In some embodiments, the IL-2 conjugate comprises a plasma half-life of at least 4 hours. In some embodiments, the IL-2 conjugate comprises a plasma half-life of at least 5 hours. In some embodiments, the IL-2 conjugate comprises a plasma half-life of at least 6 hours. In some embodiments, the IL-2 conjugate comprises a plasma half-life of at least 7 hours. In some embodiments, the IL-2 conjugate comprises a plasma half-life of at least 8 hours. In some embodiments, the IL-2 conjugate comprises a plasma half-life of at least 9 hours. In some embodiments, the IL-2 conjugate comprises a plasma half-life of at least 10 hours. In some embodiments, the IL-2 conjugate comprises a plasma half-life of at least 12 hours. In some embodiments, the IL-2 conjugate comprises a plasma half-life of at least 18 hours. In some embodiments, the IL-2 conjugate comprises a plasma half-life of at least 24 hours.

In some embodiments, the IL-2 conjugate comprises a plasma half-life of from about 1 hour to about 7 days, from about 12 hours to about 7 days, from about 18 hours to about 7 days, from about 24 hours to about 7 days, from about 1 hours to about 5 days, from about 12 hours to about 5 days, from about 24 hours to about 5 days, from about 2 days to about 5 days, or from about 2 days to about 3 days.

In some embodiments, the IL-2 conjugate comprises a plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours.

In some embodiments, the IL-2 conjugate comprises a plasma half-life that is capable of proliferating and/or expanding a CD4+ helper cell, CD8+ effector naïve and memory T cell, NK cell, NKT cell, or a combination thereof, but does not exert a deleterious effect such as apoptosis.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to a wild-type IL-2. In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, or more relative to a wild-type IL-2.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to a wild-type IL-2.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to aldesleukin. In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, or more relative to aldesleukin.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to aldesleukin.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to a wild-type IL2. In some cases, the reduced toxicity is at least 10%, 20%, 30%, 40%, 50%, 60%, 70%, 80%, 90%, 100%, 200%, 300%, 400%, 500%, or more reduced relative to a wild-type IL-2.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to aldesleukin. In some cases, the reduced toxicity is at least 10%, 20%, 30%, 40%, 50%, 60%, 70%, 80%, 90%, 100%, 200%, 300%, 400%, 500%, or more reduced relative to aldesleukin.

In some embodiments, the IL-2 conjugate comprises a conjugating moiety in which the size (e.g., the volume or length) of the conjugating moiety enhances plasma stability but does not reduce potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety reduces the potency by less than 5%, 4%, 3%, 2%, 1%, or less relative to aldesleukin.

In some embodiments, the IL-2 conjugate comprises a conjugating moiety in which the size (e.g., the volume or length) of the conjugating moiety enhances plasma stability and potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety further enhances the potency by more than 5%, 10%, 20%, 30%, 40%, 50%, 60%, 70%, 80%, 90%, 100%, 200%, or more relative to aldesleukin.

In some embodiments, described herein is an IL-2 conjugate comprising an unnatural amino acid covalently attached to a conjugating moiety, wherein the unnatural amino acid is located in region 35-107, and wherein the region 35-107 corresponds to residues K35-Y107 of SEQ ID NO: 1.

In some embodiments, described herein is an interleukin 2 βγ receptor (IL-2Rβγ) binding protein, wherein the binding affinity for an interleukin 2 α receptor (IL-2Rα) of said binding protein is less than that of wild-type human IL-2 (hIL-2), wherein the binding affinity for an interleukin 2 α receptor (IL-2Rα) of said binding protein is less than that of wild-type human IL-2 (hIL-2). In some embodiments, described herein is an interleukin 2 βγ receptor (IL-2Rβγ) binding protein, wherein the binding affinity for an interleukin 2 α receptor (IL-2Rα) of said binding protein is less than that of wild-type human IL-2 (hIL-2), and wherein said binding protein comprises at least one unnatural amino acid. In some instances, said binding protein is a modified IL-2 polypeptide or a functionally active fragment thereof, wherein the modified IL-2 polypeptide comprises at least one unnatural amino acid. In some instances, the at least one unnatural amino acid is located in region 35-107, and wherein the region 35-107 corresponds to residues K35-Y107 of SEQ ID NO: 1.

In some embodiments, described herein is an IL-2/IL-2Rβγ complex comprising a modified IL-2 polypeptide comprising a mutation and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some instances, the modified IL-2 polypeptide further comprises a conjugating moiety covalently attached to site of mutation. In some instances, the site of mutation comprises an amino acid mutated to a natural amino acid. In some cases, the site of mutation comprises an amino acid mutated to a cysteine residue. In other cases, the site of mutation comprises an amino acid mutated to a lysine residue.

In some embodiments, described herein is an IL-2/IL-2Rβγ complex comprising a modified IL-2 polypeptide comprising an unnatural amino acid and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some instances, the modified IL-2 polypeptide further comprises a conjugating moiety covalently attached to the unnatural amino acid.

In some embodiments, described herein is an IL-2/IL-2Rβγ complex comprising a modified IL-2 polypeptide comprising an unnatural amino acid and an IL-2Rβγ, wherein the modified IL-2 polypeptide has a reduced receptor signaling potency toward IL-2Rα, and wherein the reduced receptor signaling potency is compared to a receptor signaling potency between a wild-type IL-2 polypeptide and IL-2Rα. In some instances, the modified IL-2 polypeptide further comprises a conjugating moiety covalently attached to the unnatural amino acid.

In some embodiments, described herein is an activator of a CD4+ helper cell, CD8+ effector naïve and memory T cell, Natural Killer (NK) cell, or a Natural killer T (NKT) cell that selectively expands CD4+ helper cells, CD8+ effector naïve and memory T cells, NK cells, NKT cells, or a combination thereof in a cell population, wherein said activator comprises a modified interleukin 2 (IL-2) polypeptide comprising at least one mutation. In some instances, the mutation is to a natural amino acid. In other instances, the mutation is to an unnatural amino acid. In some embodiments, described herein is an activator of a CD4+ helper cell, CD8+ effector naïve and memory T cell, Natural Killer (NK) cell, or a Natural killer T (NKT) cell that selectively expands CD4+ helper cells, CD8+ effector naïve and memory T cells, NK cells, NKT cells, or a combination thereof in a cell population, wherein said activator comprises a modified interleukin 2 (IL-2) polypeptide comprising at least one unnatural amino acid. In some instances, said activator expands CD4+ T regulatory (Treg) cells by less than 20%, 15%, 10%, 5%, 1%, or less than 0.1% when said activator is in contact with said CD3+ cell population compared to an expansion of CD4+ Treg cells in the CD3+ cell population contacted with a wild-type IL-2 polypeptide. In some instances, said activator does not expand Treg cells in said cell population. In some instances, said cell population is an in vivo cell population. In some instances, said cell population is an in vitro cell population. In some instances, said cell population is an ex vivo cell population.

In some instances, also described herein is a method of expanding a CD4+ helper cell, CD8+ effector naïve and memory T cell, Natural Killer (NK) cell, or a Natural killer T (NKT) cell population, comprising contacting said cell population with a therapeutically effective amount of a CD4+ helper cell, CD8+ effector naïve and memory T cell, Natural Killer (NK) cell, or a Natural killer T (NKT) cell activator, in which said activator comprises a modified interleukin 2 (IL-2) polypeptide comprising at least one mutation, thereby expanding the CD4+ helper cell, CD8+ effector naïve and memory T cell, Natural Killer (NK) cell, or Natural killer T (NKT) cell population. In some instances, the mutation is to a natural amino acid. In other instances, the mutation is to an unnatural amino acid. In some instances, also described herein is a method of expanding a CD4+ helper cell, CD8+ effector naïve and memory T cell, Natural Killer (NK) cell, or a Natural killer T (NKT) cell population, comprising contacting said cell population with a therapeutically effective amount of a CD4+ helper cell, CD8+ effector naïve and memory T cell, Natural Killer (NK) cell, or a Natural killer T (NKT) cell activator, in which said activator comprises a modified interleukin 2 (IL-2) polypeptide comprising at least one unnatural amino acid, thereby expanding the CD4+ helper cell, CD8+ effector naïve and memory T cell, Natural Killer (NK) cell, or Natural killer T (NKT) cell population.

IL-15 Conjugates

In some embodiments, described herein are IL-15 conjugates modified at an amino acid position. IL-15 regulates activation and proliferation of T cells and NK cells. In some instances, the IL-15 conjugate comprises an isolated and purified IL-15 polypeptide and a conjugating moiety. In some instances, the IL-15 conjugate has a decreased affinity to an IL-15 receptor relative to a wild-type IL-15 polypeptide. In some cases, the conjugating moiety is bound to an amino acid residue that interacts with the IL-15 receptor (e.g., at an IL-15/IL-15Rα interface) or with IL-2Rβγ subunits. In some cases, the conjugating moiety is bound to an amino acid residue that is proximal to the IL-15/IL-15Rα interface (e.g., about 5 Å, about 10 Å, about 15 Å, or about 20 Å away from the IL-15/IL-15Rα interface) or proximal to the IL-2Rβγ subunits. As used herein, the residues involved in the IL-15/IL-15R interface comprise IL-15 residues that form hydrophobic interactions, hydrogen bonds, or ionic interactions with residues from the IL-15R. Similarly, residues involved in the IL-15/IL-2Rβγ interface comprises IL-15 residues that form hydrophobic interactions, hydrogen bonds, or ionic interactions with residues from the IL-2Rβγ subunits. In some cases, the conjugating moiety is linked to the N-terminus or the C-terminus of the IL-15 polypeptide (e.g., to the N-terminus or C-terminus amino acid residue or to a reactive group bound to the terminal amino acid residue), either directly or indirectly through a linker peptide. In additional cases, the conjugating moiety modulates the interaction between IL-15 and IL-15R. In some instances, the IL-15 conjugate upregulates distinct population(s) of tumor infiltrating lymphocytes through IL-15/IL-15R signaling. In some instances, the IL-15 conjugate promotes a decrease in the proliferation and/or expansion of tumor associated lymphocytes. In some instances, the IL-15 conjugate modulates immune activity.

Additional Cytokine Conjugates

In some embodiments, described herein include one or more additional cytokine conjugates modified at an amino acid position. Exemplary cytokines include, but are not limited to, IL-1β, IL-7, IL-10, IL-12, IL-18, IL-21, an INF (e.g., IFN-α, IFN-β, IFN-κ, IFN-δ, IFN-ε, IFN-τ, or IFN-ω, or IFN-ζ), and a TNF (e.g., TNFα or CD40L). In some instances, the cytokine conjugate comprises an isolated and purified cytokine polypeptide and a conjugating moiety. In some instances, the cytokine conjugate has a decreased affinity to its respective receptor relative to its wild-type cytokine. In some cases, the conjugating moiety is bound to an amino acid residue that is proximal to the receptor interface (e.g., about 5 Å, about 10 Å, about 15 Å, or about 20 Å away from the receptor interface). In some cases, the conjugating moiety is linked to the N-terminus or the C-terminus of the cytokine, either directly or indirectly through a linker peptide. In additional cases, the conjugating moiety modulates the interaction between cytokine and its respective receptor. In some instances, the cytokine conjugate upregulates distinct population(s) of tumor infiltrating lymphocytes. In some instances, the cytokine conjugate promotes a decrease in the proliferation and/or expansion of tumor associated lymphocytes. In some instances, the cytokine conjugate modulates immune activity.

Cytokines Conjugate Precursors

Described herein are cytokine conjugate precursors, comprising a mutant cytokine (such as IL-2), wherein one or more amino acids have been mutated from the wild type amino acid. Such precursors are often used with the methods described herein for the treatment of diseases or conditions. In some embodiments, a cytokine precursor is not conjugated. Such mutations variously comprise additions, deletions, or substitutions. In some embodiments, the mutation comprises substitution to a different natural amino acid. In some instances, the mutant cytokine comprises a mutation at amino acid position Y31, K32, N33, P34, K35, T37, R38, T41, F42, K43, F44, Y45, P47, K48, Q57, E60, E61, E62, L63, K64, P65, E68, V69, N71, L72, Q74, S75, K76, N77, M104, C105, E106, Y107, A108, D109, E110, T111, or A112, in which the numbering of the amino acid residues corresponds to SEQ ID NO: 1. In some instances, the amino acid position is selected from Y31, K32, N33, P34, K35, T37, R38, T41, F42, K43, F44, Y45, P47, K48, E61, E62, E68, K64, P65, V69, L72, Q74, S75, K76, N77, M104, C105, E106, Y107, A108, D109, E110, T111, and A112. In some instances, the amino acid position is selected from N33, P34, K35, T37, R38, M39, T41, F42, K43, F44, Y45, Q57, E60, E61, E62, L63, K64, P65, E68, V69, N71, L72, M104, C105, E106, Y107, A108, D109, E110, T111, and A112. In some instances, the amino acid position is selected from K35, T37, R38, T41, F42, K43, F44, Y45, E61, E62, E68, K64, P65, V69, L72, and Y107. In some instances, the amino acid position is selected from T37, R38, T41, F42, F44, Y45, E61, E62, E68, K64, P65, V69, L72, and Y107. In some instances, the amino acid position is selected from T37, R38, T41, F42, F44, Y45, E61, E62, E68, P65, V69, L72, and Y107. In some instances, the amino acid position is selected from T37, T41, F42, F44, Y45, P65, V69, L72, and Y107. In some instances, the amino acid position is selected from R38 and K64. In some instances, the amino acid position is selected from E61, E62, and E68. In some cases, the amino acid position is at K35. In some cases, the amino acid position is at T37. In some cases, the amino acid position is at R38. In some cases, the amino acid position is at T41. In some cases, the amino acid position is at F42. In some cases, the amino acid position is at K43. In some cases, the amino acid position is at F44. In some cases, the amino acid position is at Y45. In some cases, the amino acid position is at E61. In some cases, the amino acid position is at E62. In some cases, the amino acid position is at K64. In some cases, the amino acid position is at E68. In some cases, the amino acid position is at P65. In some cases, the amino acid position is at V69. In some cases, the amino acid position is at L72. In some cases, the amino acid position is at Y107. In some cases, the amino acid position is at L72. In some cases, the amino acid position is at D109. In some embodiments, a cytokine mutant comprises a conjugation moiety, wherein the conjugation moiety is attached to a mutated site in the mutant cytokine.

Cytokine mutants described herein often comprise one or more mutations to natural amino acids. In some embodiments, a cytokine mutant comprises SEQ ID NO:1, and at least one mutation. In some embodiments, the cytokine mutant comprises SEQ ID NO:1 and an E62K mutation. In some embodiments, the cytokine mutant comprises SEQ ID NO:1 and an E62C mutation. In some embodiments, the cytokine mutant comprises SEQ ID NO:1 and an E62A mutation. In some embodiments, the cytokine mutant comprises SEQ ID NO:1 and an E62I mutation. In some embodiments, the cytokine mutant comprises SEQ ID NO:1 and an E62L mutation. In some embodiments, the cytokine mutant comprises SEQ ID NO:1 and an E62Y mutation. In some embodiments, the cytokine mutant comprises SEQ ID NO:1 and an E62W mutation. In some embodiments, the cytokine mutant comprises SEQ ID NO:1 and an E62N mutation. In some embodiments, the cytokine mutant comprises SEQ ID NO:1 and an E62R mutation. In some embodiments, the cytokine mutant comprises SEQ ID NO:1 and an E62D mutation. In some embodiments, the cytokine mutant comprises SEQ ID NO:1 and an E62Q mutation. In some embodiments, the cytokine mutant comprises SEQ ID NO:1 and an E62G mutation. In some embodiments, the cytokine mutant comprises SEQ ID NO:1 and an E62H mutation. In some embodiments, the cytokine mutant comprises SEQ ID NO:1 and an E62M mutation. In some embodiments, the cytokine mutant comprises SEQ ID NO:1 and an E62F mutation. In some embodiments, the cytokine mutant comprises SEQ ID NO:1 and an E62P mutation. In some embodiments, the cytokine mutant comprises SEQ ID NO:1 and an E62S mutation. In some embodiments, the cytokine mutant comprises SEQ ID NO:1 and an E62T mutation. In some embodiments, the cytokine mutant comprises SEQ ID NO:1 and an E62V mutation.

In some embodiments, a cytokine mutant comprises SEQ ID NO:1, and at least one mutation. In some embodiments, the cytokine mutant comprises SEQ ID NO:1 and a P65K mutation. In some embodiments, the cytokine mutant comprises SEQ ID NO:1 and a P65C mutation. In some embodiments, the cytokine mutant comprises SEQ ID NO:1 and a P65A mutation. In some embodiments, the cytokine mutant comprises SEQ ID NO:1 and a P65I mutation. In some embodiments, the cytokine mutant comprises SEQ ID NO:1 and a P65L mutation. In some embodiments, the cytokine mutant comprises SEQ ID NO:1 and a P65Y mutation. In some embodiments, the cytokine mutant comprises SEQ ID NO:1 and a P65W mutation. In some embodiments, the cytokine mutant comprises SEQ ID NO:1 and a P65N mutation. In some embodiments, the cytokine mutant comprises SEQ ID NO:1 and a P65R mutation. In some embodiments, the cytokine mutant comprises SEQ ID NO:1 and a P65D mutation. In some embodiments, the cytokine mutant comprises SEQ ID NO:1 and a P65Q mutation. In some embodiments, the cytokine mutant comprises SEQ ID NO:1 and a P65G mutation. In some embodiments, the cytokine mutant comprises SEQ ID NO:1 and a P65H mutation. In some embodiments, the cytokine mutant comprises SEQ ID NO:1 and a P65M mutation. In some embodiments, the cytokine mutant comprises SEQ ID NO:1 and a P65F mutation. In some embodiments, the cytokine mutant comprises SEQ ID NO:1 and a P65E mutation. In some embodiments, the cytokine mutant comprises SEQ ID NO:1 and a P65 S mutation. In some embodiments, the cytokine mutant comprises SEQ ID NO:1 and a P65T mutation. In some embodiments, the cytokine mutant comprises SEQ ID NO:1 and a P65V mutation.

Protein or Peptide Fusions

In some embodiments, a cytokine conjugate described herein comprises a cytokine (e.g., IL-2, or other cytokine) that is fused to a peptide or protein (fusion). In some embodiments, the peptide or protein is an antibody or antibody fragment. In some embodiments, a cytokine conjugate described herein comprises a cytokine (e.g., IL-2, or other cytokine) that is fused to an antibody, or its binding fragments thereof. In some embodiments, a cytokine described herein is fused to multiple proteins or peptides. In some embodiments, a cytokine conjugate comprises a cytokine fusion to a protein or peptide, and at least one conjugating moiety. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof Such fusion proteins in some instances are generated directly through translation. In some embodiments, fusions are generated using chemical or other enzymatic ligation method. In some embodiments, a cytokine conjugate comprises a fused peptide or protein is attached by a linker. In some embodiments, the linker is a peptide. In some embodiments, a cytokine conjugate comprises an N-terminal peptide or protein fusion. In some embodiments, a cytokine conjugate comprises a C-terminal peptide or protein fusion. In some cases, the cytokine fused to the peptide or protein is further conjugated to one or more conjugation moieties described below.

In some instances, the cytokine conjugate comprises a fusion to an scFv, bis-scFv, $(scFv)_2$, dsFv, or sdAb fusion. In some cases, the fusion comprises a scFv. In some cases, the cytokine conjugate comprises a fusion to bis-scFv. In some cases, the cytokine conjugate comprises a fusion to $(scFv)_2$. In some cases, the cytokine conjugate comprises a fusion to dsFv. In some cases, the cytokine conjugate comprises a fusion to sdAb. In some cases, the cytokine fused to the scFv, bis-scFv, $(scFv)_2$, dsFv, or sdAb is further conjugated to one or more conjugation moieties described below.

In some instances, the cytokine conjugate comprises a fusion to an Fc portion of an antibody, e.g., of IgG, IgA, IgM, IgE, or IgD. In some instances, the cytokine conjugate comprises a fusion to an Fc portion of IgG (e.g., $IgG_1$, $IgG_3$, or $IgG_4$). In some cases, the cytokine fused to the Fc portion is further conjugated to one or more conjugation moieties described below.

In some cases, a cytokine (e.g., an interleukin, IFN, or TNF) polypeptide is fused to an antibody, or its binding fragments thereof. In some cases, the cytokine polypeptide is fused to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is fused to an Fc portion of an antibody. In additional cases, the cytokine polypeptide is fused to an Fc portion of IgG (e.g., $IgG_1$, $IgG_3$, or $IgG_4$). In some cases, the cytokine fused to the antibody, or its binding fragments thereof is further conjugated to one or more conjugation moieties described below.

In some cases, an IL-2 polypeptide is fused to an antibody, or its binding fragments thereof. In some cases, the IL-2 polypeptide is fused to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is fused to an Fc portion of an antibody. In additional cases, the IL-2 polypeptide is fused to an Fc portion of IgG (e.g., $IgG_1$, $IgG_3$, or $IgG_4$). In some cases, the IL-2 polypeptide fused to the antibody, or its binding fragments thereof is further conjugated to one or more conjugation moieties described below.

Natural and Unnatural Amino Acids

In some embodiments, an amino acid residue described herein (e.g., within a cytokine such as IL-2) is mutated to lysine, cysteine, histidine, arginine, aspartic acid, glutamic acid, serine, threonine, or tyrosine prior to binding to (or reacting with) a conjugating moiety. For example, the side chain of lysine, cysteine, histidine, arginine, aspartic acid, glutamic acid, serine, threonine, or tyrosine may bind to a conjugating moiety described herein. In some instances, the amino acid residue is mutated to cysteine, lysine, or histidine. In some cases, the amino acid residue is mutated to cysteine. In some cases, the amino acid residue is mutated to lysine. In some cases, the amino acid residue is mutated to histidine. In some cases, the amino acid residue is mutated to tyrosine. In some cases, the amino acid residue is mutated to tryptophan. In some embodiments, an unnatural amino acid is not conjugated with a conjugating moiety. In some embodiments, a cytokine described herein comprises an unnatural amino acid, wherein the cytokine is conjugated to the protein, wherein the point of attachment is not the unnatural amino acid.

In some embodiments, an amino acid residue described herein (e.g., within a cytokine such as IL-2) is mutated to an unnatural amino acid prior to binding to a conjugating moiety. In some cases, the mutation to an unnatural amino acid prevents or minimizes a self-antigen response of the immune system. As used herein, the term "unnatural amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, azido-lysine (AzK), an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an $\alpha$, $\alpha$ disubstituted amino acid; a $\beta$-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling.

In some embodiments, the unnatural amino acid comprises a photoreactive group, which crosslinks, upon irradiation with, e.g., UV.

In some embodiments, the unnatural amino acid comprises a photo-caged amino acid.

In some instances, the unnatural amino acid is a para-substituted, meta-substituted, or an ortho-substituted amino acid derivative.

In some instances, the unnatural amino acid comprises p-acetyl-L-phenylalanine, p-azidomethyl-L-phenylalanine (pAMF), p-iodo-L-phenylalanine, O-methyl-L-tyrosine, p-methoxyphenylalanine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxy-phenylalanine, or 3-iodotyrosine.

In some cases, the unnatural amino acid is phenylselenocysteine.

In some instances, the unnatural amino acid is a benzophenone, ketone, iodide, methoxy, acetyl, benzoyl, or azide containing phenylalanine derivative.

In some instances, the unnatural amino acid is a benzophenone, ketone, iodide, methoxy, acetyl, benzoyl, or azide containing lysine derivative.

In some instances, the unnatural amino acid comprises an aromatic side chain.

In some instances, the unnatural amino acid does not comprise an aromatic side chain.

In some instances, the unnatural amino acid comprises an azido group.

In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics.

In some instances, the unnatural amino acid is dehydroalanine.

In some instances, the unnatural amino acid comprises an aldehyde or ketone group.

In some instances, the unnatural amino acid is a lysine derivative comprising an aldehyde or ketone group.

In some instances, the unnatural amino acid is a lysine derivative comprising one or more O, N, Se, or S atoms at the beta, gamma, or delta position. In some instances, the unnatural amino acid is a lysine derivative comprising 0, N, Se, or S atoms at the gamma position.

In some instances, the unnatural amino acid is a lysine derivative wherein the epilson N atom is replaced with an oxygen atom.

In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is a nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group.

In some instances, the unnatural amino acid comprises a transcyclocteny group.

In some instances, the unnatural amino acid comprises a norbornenyl group.

In some instances, the unnatural amino acid comprises a cyclopropenyl group.

In some instances, the unnatural amino acid comprises a diazirine group.

In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-{[(tert-butoxy)carbonyl]amino}hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-{[(benzyloxy)carbonyl]amino}hexanoic acid. In some instances, the unnatural amino acid is 2-amino-6-{[(p-iodobenzyloxy)carbonyl]amino}hexanoic acid. In some instances, the unnatural amino acid is 2-amino-6-{[(p-nitrobenzyloxy)carbonyl]amino}hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine. In some instances, the unnatural amino acid is 2-amino-6-{[(2-azidocyclopentyloxy)carbonyl]amino}hexanoic acid. In some instances, the unnatural amino acid is N6-((2-azidoethoxy)carbonyl)lysine. In some instances, the unnatural amino acid is 2-amino-6-{[(2-nitrobenzyloxy)carbonyl]amino}hexanoic acid. In some instances, the unnatural amino acid is 2-amino-6-{[(2-cyclooctynyloxy)carbonyl]amino}hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine, In some instances, the unnatural amino acid is N6-(but-2-enoyl)lysine. In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl)oxy)carbonyl)lysine. In some instances, the unnatural amino acid is N6-((bicyclo[2.2.1]hept-5-en-2-ylmethoxy)carbonyl)lysine. In some instances, the unnatural amino acid is cysteinyllysine. In some instances, the unnatural amino acid is N6-41-(6-nitrobenzo[d][1,3]dioxol-5-yl)ethoxy)carbonyl)lysine. In some instances, the unnatural amino acid is N6-((2-(3-methyl-3H-diazirin-3-yl)ethoxy)carbonyl)lysine. In some instances, the unnatural amino acid is N6-((3-(3-methyl-3H-diazirin-3-yl)propoxy)carbonyl)lysine. In some instances, the unnatural amino acid is N6-((meta nitrobenyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid.

In some embodiments, the unnatural amino acid is incorporated into the cytokine (e.g., the IL polypeptide) by a repurposed amber, opal, or ochre stop codon.

In some embodiments, the unnatural amino acid is incorporated into the cytokine (e.g., the IL polypeptide) by a 4-base codon.

In some embodiments, the unnatural amino acid is incorporated into the cytokine (e.g., the IL polypeptide) by a repurposed rare sense codon.

In some embodiments, the unnatural amino acid is incorporated into the cytokine (e.g., the IL polypeptide) by a synthetic codon comprising an unnatural nucleic acid.

In some instances, the unnatural amino acid is incorporated into the cytokine by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with a) other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the cytokine (e.g., the IL polypeptide) by an aminoacyl (aaRS or RS)-tRNA synthetase-tRNA pair. Exemplary aaRS-tRNA pairs include, but are not limited to, Methanococcus jannaschii (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine and p-methoyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronopheylalanine; and o-nitrobenzyltyrosine.

In some instances, the unnatural amino acid is incorporated into the cytokine (e.g., the IL polypeptide) by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenoe, ketone, iodide, or azide substituents; O-propargyltyrosine; α-aminocaprylic acid, O-methyl tyrosine, O-nitrobenzyl cysteine; and 3-(naphthalene-2-ylamino)-2-amino-propanoic acid.

In some instances, the unnatural amino acid is incorporated into the cytokine (e.g., the IL polypeptide) by a pyrrolysyl-tRNA pair. In some cases, the PylRS is obtained from an archaebacterial, e.g., from a methanogenic archaebacterial. In some cases, the PylRS is obtained from *Methanosarcina barkeri, Methanosarcina mazei,* or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-ε-[(1-(6-nitrobenzo[d][1,3]dioxol-5-yl)ethoxy)carbonyl]-L-lysine; and N-ε-(1-methylcyclopro-2-enecarboxamido)lysine.

In some instances, an unnatural amino acid is incorporated into a cytokine described herein (e.g., the IL polypeptide) by a synthetase disclosed in U.S. Pat. Nos. 9,988,619 and 9,938,516. Exemplary UAAs that can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, such synthetases are expressed and used to incorporate UAAs into cytokines in-vivo. In some embodiments, such synthetases are used to incorporate UAAs into cytokines using a cell-free translation system.

In some instances, an unnatural amino acid is incorporated into a cytokine described herein (e.g., the IL polypeptide) by a naturally occurring synthetase. In some embodiments, an unnatural amino acid is incorporated into a cytokine by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

In some instances, the unnatural amino acid comprises an unnatural amino acid illustrated in FIG. 1.

Figure 2A:
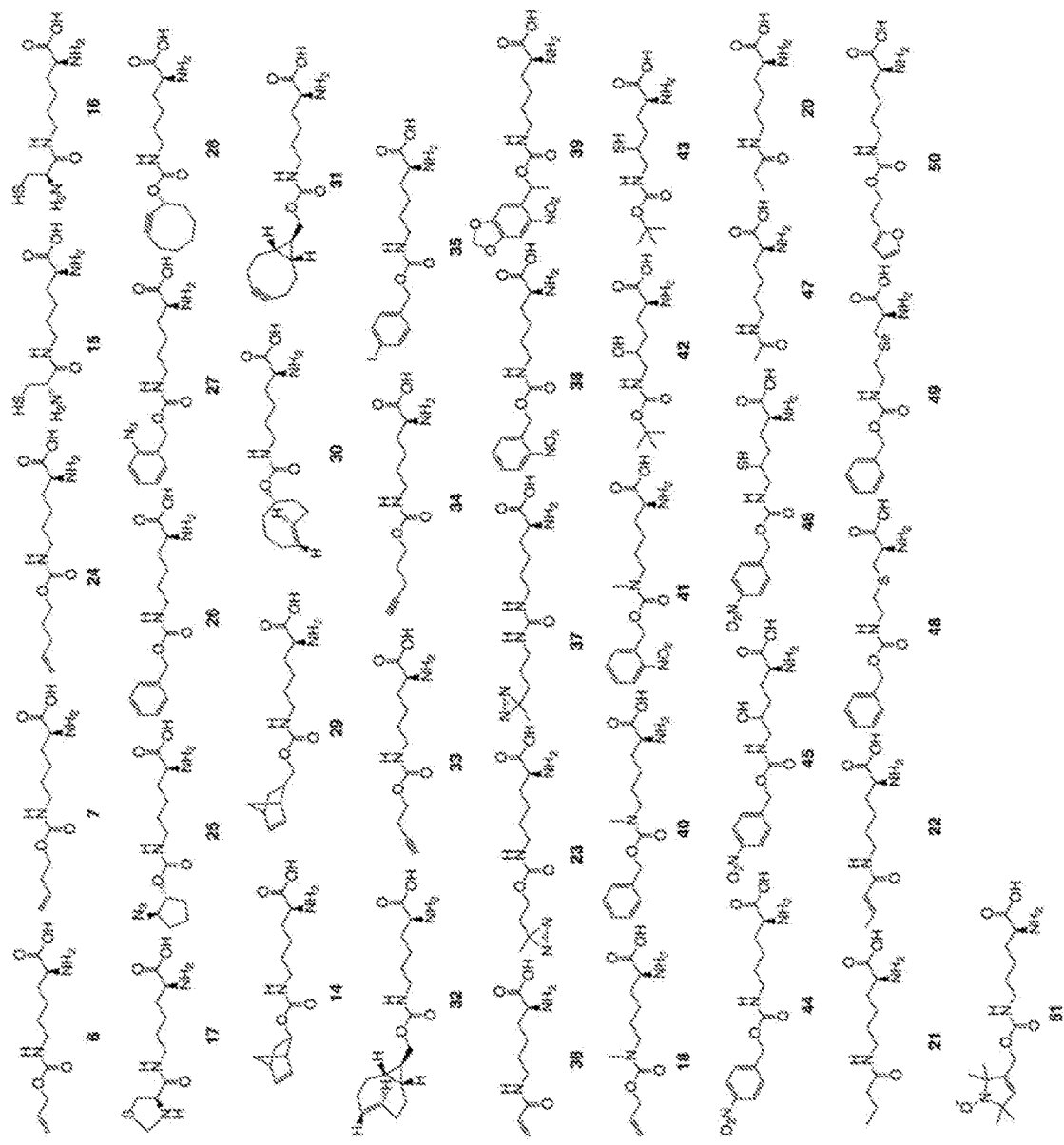
FIG. 2A-FIG. 2B illustrate exemplary unnatural amino acids.
Figure 2B:
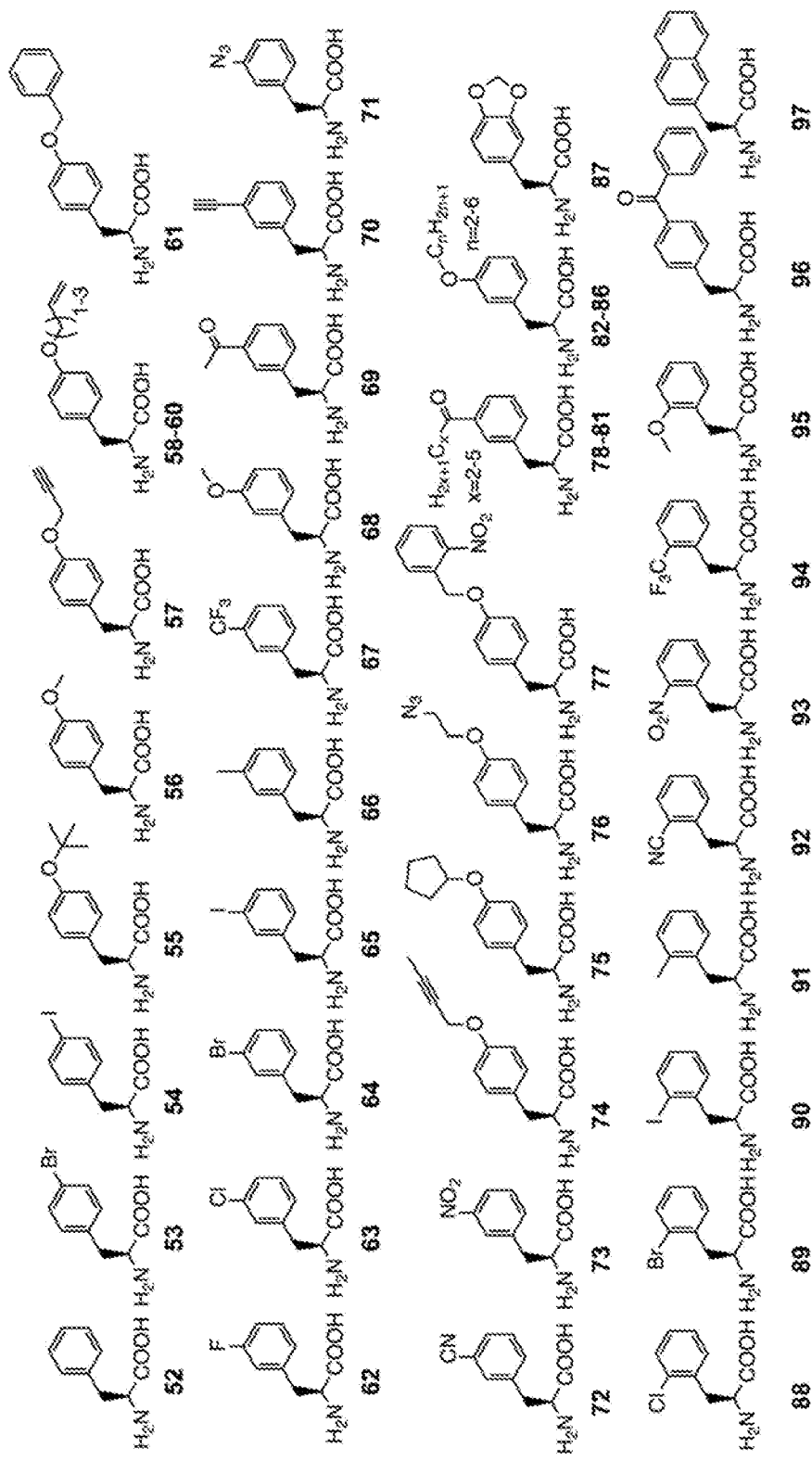
Figure 3A:
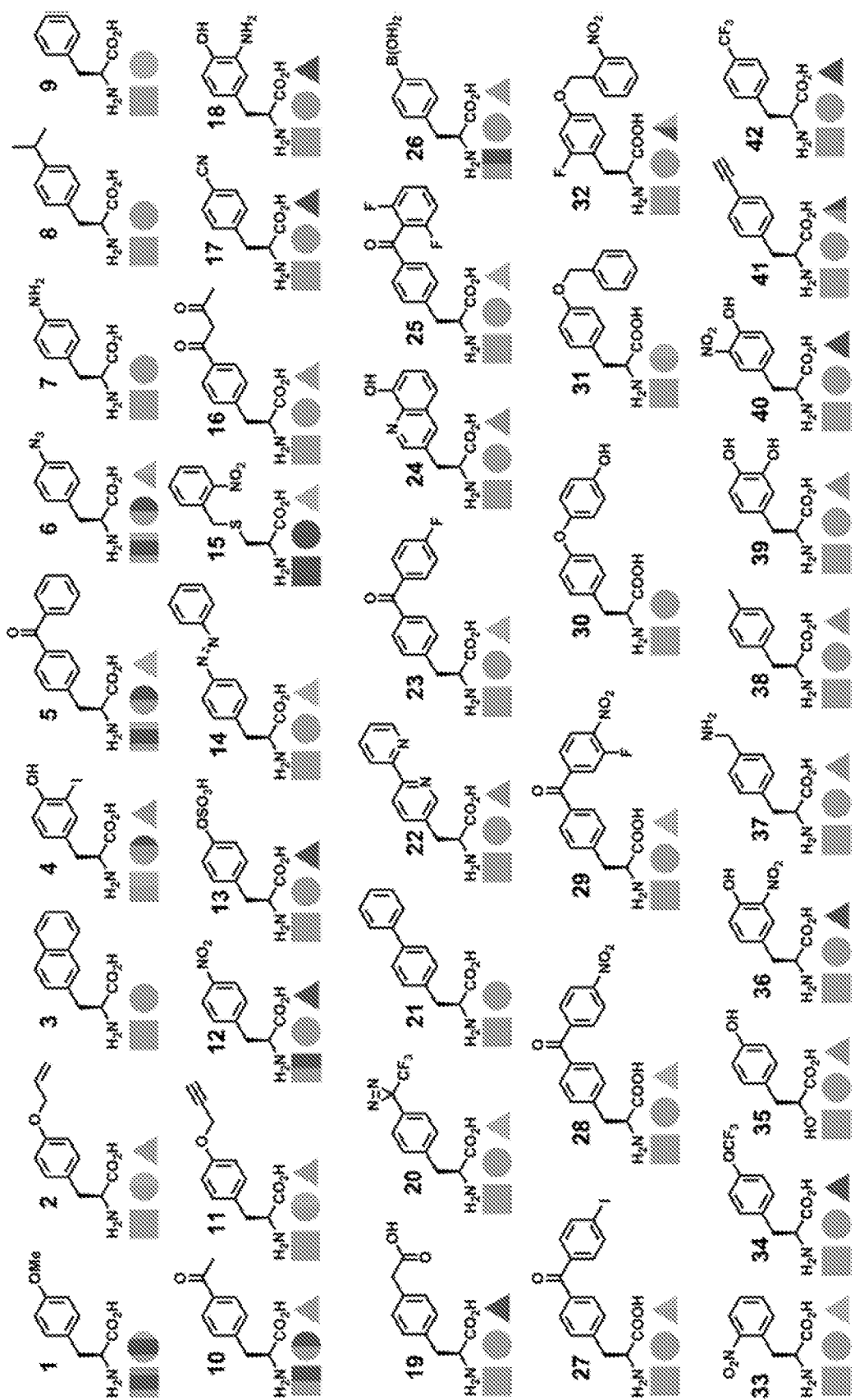
FIG. 3A-FIG. 3D illustrate exemplary unnatural amino acids. These unnatural amino acids (UAAs) have been genetically encoded in proteins (FIG. 3A—UAA #1-42.
Figure 3B:
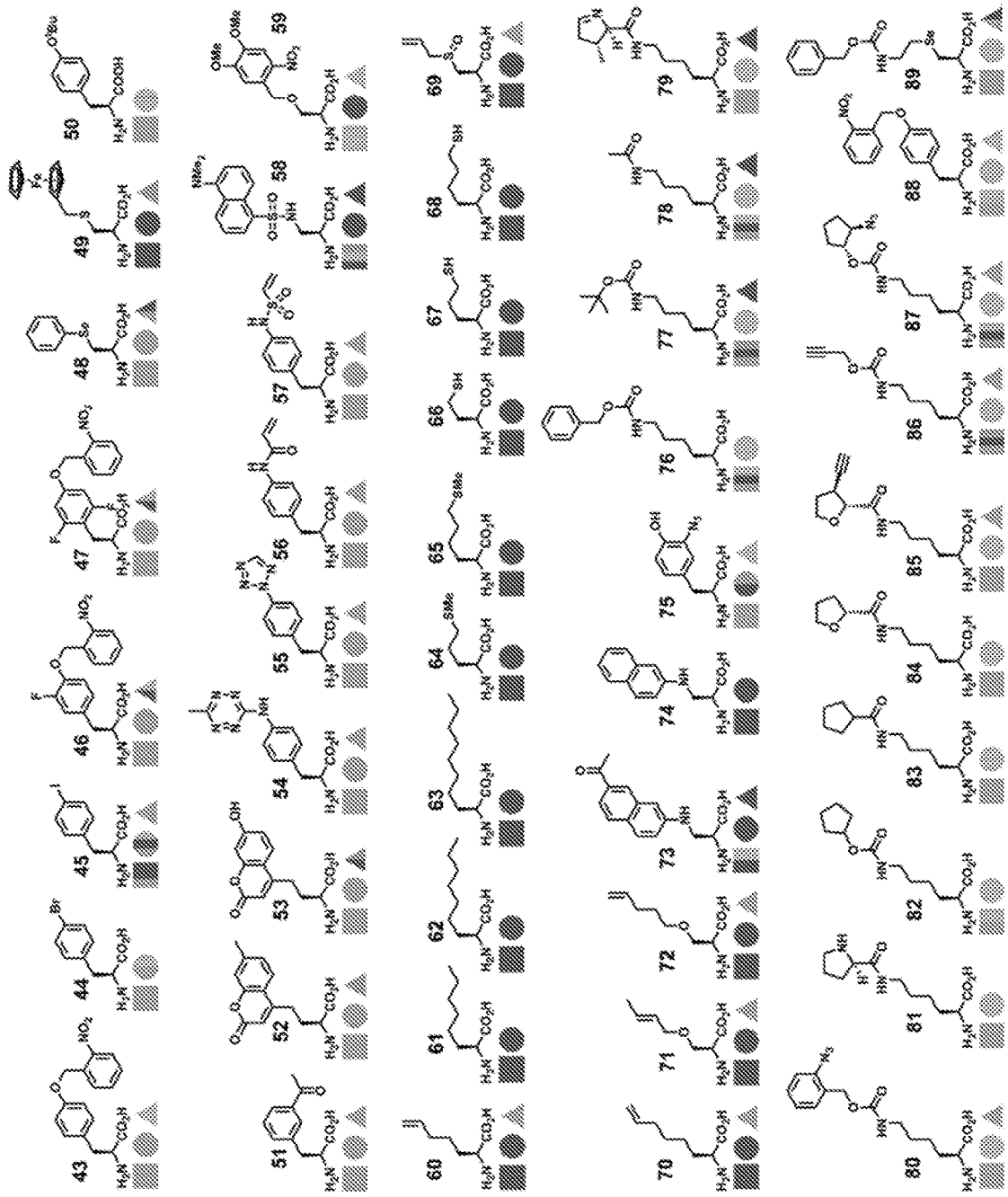
Figure 3C:
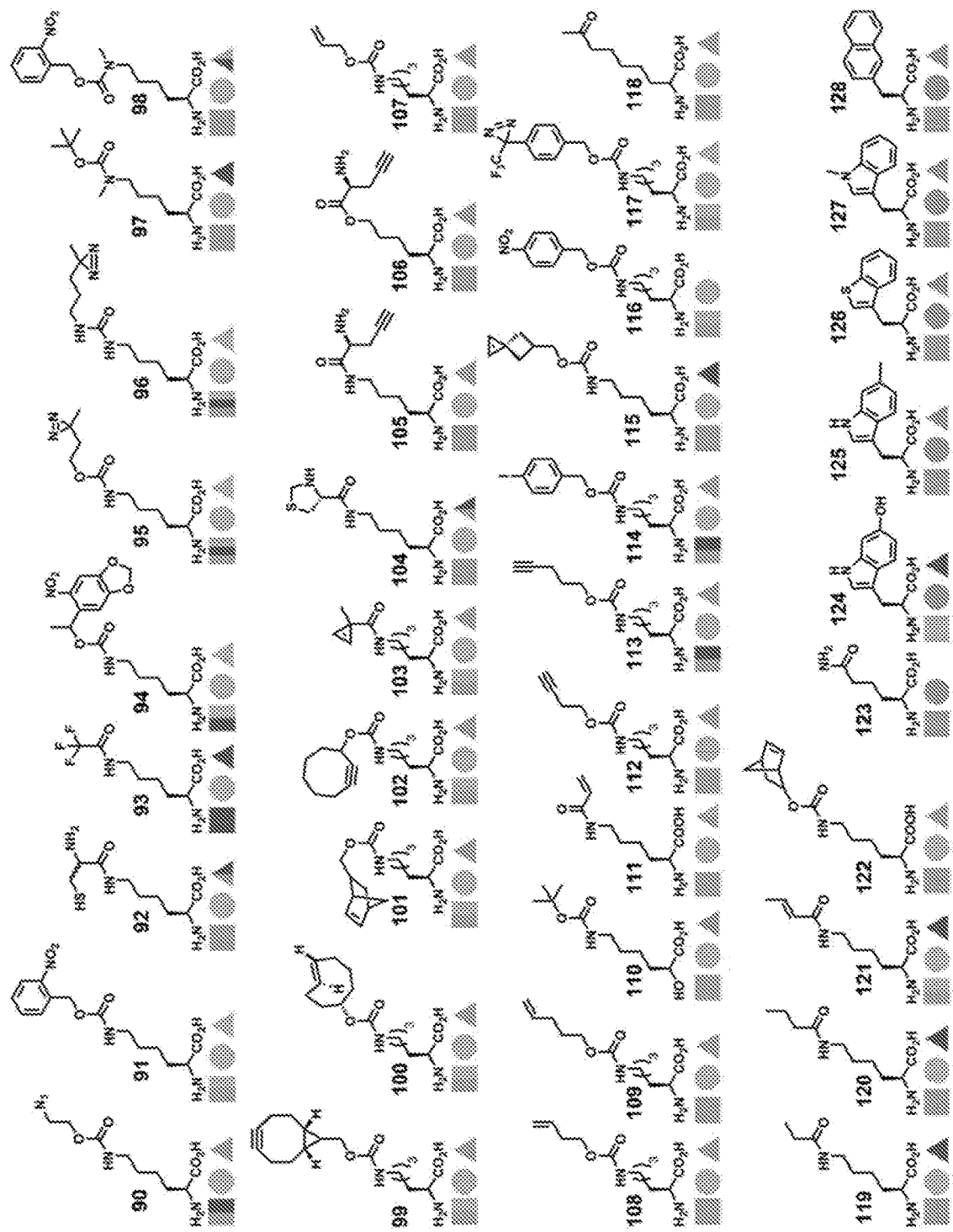
Figure 3D:
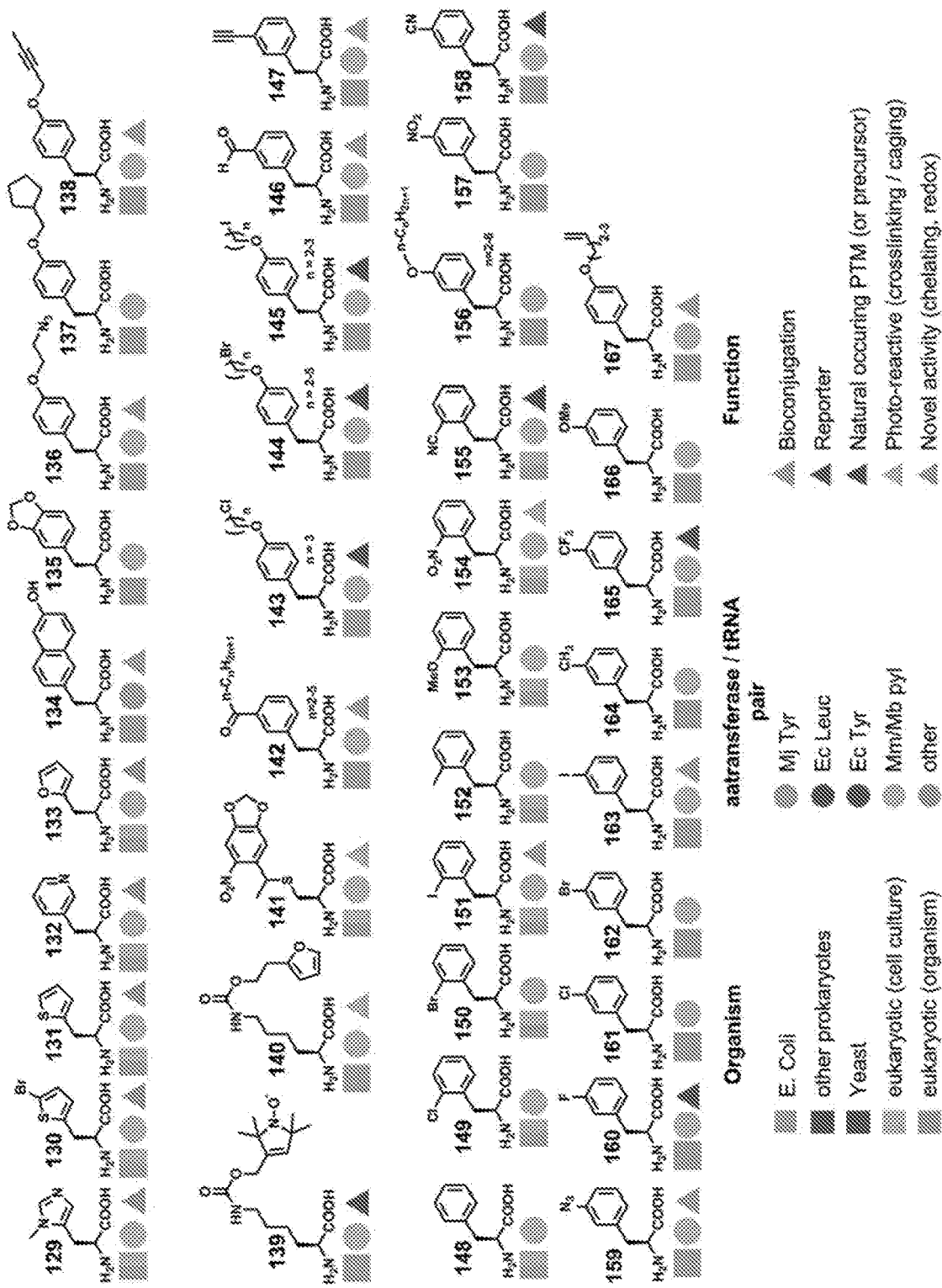
Figure 4A:
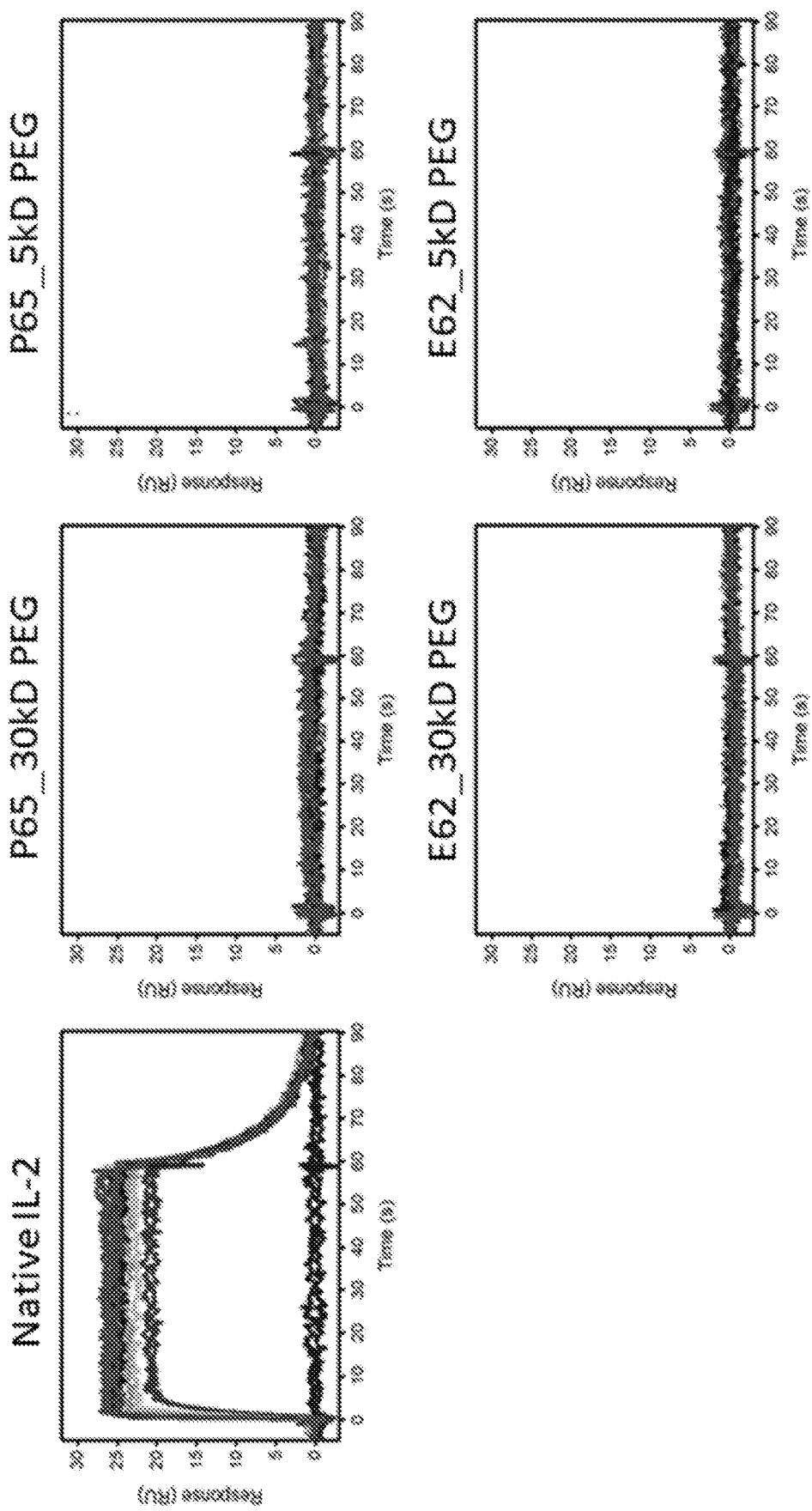
FIG. 4A-FIG. 4B show surface plasmon resonance (SPR) analysis of P65_30kD, P65_5kD, E62_30kD, and E62_5kD PEG conjugates.
Figure 4B:
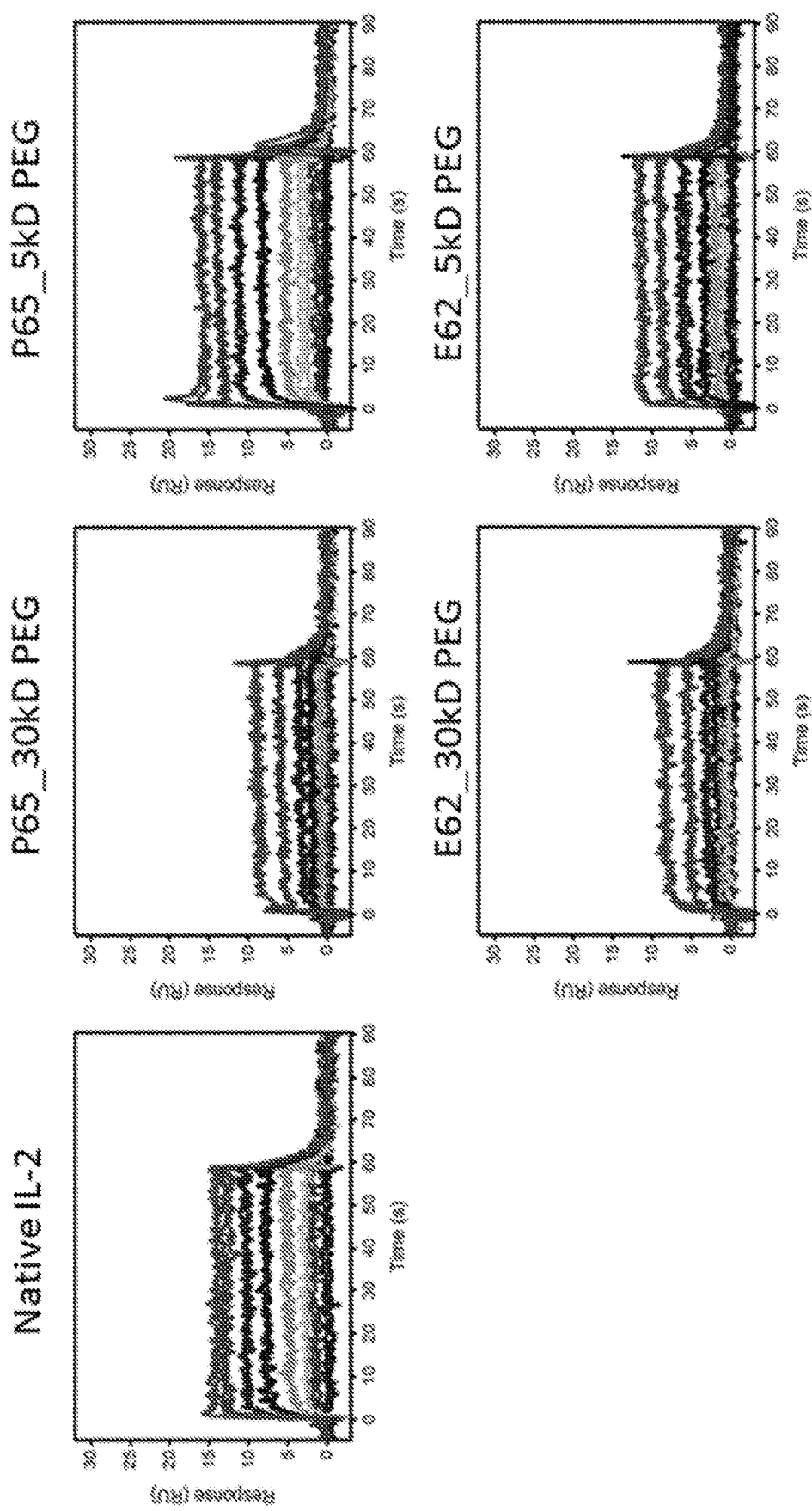

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biocheim Biophys Aceta 1844(6): 1059-4070 (2014). In some instances, the unnatural amino acid comprises an unnatural amino acid illustrated in FIG. 2 (e.g., FIG. 2A and FIG. 2B).

In some embodiments, the unnatural amino acid comprises an unnatural amino acid illustrated in FIG. 3A—FIG. 3D (adopted from Table 1 of Dumas et al., *Chemical Science* 2015, 6, 50-69).

In some embodiments, an unnatural amino acid incorporated into a cytokine described herein (e.g., the IL polypeptide) is disclosed in U.S. Pat. Nos. 9,840,493; 9,682,934; US 2017/0260137; U.S. Pat. No. 9,938,516; or US 2018/0086734. Exemplary UAAs that can be incorporated by such synthetases include para-methylazido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into cytokines in-vivo. In some embodiments, such UAAs are incorporated into cytokines in a cell-free system.

Conjugating Moieties

In certain embodiments, disclosed herein are conjugating moieties that are bound to one or more cytokines (e.g., interleukins, IFNs, or TNFs) described supra. In some instances, the conjugating moiety is a molecule that perturbs the interaction of a cytokine with its receptor. In some instances, the conjugating moiety is any molecule that when bond to the cytokine, enables the cytokine conjugate to modulate an immune response. In some instances, the conjugating moiety is bound to the cytokine through a covalent bond. In some instances, a cytokine described herein is attached to a conjugating moiety with a triazole group. In some instances, a cytokine described herein is attached to a conjugating moiety with a dihydropyridazine or pyridazine group. In some instances, the conjugating moiety comprises a water-soluble polymer. In other instances, the conjugating moiety comprises a protein or a binding fragment thereof. In additional instances, the conjugating moiety comprises a peptide. In additional instances, the conjugating moiety comprises a nucleic acid. In additional instances, the conjugating moiety comprises a small molecule. In additional instances, the conjugating moiety comprises a bioconjugate (e.g., a TLR agonist such as a TLR1, TLR2, TLR3, TLR4, TLR5, TLR6, TLR7, TLR8, or TLR9 agonist; or a synthetic ligand such as Pam3Cys, CFA, MALP2, Pam2Cys, FSL-1, Hib-OMPC, Poly I:C, poly A:U, AGP, MPL A, RC-529, MDF2β, CFA, or Flagellin). In some cases, the conjugating moiety increases serum half-life, and/or improves stability. In some cases, the conjugating moiety reduces cytokine interaction with one or more cytokine receptor domains or subunits. In additional cases, the conjugating moiety blocks cytokine interaction with one or more cytokine domains or subunits with its cognate receptor(s). In some embodiments, cytokine conjugates described herein comprise multiple conjugating moieties. In some embodiments, a conjugating moiety is attached to an unnatural or natural amino acid in the cytokine peptide. In some embodiments, a cytokine conjugate comprises a conjugating moiety attached to a natural amino acid. In some embodiments, a cytokine conjugate is attached to an unnatural amino acid in the cytokine peptide. In some embodiments, a conjugating moiety is attached to the N or C terminal amino acid of the cytokine peptide. Various combinations sites are disclosed herein, for example, a first conjugating moiety is attached to an unnatural or natural amino acid in the cytokine peptide, and a second conjugating moiety is attached to the N or C terminal amino acid of the cytokine peptide. In some embodiments, a single conjugating moiety is attached to multiple residues of the cytokine peptide (e.g. a staple). In some embodiments, a conjugating moiety is attached to both the N and C terminal amino acids of the cytokine peptide.

Water-Soluble Polymers

In some embodiments, a conjugating moiety descried herein is a water-soluble polymer. In some instances, the water-soluble polymer is a nonpeptidic, nontoxic, and biocompatible. As used herein, a substance is considered biocompatible if the beneficial effects associated with use of the substance alone or with another substance (e.g., an active agent such as a cytokine moiety) in connection with living tissues (e.g., administration to a patient) outweighs any deleterious effects as evaluated by a clinician, e.g., a physician, a toxicologist, or a clinical development specialist. In some instances, a water-soluble polymer is further non-immunogenic. In some instances, a substance is considered non-immunogenic if the intended use of the substance in vivo does not produce an undesired immune response (e.g., the formation of antibodies) or, if an immune response is produced, that such a response is not deemed clinically significant or important as evaluated by a clinician, e.g., a physician, a toxicologist, or a clinical development specialist.

In some instances, the water-soluble polymer is characterized as having from about 2 to about 300 termini. Exemplary water soluble polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol) (PVA), polyacrylamide (PAAm), poly(N-(2-hydroxypropyl) methacrylamide) (PHPMA), polydimethylacrylamide (PDAAm), polyphosphazene, polyoxazolines ("POZ") (which are described in WO 2008/106186), poly(N-acryloylmorpholine), and combinations of any of the foregoing.

In some cases, the water-soluble polymer is not limited to a particular structure. In some cases, the water-soluble polymer is linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

In some embodiments, the weight-average molecular weight of the water-soluble polymer in the IL-2 conjugate is from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

PEGs will typically comprise a number of ($OCH_2CH_2$) monomers [or ($CH_2CH_2O$) monomers, depending on how the PEG is defined]. As used herein, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In some instances, the water-soluble polymer is an end-capped polymer, that is, a polymer having at least one terminus capped with a relatively inert group, such as a lower $C_{1-6}$ alkoxy group, or a hydroxyl group. When the polymer is PEG, for example, a methoxy-PEG (commonly referred to as mPEG) may be used, which is a linear form of PEG wherein one terminus of the polymer is a methoxy (—$OCH_3$) group, while the other terminus is a hydroxyl or other functional group that can be optionally chemically modified.

In some embodiments, exemplary water-soluble polymers include, but are not limited to, linear or branched discrete PEG (dPEG) from Quanta Biodesign, Ltd; linear, branched, or forked PEGs from Nektar Therapeutics; and Y-shaped PEG derivatives from JenKem Technology.

In some embodiments, a cytokine (e.g., an interleukin, IFN, or TNF) polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol) (PVA), polyacrylamide (PAAm), polydimethylacrylamide (PDAAm), poly(N-(2-hydroxypropyl) methacrylamide)

(PHPMA), polyphosphazene, polyoxazolines ("POZ"), poly(N-acryloylmorpholine), and a combination thereof. In some instances, the cytokine polypeptide is conjugated to PEG (e.g., PEGylated). In some instances, the cytokine polypeptide is conjugated to PPG. In some instances, the cytokine polypeptide is conjugated to POZ. In some instances, the cytokine polypeptide is conjugated to PVP.

In some embodiments, an IL-2 polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly(N-acryloylmorpholine), and a combination thereof. In some instances, the IL-2 polypeptide is conjugated to PEG (e.g., PEGylated). In some instances, the IL-2 polypeptide is conjugated to PPG. In some instances, the IL-2 polypeptide is conjugated to POZ. In some instances, the IL-2 polypeptide is conjugated to PVP.

In some instances, a water-soluble polymer comprises a polyglycerol (PG). In some cases, the polyglycerol is a hyperbranched PG (HPG) (e.g., as described by Imran, et al. "Influence of architecture of high molecular weight linear and branched polyglycerols on their biocompatibility and biodistribution," *Biomaterials* 33:9135-9147 (2012)). In other cases, the polyglycerol is a linear PG (LPG). In additional cases, the polyglycerol is a midfunctional PG, a linear-block-hyperbranched PG (e.g., as described by Wurm et. Al., "Squaric acid mediated synthesis and biological activity of a library of linear and hyperbranched poly(glycerol)-protein conjugates," *Biomacromolecules* 13:1161-1171 (2012)), or a side-chain functional PG (e.g., as described by Li, et. al., "Synthesis of linear polyether polyol derivatives as new materials for bioconjugation," *Bioconjugate Chem.* 20:780-789 (2009).

In some instances, a cytokine (e.g., an interleukin, IFN, or TNF) polypeptide described herein is conjugated to a PG, e.g., a HPG, a LPG, a midfunctional PG, a linear-block-hyperbranched PG, or a side-chain functional PG. In some instances, the cytokine is an IL-2 polypeptide. In some cases, the IL-2 polypeptide is conjugated to a PG, a midfunctional PG, a linear-block-hyperbranched PG.

In some embodiments, a water-soluble polymer is a degradable synthetic PEG alternative. Exemplary degradable synthetic PEG alternatives include, but are not limited to, poly[oligo(ethylene glycol)methyl methacrylate] (POEGMA); backbone modified PEG derivatives generated by polymerization of telechelic, or di-end-functionalized PEG-based macromonomers; PEG derivatives comprising comonomers comprising degradable linkage such as poly[(ethylene oxie)-co-(methylene ethylene oxide)][P(EO-co-MEO)], cyclic ketene acetals such as 5,6-benzo-2-methylene-1,3-dioxepane (BMDO), 2-methylene-1,3-dioxepane (MDO), and 2-methylene-4-phenyl-1,3-dioxolane (MPDL) copolymerized with OEGMA; or poly-($\epsilon$-caprolactone)-graft-poly(ethylene oxide) (PCL-g-PEO).

In some instances, a cytokine (e.g., an interleukin, IFN, or TNF) polypeptide described herein is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO. In some instances, the cytokine is an IL-2 polypeptide. In some cases, the IL-2 polypeptide is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO.

In some embodiments, a water-soluble polymer comprises a poly(zwitterions). Exemplary poly(zwitterions) include, but are not limited to, poly(sulfobetaine methacrylate) (PSBMA), poly(carboxybetaine methacrylate) (PCBMA), and poly(2-methyacryloyloxyethyl phosphorylcholine) (PMPC). In some instances, a cytokine (e.g., an interleukin, IFN, or TNF) polypeptide described herein is conjugated to a poly(zwitterion) such as PSBMA, PCBMA, or PMPC. In some cases, the cytokine is an IL-2 polypeptide. In some cases, the IL-2 polypeptide is conjugated to a poly(zwitterion) such as PSBMA, PCBMA, or PMPC.

In some embodiments, a water-soluble polymer comprises a polycarbonate. Exemplary polycarbones include, but are not limited to, pentafluorophenyl 5-methyl-2-oxo-1,3-dioxane-5-carboxylate (MTC-OC$_6$F$_5$). In some instances, a cytokine (e.g., an interleukin, IFN, or TNF) polypeptide described herein is conjugated to a polycarbonate such as MTC-OC$_6$F$_5$. In some cases, the cytokine is an IL-2 polypeptide. In some cases, the IL-2 polypeptide is conjugated to a polycarbonate such as MTC-OC$_6$F$_5$.

In some embodiments, a water-soluble polymer comprises a polymer hybrid, such as for example, a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some instances, a cytokine (e.g., an interleukin, IFN, or TNF) polypeptide described herein is conjugated to a polymer hybrid such as a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some cases, the cytokine is an IL-2 polypeptide. In some cases, the IL-2 polypeptide is conjugated to a polymer hybrid such as a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer).

In some instances, a water-soluble polymer comprises a polysaccharide. Exemplary polysaccharides include, but are not limited to, dextran, polysialic acid (PSA), hyaluronic acid (HA), amylose, heparin, heparan sulfate (HS), dextrin, or hydroxyethyl-starch (HES). In some cases, a cytokine (e.g., an interleukin, IFN, or TNF) polypeptide is conjugated to a polysaccharide. In some cases, an IL-2 polypeptide is conjugated to dextran. In some cases, an IL-2 polypeptide is conjugated to PSA. In some cases, an IL-2 polypeptide is conjugated to HA. In some cases, an IL-2 polypeptide is conjugated to amylose. In some cases, an IL-2 polypeptide is conjugated to heparin. In some cases, an IL-2 polypeptide is conjugated to HS. In some cases, an IL-2 polypeptide is conjugated to dextrin. In some cases, an IL-2 polypeptide is conjugated to HES.

In some cases, a water-soluble polymer comprises a glycan. Exemplary classes of glycans include N-linked glycans, O-linked glycans, glycolipids, O-GlcNAc, and glycosaminoglycans. In some cases, a cytokine (e.g., an interleukin, IFN, or TNF) polypeptide is conjugated to a glycan. In some cases, an IL-2 polypeptide is conjugated to N-linked glycans. In some cases, an IL-2 polypeptide is conjugated to O-linked glycans. In some cases, an IL-2 polypeptide is conjugated to glycolipids. In some cases, an IL-2 polypeptide is conjugated to O-GlcNAc. In some cases, an IL-2 polypeptide is conjugated to glycosaminoglycans.

In some embodiments, a water-soluble polymer comprises a polyoxazoline polymer. A polyoxazoline polymer is a linear synthetic polymer, and similar to PEG, comprises a low polydispersity. In some instances, a polyoxazoline polymer is a polydispersed polyoxazoline polymer, characterized with an average molecule weight. In some cases, the average molecule weight of a polyoxazoline polymer includes, for example, 1000, 1500, 2000, 2500, 3000, 3500, 4000, 4500, 5000, 5500, 6000, 6500, 7000, 7500, 8000, 10,000, 12,000, 20,000, 35,000, 40,000, 50,000, 60,000, 100,000, 200,000, 300,000, 400,000, or 500,000 Da. In some instances, a polyoxazoline polymer comprises poly(2-methyl 2-oxazoline) (PMOZ), poly(2-ethyl 2-oxazoline) (PEOZ), or poly(2-propyl 2-oxazoline) (PPOZ). In some cases, a cytokine (e.g., an interleukin, IFN, or TNF) polypeptide is conjugated to a polyoxazoline polymer. In some cases, an IL-2 polypeptide is conjugated to a polyoxazoline polymer. In some cases, an IL-2 polypeptide is conjugated to PMOZ. In some cases, an IL-2 polypeptide is conjugated to PEOZ. In some cases, an IL-2 polypeptide is conjugated to PPOZ.

In some instances, a water-soluble polymer comprises a polyacrylic acid polymer. In some cases, a cytokine (e.g., an interleukin, IFN, or TNF) polypeptide is conjugated to a polyacrylic acid polymer. In some cases, an IL-2 polypeptide is conjugated to a polyacrylic acid polymer.

In some instances, a water-soluble polymer comprises polyamine. Polyamine is an organic polymer comprising two or more primary amino groups. In some embodiments, a polyamine includes a branched polyamine, a linear polyamine, or cyclic polyamine. In some cases, a polyamine is a low-molecular-weight linear polyamine. Exemplary polyamines include putrescine, cadaverine, spermidine, spermine, ethylene diamine, 1,3-diaminopropane, hexamethylenediamine, tetraethylmethylenediamine, and piperazine. In some cases, a cytokine (e.g., an interleukin, IFN, or TNF) polypeptide is conjugated to a polyamine. In some cases, an IL-2 polypeptide is conjugated to polyamine. In some cases, an IL-2 polypeptide is conjugated to putrescine, cadaverine, spermidine, spermine, ethylene diamine, 1,3-diaminopropane, hexamethylenediamine, tetraethylmethylenediamine, or piperazine.

In some instances, a water-soluble polymer is described in U.S. Pat. Nos. 7,744,861, 8,273,833, and 7,803,777. In some instances, a cytokine (e.g., an interleukin, IFN, or TNF) polypeptide is conjugated to a linker described in U.S. Pat. Nos. 7,744,861, 8,273,833, or 7,803,777. In some cases, an IL-2 polypeptide is conjugated to a linker described in U.S. Pat. Nos. 7,744,861, 8,273,833, or 7,803,777.

Lipids

In some embodiments, a conjugating moiety descried herein is a lipid. In some instances, the lipid is a fatty acid. In some cases, the fatty acid is a saturated fatty acid. In other cases, the fatty acid is an unsaturated fatty acid. Exemplary fatty acids include, but are not limited to, fatty acids comprising from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the lipid binds to one or more serum proteins, thereby increasing serum stability and/or serum half-life.

In some embodiments, the lipid is conjugated to IL-2. In some instances, the lipid is a fatty acid, e.g., a saturated fatty acid or an unsaturated fatty acid. In some cases, the fatty acid is from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the fatty acid comprises about 6, 7, 8, 9, 10, 11, 12, 13, 14, 15, 16, 17, 18, 19, 20, 21, 22, 23, 24, 25, or 26 carbon atoms in length. In some cases, the fatty acid comprises caproic acid (hexanoic acid), enanthic acid (heptanoic acid), caprylic acid (octanoic acid), pelargonic acid (nonanoic acid), capric acid (decanoic acid), undecylic acid (undecanoic acid), lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric acid (tetracosanoic acid), pentacosylic acid (pentacosanoic acid), or cerotic acid (hexacosanoic acid).

In some embodiments, the IL-2 lipid conjugate enhances serum stability and/or serum half-life.

Proteins

In some embodiments, a conjugating moiety descried herein is a protein or a binding fragment thereof. Exemplary proteins include albumin, transferrin, or transthyretin. In some instances, the protein or a binding fragment thereof comprises an antibody, or its binding fragments thereof. In some cases, a cytokine conjugate comprises a protein or a binding fragment thereof. In some cases, an IL-2 conjugate comprising a protein or a binding fragment thereof has an increased serum half-life, and/or stability. In some cases, an IL-2 conjugate comprising a protein or a binding fragment thereof has a reduced IL-2 interaction with one or more IL-2R subunits. In additional cases, the protein or a binding fragment thereof blocks IL-2 interaction with one or more IL-2R subunits.

In some embodiments, the conjugating moiety is albumin. Albumin is a family of water-soluble globular proteins. It is commonly found in blood plasma, comprising about 55-60% of all plasma proteins. Human serum albumin (HSA) is a 585 amino acid polypeptide in which the tertiary structure is divided into three domains, domain I (amino acid residues 1-195), domain II (amino acid residues 196-383), and domain III (amino acid residues 384-585). Each domain further comprises a binding site, which can interact either reversibly or irreversibly with endogenous ligands such as long- and medium-chain fatty acids, bilirubin, or hemin, or exogenous compounds such as heterocyclic or aromatic compounds.

In some cases, a cytokine (e.g., an interleukin, IFN, or TNF) polypeptide is conjugated to albumin. In some cases, the cytokine polypeptide is conjugated to human serum albumin (HSA). In additional cases, the cytokine polypeptide is conjugated to a functional fragment of albumin.

In some instances, an IL-2 polypeptide is conjugated to albumin. In some cases, the IL-2 polypeptide is conjugated to human serum albumin (HSA). In additional cases, the IL-2 polypeptide is conjugated to a functional fragment of albumin.

In some embodiments, the conjugating moiety is transferrin. Transferrin is a 679 amino acid polypeptide that is about 80 kDa in size and comprises two $Fe^{3+}$ binding sites with one at the N-terminal domain and the other at the C-terminal domain. In some instances, human transferrin has a half-life of about 7-12 days.

In some instances, a cytokine (e.g., an interleukin, IFN, or TNF) polypeptide is conjugated to transferrin. In some cases, the cytokine polypeptide is conjugated to human transferrin. In additional cases, the cytokine polypeptide is conjugated to a functional fragment of transferrin.

In some instances, an IL-2 polypeptide is conjugated to transferrin. In some cases, the IL-2 polypeptide is conjugated to human transferrin. In additional cases, the IL-2 polypeptide is conjugated to a functional fragment of transferrin.

In some embodiments, the conjugating moiety is transthyretin (TTR). Transthyretin is a transport protein located in the serum and cerebrospinal fluid which transports the thyroid hormone thyroxine (T4) and retinol-binding protein bound to retinol.

In some instances, a cytokine (e.g., an interleukin, IFN, or TNF) polypeptide is conjugated to transthyretin (via one of its termini or via an internal hinge region). In some cases, the cytokine polypeptide is conjugated to a functional fragment of transthyretin.

In some instances, an IL-2 polypeptide is conjugated to transthyretin (via one of its termini or via an internal hinge region). In some cases, the IL-2 polypeptide is conjugated to a functional fragment of transthyretin.

In some embodiments, the conjugating moiety is an antibody, or its binding fragments thereof. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent $Fab_2$, F(ab)'$_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, the conjugating moiety comprises a scFv, bis-scFv, $(scFv)_2$, dsFv, or sdAb. In some cases, the conjugating moiety comprises a scFv. In some cases, the conjugating moiety comprises a bis-scFv. In some cases, the conjugating moiety comprises a $(scFv)_2$. In some cases, the conjugating moiety comprises a dsFv. In some cases, the conjugating moiety comprises a sdAb.

In some instances, the conjugating moiety comprises an Fc portion of an antibody, e.g., of IgG, IgA, IgM, IgE, or IgD. In some instances, the moiety comprises an Fc portion of IgG (e.g., $IgG_1$, $IgG_3$, or $IgG_4$).

In some cases, a cytokine (e.g., an interleukin, IFN, or TNF) polypeptide is conjugated to an antibody, or its binding fragments thereof. In some cases, the cytokine polypeptide is conjugated to a humanized antibody or binding fragment thereof, murine antibody or binding fragment thereof, chimeric antibody or binding fragment thereof, monoclonal antibody or binding fragment thereof, monovalent Fab', divalent $Fab_2$, F(ab)'$_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is conjugated to an Fc portion of an antibody. In additional cases, the cytokine polypeptide is conjugated to an Fc portion of IgG (e.g., $IgG_1$, $IgG_3$, or $IgG_4$).

In some cases, an IL-2 polypeptide is conjugated to an antibody, or its binding fragments thereof. In some cases, the IL-2 polypeptide is conjugated to a humanized antibody or binding fragment thereof, murine antibody or binding fragment thereof, chimeric antibody or binding fragment thereof, monoclonal antibody or binding fragment thereof, monovalent Fab', divalent $Fab_2$, F(ab)'$_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is conjugated to an Fc portion of an antibody. In additional cases, the IL-2 polypeptide is conjugated to an Fc portion of IgG (e.g., $IgG_1$, $IgG_3$, or $IgG_4$).

In some embodiments, an IL-2 polypeptide is conjugated to a water-soluble polymer (e.g., PEG) and an antibody or binding fragment thereof. In some cases, the antibody or binding fragments thereof comprises a humanized antibody or binding fragment thereof, murine antibody or binding fragment thereof, chimeric antibody or binding fragment thereof, monoclonal antibody or binding fragment thereof, monovalent Fab', divalent $Fab_2$, F(ab)'$_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In some cases, the antibody or binding fragments thereof comprises a scFv, bis-scFv, $(scFv)_2$, dsFv, or sdAb. In some cases, the antibody or binding fragments thereof comprises a scFv. In some cases, the antibody or binding fragment thereof guides the IL-2 conjugate to a target cell of interest and the water-soluble polymer enhances stability and/or serum half-life.

In some instances, one or more IL-2 polypeptide—water-soluble polymer (e.g., PEG) conjugates are further bound to an antibody or binding fragments thereof. In some instances, the ratio of the IL-2 conjugate to the antibody is about 1:1, 2:1, 3:1, 4:1, 5:1, 6:1, 7:1, 8:1, 9:1, 10:1, 11:1, or 12:1. In some cases, the ratio of the IL-2 conjugate to the antibody is about 1:1. In other cases, the ratio of the IL-2 conjugate to the antibody is about 2:1, 3:1, or 4:1. In additional cases, the ratio of the IL-2 conjugate to the antibody is about 6:1 or higher.

In some embodiments, the one or more IL-2 polypeptide—water-soluble polymer (e.g., PEG) conjugates are directly bound to the antibody or binding fragments thereof. In other instances, the IL-2 conjugate is indirectly bound to the antibody or binding fragments thereof with a linker. Exemplary linkers include homobifunctional linkers, heterobifunctional linkers, maleimide-based linkers, zero-trace linkers, self-immolative linkers, spacers, and the like.

In some embodiments, the antibody or binding fragments thereof is bound either directly or indirectly to the IL-2 polypeptide portion of the IL-2 polypeptide—water-soluble polymer (e.g., PEG) conjugate. In such cases, the conjugation site of the antibody to the IL-2 polypeptide is at a site that will not impede binding of the IL-2 polypeptide with the IL-2Rβγ. In additional cases, the conjugation site of the antibody to the IL-2 polypeptide is at a site that partially blocks binding of the IL-2 polypeptide with the IL-2Rβγ. In additional cases, the conjugation site of the antibody to the IL-2 polypeptide is at a site that will impede or further impede binding of the IL-2 polypeptide with the IL-2Rα. In other embodiments, the antibody or binding fragments thereof is bound either directly or indirectly to the water-soluble polymer portion of the IL-2 polypeptide—water-soluble polymer (e.g., PEG) conjugate.

Peptides

In some embodiments, a conjugating moiety descried herein is a peptide. In some instances, the peptide is a non-structured peptide. In some cases, a cytokine (e.g., an interleukin, IFN, or TNF) polypeptide is conjugated to a peptide. In some cases, the IL-2 conjugate comprising a peptide has an increased serum half-life, and/or stability. In some cases, the IL-2 conjugate comprising a peptide has a reduced IL-2 interaction with one or more IL-2R subunits. In additional cases, the peptide blocks IL-2 interaction with one or more IL-2R subunits.

In some instances, the conjugating moiety is a XTEN™ peptide (Amunix Operating Inc.) and the modification is referred to as XTENylation. XTENylation is the genetic fusion of a nucleic acid encoding a polypeptide of interest with a nucleic acid encoding a XTEN™ peptide (Amunix Operating Inc.), a long unstructured hydrophilic peptide comprising different percentage of six amino acids: Ala, Glu, Gly, Ser, and Thr. In some instances, a XTEN™ peptide is selected based on properties such as expression, genetic stability, solubility, aggregation resistance, enhanced half-life, increased potency, and/or increased in vitro activity in combination with a polypeptide of interest. In some cases, a cytokine (e.g., an interleukin, IFN, or TNF) polypeptide is conjugated to a XTEN peptide. In some cases, an IL-2 polypeptide is conjugated to a XTEN peptide.

In some instances, the conjugating moiety is a glycine-rich homoamino acid polymer (HAP) and the modification is referred to as HAPylation. HAPylation is the genetic fusion of a nucleic acid encoding a polypeptide of interest with a nucleic acid encoding a glycine-rich homoamino acid polymer (HAP). In some instances, the HAP polymer comprises a (Gly4Ser)$_n$ repeat motif (SEQ ID NO: 3) and sometimes are about 50, 100, 150, 200, 250, 300, or more residues in length. In some cases, a cytokine (e.g., an interleukin, IFN, or TNF) polypeptide is conjugated to HAP. In some cases, an IL-2 polypeptide is conjugated to HAP.

In some embodiments, the conjugating moiety is a PAS polypeptide and the modification is referred to as PASylation. PASylation is the genetic fusion of a nucleic acid encoding a polypeptide of interest with a nucleic acid encoding a PAS polypeptide. A PAS polypeptide is a hydrophilic uncharged polypeptide consisting of Pro, Ala and Ser residues. In some instances, the length of a PAS polypeptide is at least about 100, 200, 300, 400, 500, or 600 amino acids. In some cases, a cytokine (e.g., an interleukin, IFN, or TNF) polypeptide is conjugated to a PAS polypeptide. In some cases, an IL-2 polypeptide is conjugated to a PAS polypeptide.

In some embodiments, the conjugating moiety is an elastin-like polypeptide (ELP) and the modification is referred to as ELPylation. ELPylation is the genetic fusion of a nucleic acid encoding a polypeptide of interest with a nucleic acid encoding an elastin-like polypeptide (ELPs). An ELP comprises a VPGxG repeat motif (SEQ ID NO: 4) in which x is any amino acid except proline. In some cases, a cytokine (e.g., an interleukin, IFN, or TNF) polypeptide is conjugated to ELP. In some cases, an IL-2 polypeptide is conjugated to ELP.

In some embodiments, the conjugating moiety is a CTP peptide. A CTP peptide comprises a 31 amino acid residue peptide FQSSSS*KAPPPS*LPSPS*RLPGPS*DTPILPQ (SEQ ID NO: 5) in which the S* denotes O-glycosylation sites (OPKO). In some instances, a CTP peptide is genetically fused to a cytokine polypeptide (e.g., an IL-2 polypeptide). In some cases, a cytokine polypeptide (e.g., an IL-2 polypeptide) is conjugated to a CTP peptide.

In some embodiments, a cytokine (e.g., an IL-2 polypeptide) is modified by glutamylation. Glutamylation (or polyglutamylation) is a reversible posttranslational modification of glutamate, in which the γ-carboxy group of glutamate forms a peptide-like bond with the amino group of a free glutamate in which the α-carboxy group extends into a polyglutamate chain.

In some embodiments, a cytokine (e.g., an IL-2 polypeptide) is modified by a gelatin-like protein (GLK) polymer. In some instances, the GLK polymer comprises multiple repeats of Gly-Xaa-Yaa wherein Xaa and Yaa primarily comprise proline and 4-hydroxyproline, respectively. In some cases, the GLK polymer further comprises amino acid residues Pro, Gly, Glu, Qln, Asn, Ser, and Lys. In some cases, the length of the GLK polymer is about 20, 30, 40, 50, 60, 70, 80, 90, 100, 110, 120, 150 residues or longer.

Additional Conjugating Moieties

In some instances, the conjugating moiety comprises an extracellular biomarker. In some instances, the extracellular biomarker is a tumor antigen. In some instances, exemplary extracellular biomarker comprises CD19, PSMA, B7-H3, B7-H6, CD70, CEA, CSPG4, EGFRvIII, EphA3, EpCAM, EGFR, ErbB2 (HER2), FAP, FRα, GD2, GD3, Lewis-Y, mesothelin, Muc1, Muc 16, ROR1, TAG72, VEGFR2, CD11, Gr-1, CD204, CD16, CD49b, CD3, CD4, CD8, and B220. In some instances, the conjugating moiety is bond or conjugated to the cytokine (e.g., IL-2). In some cases, the conjugating moiety is genetically fused, for example, at the N-terminus or the C-terminus, of the cytokine (e.g., IL-2).

In some instances, the conjugating moiety comprises a molecule from a post-translational modification. In some instances, examples of post-translational modification include myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation. In some instances, the cytokine (e.g., IL-2) is modified by a post-translational modification such as myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation.

Conjugation

Linkers

In some embodiments, useful functional reactive groups for conjugating or binding a conjugating moiety to a cytokine polypeptide (e.g., an IL-2 polypeptide) described herein include, for example, zero or higher-order linkers. In some instances, an unnatural amino acid incorporated into an interleukin described herein comprises a functional reactive group. In some instances, a linker comprises a functional reactive group that reacts with an unnatural amino acid incorporated into an interleukin described herein. In some instances, a conjugating moiety comprises a functional reactive group that reacts with an unnatural amino acid incorporated into an interleukin described herein. In some instances, a conjugating moiety comprises a functional reactive group that reacts with a linker (optionally pre-attached to a cytokine peptide) described herein. In some embodiments, a linker comprises a reactive group that reacts with a natural amino acid in a cytokine peptide described herein. In some cases, higher-order linkers comprise bifunctional linkers, such as homobifunctional linkers or heterobifunctional linkers. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the bifunctional linker comprises a heterobifunctional linker. Exemplary heterobifunctional linker include, but are not limited to, amine-reactive and sulthydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoactyl)aminobenzoate (sIAB), sulfosuccinimidyl(4-iodoactyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy) succinimide ester (GMBs), N-(γ-maleimidobutyryloxy) sulfosuccinimide ester (sulfo-GMBs), succinimidyl 6-((iodoacetyl)amino)hexanoate (sIAX), succinimidyl 6-(((((6-(((iodoacetypamino)hexanoyl)amino)hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M₂C₂H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)-1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido) butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the reactive functional group comprises a nucleophilic group that is reactive to an electrophilic group present on a binding moiety (e.g., on a conjugating moiety or on IL-2). Exemplary electrophilic groups include carbonyl groups—such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide. In some embodiments, an unnatural amino acid incorporated into an interleukin described herein comprises an electrophilic group.

In some embodiments, the linker is a cleavable linker. In some embodiments, the cleavable linker is a dipeptide linker. In some embodiments, the dipeptide linker is valine-citrulline (Val-Cit), phenylalanine-lysine (Phe-Lys), valine-alanine (Val-Ala) and valine-lysine (Val-Lys). In some embodiments, the dipeptide linker is valine-citrulline.

In some embodiments, the linker is a peptide linker comprising, e.g., at least 2, 3, 4, 5, 6, 7, 8, 9, 10, 11, 12, 15, 20, 25, 30, 35, 40, 45, 50, or more amino acids. In some instances, the peptide linker comprises at most 2, 3, 4, 5, 6, 7, 8, 9, 10, 11, 12, 15, 20, 25, 30, 35, 40, 45, 50, or less amino acids. In additional cases, the peptide linker comprises about 2, 3, 4, 5, 6, 7, 8, 9, 10, 11, 12, 15, 20, 25, 30, 35, 40, 45, or 50 amino acids.

In some embodiments, the linker comprises a self-immolative linker moiety. In some embodiments, the self-immolative linker moiety comprises p-aminobenzyl alcohol (PAB), p-aminobenzyoxycarbonyl (PABC), or derivatives or analogs thereof. In some embodiments, the linker comprises a dipeptide linker moiety and a self-immolative linker moiety. In some embodiments, the self-immolative linker moiety is such as described in U.S. Pat. No. 9,089,614 and WIPO Application No. WO2015038426.

In some embodiments, the cleavable linker is glucuronide. In some embodiments, the cleavable linker is an acid-cleavable linker. In some embodiments, the acid-cleavable linker is hydrazine. In some embodiments, the cleavable linker is a reducible linker.

In some embodiments, the linker comprises a maleimide group. In some instances, the maleimide group is also referred to as a maleimide spacer. In some instances, the maleimide group further comprises a caproic acid, forming maleimidocaproyl (mc). In some cases, the linker comprises maleimidocaproyl (mc). In some cases, linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

Conjugation Chemistry

Various conjugation reactions are used to conjugate linkers, conjugation moieties, and unnatural amino acids incorporated into cytokine peptides described herein. Such conjugation reactions are often compatible with aqueous conditions, such as "bioorthogonal" reactions. In some embodiments, conjugation reactions are mediated by chemical reagents such as catalysts, light, or reactive chemical groups found on linkers, conjugation moieties, or unnatural amino acids. In some embodiments, conjugation reactions are mediated by enzymes. In some embodiments, a conjugation reaction used herein is described in Gong, Y., Pan, L. Tett. Lett. 2015, 56, 2123. In some embodiments, a conjugation reaction used herein is described in Chen, X.; Wu. Y-W. Org. Biomol. Chem. 2016, 14, 5417.

In some embodiments described herein, a conjugation reaction comprises reaction of a ketone or aldehyde with a nucleophile. In some embodiments, a conjugation reaction comprises reaction of a ketone with an aminoxy group to form an oxime. In some embodiments, a conjugation reaction comprises reaction of a ketone with an aryl or heteroaryl amine group to form an imine. In some embodiments, a conjugation reaction comprises reaction of an aldehyde with an aryl or heteroaryl amine group to form an imine. In some embodiments, a conjugation reaction described herein results in cytokine peptide comprising a linker or conjugation moiety attached via an oxime. In some embodiments, a conjugation reaction comprises a Pictet-Spengler reaction of an aldehyde or ketone with a tryptamine nucleophile. In some embodiments, a conjugation reaction comprises a hydrazino-Pictet-Spengler reaction. In some embodiments, a conjugation reaction comprises a Pictet-Spengler ligation.

In some embodiments described herein, a conjugation reaction described herein comprises reaction of an azide and a phosphine (Staudinger ligation). In some embodiments, the phosphine is an aryl phosphine. In some embodiments, the aryl phosphine comprises an ortho ester group. In some embodiments, the phosphine comprises the structure methyl 2-(diphenylphosphaneyl)benzoate. In some embodiments, a conjugation reaction described herein results in cytokine peptide comprising a linker or conjugation moiety attached via an arylamide. In some embodiments, a conjugation reaction described herein results in cytokine peptide comprising a linker or conjugation moiety attached via an amide.

In some embodiments described herein, a conjugation reaction described herein comprises a 1,3-dipolar cycloaddition reaction. In some embodiments, the 1,3-dipolar cycloaddition reaction comprises reaction of an azide and a phosphine ("Click" reaction). In some embodiments, the conjugation reaction is catalyzed by copper. In some embodiments, a conjugation reaction described herein results in cytokine peptide comprising a linker or conjugation moiety attached via a triazole. In some embodiments, a conjugation reaction described herein comprises reaction of an azide with a strained olefin. In some embodiments, a conjugation reaction described herein comprises reaction of an azide with a strained alkyne. In some embodiments, a conjugation reaction described herein comprises reaction of an azide with a cycloalkyne, for example, OCT, DIFO, DIFBO, DIBO, BARAC, TMTH, or other strained cycloalkyne, the structures of which are shown in Gong, Y., Pan, L. Tett. Lett. 2015, 56, 2123. In some embodiments, a 1,3-dipolar cycloaddition reaction is catalyzed by light ("photoclick"). In some embodiments, a conjugation reaction described herein comprises reaction of a terminal allyl group with a tetrazole and light. In some embodiments, a conjugation reaction described herein comprises reaction of a terminal alkynyl group with a tetrazole and light. In some embodiments, a conjugation reaction described herein comprises reaction of an O-allyl amino acid with a tetrazine and light. In some embodiments, a conjugation reaction described herein comprises reaction of O-allyl tyrosine with a tetrazine and light.

In some embodiments described herein, a conjugation reaction described herein comprises an inverse-electron demand cycloaddition reaction comprising a diene and a dienophile. In some embodiments, the diene comprises a tetrazine. In some embodiments, the dienophile comprises an alkene. In some embodiments, the dienophile comprises an alkyne. In some embodiments, the alkyne is a strained alkyne. In some embodiments, the alkene is a strained diene. In some embodiments, the alkyne is a trans-cyclooctyne. In some embodiments, the alkyne is a cyclooctene. In some embodiments, the alkene is a cyclopropene. In some embodiments, the alkene is a fluorocyclopropene. In some embodiments, a conjugation reaction described herein results in the formation of a cytokine peptide attached to a linker or conjugation moiety via a 6-membered ring heterocycle comprising two nitrogen atoms in the ring.

In some embodiments described herein, a conjugation reaction described herein comprises an olefin metathesis reaction. In some embodiments, a conjugation reaction described herein comprises reaction of an alkene and an alkyne with a ruthenium catalyst. In some embodiments, a conjugation reaction described herein comprises reaction of two alkenes with a ruthenium catalyst. In some embodiments, a conjugation reaction described herein comprises reaction of two alkynes with a ruthenium catalyst. In some embodiments, a conjugation reaction described herein comprises reaction of an alkene or alkyne with a ruthenium catalyst and an amino acid comprising an allyl group. In some embodiments, a conjugation reaction described herein comprises reaction of an alkene or alkyne with a ruthenium catalyst and an amino acid comprising an allyl sulfide or selenide. In some embodiments, a ruthenium catalyst is Hoveda-Grubbs $2^{nd}$ generation catalyst. In some embodiments, an olefin metathesis reaction comprises reaction of one or more strained alkenes or alkynes.

In some embodiments described herein, a conjugation reaction described herein comprises a cross-coupling reaction. In some embodiments, cross-coupling reactions comprise transition metal catalysts, such as iridium, gold, ruthenium, rhodium, palladium, nickel, platinum, or other transition metal catalyst and one or more ligands. In some embodiments, transition metal catalysts are water-soluble. In some embodiments described herein, a conjugation reaction described herein comprises a Suzuki-Miyaura cross-coupling reaction. In some embodiments described herein, a conjugation reaction described herein comprises reaction of an aryl halide (or triflate, or tosylate), an aryl or alkenyl boronic acid, and a palladium catalyst. In some embodiments described herein, a conjugation reaction described herein comprises a Sonogashira cross-coupling reaction. In some embodiments described herein, a conjugation reaction described herein comprises reaction of an aryl halide (or triflate, or tosylate), an alkyne, and a palladium catalyst. In some embodiments, cross-coupling reactions result in attachment of a linker or conjugating moiety to a cytokine peptide via a carbon-carbon bond.

In some embodiments described herein, a conjugation reaction described herein comprises a deprotection or "uncaging" reaction of a reactive group prior to conjugation. In some embodiments, a conjugation reaction described herein comprises uncaging of a reactive group with light, followed by a conjugation reaction. In some embodiments, a reactive group is protected with an aralkyl moiety comprising one or more nitro groups. In some embodiments, uncaging of a reactive group results in a free amine, sulfide, or other reactive group. In some embodiments, a conjugation reaction described herein comprises uncaging of a reactive group with a transition metal catalyst, followed by a conjugation reaction. In some embodiments, the transition metal catalyst comprises palladium and one or more ligands. In some embodiments, a reactive group is protected with an allyl moiety. In some embodiments, a reactive group is protected with an allylic carbamate. In some embodiments, a reactive group is protected with a propargylic moiety. In some embodiments, a reactive group is protected with a propargyl carbamate. In some embodiments, a reactive group is protected with a dienophile, wherein exposure to a diene (such as a tetrazine) results in deprotection of the reactive group.

In some embodiments described herein, a conjugation reaction described herein comprises a ligand-directed reaction, wherein a ligand (optionally) attached to a reactive group) facilitates the site of conjugation between the reactive group and the cytokine peptide. In some embodiments, the ligand is cleaved during or after reaction of the cytokine peptide with the reactive group. In some embodiments, the conjugation site of the cytokine peptide is a natural amino acid. In some embodiments, the conjugation site of the cytokine peptide is a lysine, cysteine, or serine. In some embodiments, the conjugation site of the cytokine peptide is an unnatural amino acid described herein. In some embodiments the reactive group comprises a leaving group, such as an electron-poor aryl or heteroaryl group. In some embodiments the reactive group comprises a leaving group, such as an electron-poor alkyl group that is displaced by the cytokine peptide. In some embodiments, a conjugation reaction described herein comprises reaction of a radical trapping agent with a radical species. In some embodiments, a conjugation reaction described herein comprises an oxidative radical addition reaction. In some embodiments, a radical trapping agent is an arylamine. In some embodiments, a radical species is a tyrosyl radical. In some embodiments, radical species are generated by a ruthenium catalyst (such as [Ru(bpy)$_3$]) and light.

Enzymatic reactions are optionally used for conjugation reactions described herein. Exemplary enzymatic conjugations include SortA-mediated conjugation, a TGs-mediated conjugation, or an FGE-mediated conjugation. In some embodiments, a conjugation reaction described herein comprises native protein ligation (NPL) of a terminal 1-amino-2-thio group with a thioester to form an amide bond.

Various conjugation reactions are described herein for reacting a linker or conjugating moiety with a cytokine peptide, wherein the reaction occurs with a natural ("canonical") amino acid in the cytokine peptide. In some embodiments, the natural amino acid is found at a conjugation position is found in a wild type sequence, or alternatively the position has been mutated. In some embodiments, a conjugation reaction comprises formation of a disulfide bond at a cysteine residue. In some embodiments, a conjugation reaction comprises a 1,4 Michael addition reaction of a cysteine or lysine. In some embodiments, a conjugation reaction comprises a cyanobenzothiazole ligation of a cysteine. In some embodiments, a conjugation reaction comprises cross-linking with an acetone moiety, such as 1,3-dichloro-2-propionone. In some embodiments, a conjugation reaction comprises a 1,4 Michael addition to a dehydroalanine, formed by reaction of cysteine with O-mesitylenesulfonyl-hydroxylamine. In some embodiments a conjugation reaction comprises reaction of a tyrosine with a triazolinedione (TAD), or TAD derivative. In some embodiments a conjugation reaction comprises reaction of a tryptophan with a rhodium carbenoid.

Methods of Use

Proliferative Diseases or Conditions

In some embodiments, described herein is a method of treating a proliferative disease or condition in a subject in need thereof, which comprises administering to the subject a therapeutically effective amount of a cytokine conjugate (e.g., an IL-2 conjugate) described herein. In some instances, the IL-2 conjugate comprises an isolated and purified IL-2 polypeptide and a conjugating moiety, wherein the IL-2 conjugate has a decreased affinity to an IL-2 receptor α (IL-2Rα) subunit relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid position selected from 1(35, T37, R38, T41, F42, K43, F44, Y45, E60, E61, E62, K64, P65, E68, V69, N71, L72, M104, C105, and Y107, wherein the numbering of the amino acid residues corresponds to SEQ ID NO: 1. In some cases, the IL-2 conjugate preferentially interact with the IL-2R13 and IL-2Rβγ subunits to form a IL-2/IL-2Rβγ complex. In some cases, the IL-2/IL-2Rβγ complex stimulates and/or enhances expansion of CD4+ helper cells, CD8+ effector naïve and memory T cells, NK cells, and/or NKT cells. In additional cases, the expansion of Teff cells skews the Teff:Treg ratio toward the Teff population.

In some embodiments, the proliferative disease or condition is a cancer. In some cases, the cancer is a solid tumor.

Exemplary solid tumors include, but are not limited to, bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some cases, the solid tumor is a metastatic cancer. In some cases, the solid tumor is a relapsed or refractory cancer.

In some instances, a cytokine (e.g., interleukin, IFN, or TNF) conjugate described herein is administered to a subject in need thereof, for treating a solid tumor. In such cases, the subject has bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some cases, the solid tumor is a metastatic cancer. In some cases, the solid tumor is a relapsed or refractory cancer.

In some instances, an IL-2 conjugate described herein is administered to a subject in need thereof, for treating a solid tumor. In such cases, the subject has a bladder cancer, a bone cancer, a brain cancer, a breast cancer, a colorectal cancer, an esophageal cancer, an eye cancer, a head and neck cancer, a kidney cancer, a lung cancer, a melanoma, an ovarian cancer, a pancreatic cancer, or a prostate cancer. In some cases, the IL-2 conjugate is administered to a subject for the treatment of a bladder cancer. In some cases, the IL-2 conjugate is administered to a subject for the treatment of a breast cancer. In some cases, the IL-2 conjugate is administered to a subject for the treatment of a colorectal cancer. In some cases, the IL-2 conjugate is administered to a subject for the treatment of an esophageal cancer. In some cases, the IL-2 conjugate is administered to a subject for the treatment of a head and neck cancer. In some cases, the IL-2 conjugate is administered to a subject for the treatment of a kidney cancer. In some cases, the IL-2 conjugate is administered to a subject for the treatment of a lung cancer. In some cases, the IL-2 conjugate is administered to a subject for the treatment of a melanoma. In some cases, the IL-2 conjugate is administered to a subject for the treatment of an ovarian cancer. In some cases, the IL-2 conjugate is administered to a subject for the treatment of a pancreatic cancer. In some cases, the IL-2 conjugate is administered to a subject for the treatment of a prostate cancer.

In some embodiments, the IL-2 conjugate is administered to a subject for the treatment of a metastatic cancer. In some instances, the metastatic cancer comprises a metastatic bladder cancer, metastatic bone cancer, metastatic brain cancer, metastatic breast cancer, metastatic colorectal cancer, metastatic esophageal cancer, metastatic eye cancer, metastatic head and neck cancer, metastatic kidney cancer, metastatic lung cancer, metastatic melanoma, metastatic ovarian cancer, metastatic pancreatic cancer, or metastatic prostate cancer. In some cases, the IL-2 conjugate is administered to a subject for the treatment of metastatic bladder cancer, metastatic bone cancer, metastatic brain cancer, metastatic breast cancer, metastatic colorectal cancer, metastatic esophageal cancer, metastatic eye cancer, metastatic head and neck cancer, metastatic kidney cancer, metastatic lung cancer, metastatic melanoma, metastatic ovarian cancer, metastatic pancreatic cancer, or metastatic prostate cancer.

In some instances, the IL-2 conjugate is administered to a subject for the treatment of a relapsed or refractory cancer. In some instances, the relapsed or refractory cancer comprises a relapsed or refractory bladder cancer, relapsed or refractory bone cancer, relapsed or refractory brain cancer, relapsed or refractory breast cancer, relapsed or refractory colorectal cancer, relapsed or refractory esophageal cancer, relapsed or refractory eye cancer, relapsed or refractory head and neck cancer, relapsed or refractory kidney cancer, relapsed or refractory lung cancer, relapsed or refractory melanoma, relapsed or refractory ovarian cancer, relapsed or refractory pancreatic cancer, or relapsed or refractory prostate cancer. In some cases, the IL-2 conjugate is administered to a subject for the treatment of a relapsed or refractory bladder cancer, relapsed or refractory bone cancer, relapsed or refractory brain cancer, relapsed or refractory breast cancer, relapsed or refractory colorectal cancer, relapsed or refractory esophageal cancer, relapsed or refractory eye cancer, relapsed or refractory head and neck cancer, relapsed or refractory kidney cancer, relapsed or refractory lung cancer, relapsed or refractory melanoma, relapsed or refractory ovarian cancer, relapsed or refractory pancreatic cancer, or relapsed or refractory prostate cancer.

In some embodiments, the cancer is a treatment-naïve cancer. In such cases, the treatment-naïve cancer is a cancer that has not been treated by a therapy. In some cases, the treatment-naïve cancer is a solid tumor, such as bladder cancer, a bone cancer, a brain cancer, a breast cancer, a colorectal cancer, an esophageal cancer, an eye cancer, a head and neck cancer, a kidney cancer, a lung cancer, a melanoma, an ovarian cancer, a pancreatic cancer, or a prostate cancer. In some embodiments, described herein is a method of treating a treatment-naïve solid tumor in a subject in need thereof which comprises administering to the subject a cytokine conjugate (e.g., an IL-2 conjugate) described herein.

In some embodiments, the cancer is a hematologic malignancy. In some instances, the hematologic malignancy comprises a leukemia, a lymphoma, or a myeloma. In some cases, the hematologic malignancy is a T-cell malignancy. In other cases, the hematological malignancy is a B-cell malignancy. Exemplary hematologic malignancies include, but are not limited to, chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some cases, the hematologic malignancy is a metastatic cancer. In some cases, the metastatic cancer is a metastatic T-cell malignancy or a metastatic B-cell malignancy.

In some cases, the hematologic malignancy is a relapsed or refractory cancer. In some cases, the relapsed or refractory cancer is a relapsed or refractory T-cell malignancy or a relapsed or refractory B-cell malignancy.

In some instances, a cytokine (e.g., interleukin, IFN, or TNF) described herein is administered to a subject in need thereof, for treating a hematologic malignancy. In some cases, the subject has a T-cell malignancy. In some cases, the subject has a B-cell malignancy. In some cases, the subject has chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, an IL-2 conjugate described herein is administered to a subject in need thereof, for treating a hematologic malignancy. In some cases, the subject has a T-cell malignancy. In some cases, the subject has a B-cell malignancy. In some cases, the subject has chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the IL-2 conjugate is administered to a subject for the treatment of CLL. In some cases, the IL-2 conjugate is administered to a subject for the treatment of SLL. In some cases, the IL-2 conjugate is administered to a subject for the treatment of FL. In some cases, the IL-2 conjugate is administered to a subject for the treatment of DLBCL. In some cases, the IL-2 conjugate is administered to a subject for the treatment of MCL. In some cases, the IL-2 conjugate is administered to a subject for the treatment of Waldenstrom's macroglobulinemia. In some cases, the IL-2 conjugate is administered to a subject for the treatment of multiple myeloma. In some cases, the IL-2 conjugate is administered to a subject for the treatment of Burkitt's lymphoma.

In some cases, the IL-2 conjugate is administered to a subject for the treatment of a metastatic hematologic malignancy. In some cases, the IL-2 conjugate is administered to a subject for the treatment of a metastatic T-cell malignancy. In some cases, the IL-2 conjugate is administered to a subject for the treatment of a metastatic B-cell malignancy. In some cases, the IL-2 conjugate is administered to a subject for the treatment of a metastatic chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or metastatic lymphomatoid granulomatosis.

In some cases, the IL-2 conjugate is administered to a subject for the treatment of a relapsed or refractory hematologic malignancy. In some cases, the IL-2 conjugate is administered to a subject for the treatment of a relapsed or refractory T-cell malignancy. In some cases, the IL-2 conjugate is administered to a subject for the treatment of a relapsed or refractory B-cell malignancy. In some cases, the IL-2 conjugate is administered to a subject for the treatment of a relapsed or refractory chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Additional Therapeutic Agents

In some embodiments, an additional therapeutic agent is further administered to the subject. In some cases, the additional therapeutic agent is administered simultaneously with a cytokine conjugate (e.g., an IL-2 conjugate). In other cases, the additional therapeutic agent and the IL-2 conjugate are administered sequentially, e.g., the cytokine conjugate (e.g., IL-2 conjugate) is administered prior to the additional therapeutic agent or that the cytokine conjugate (e.g., IL-2 conjugate) is administered after administration of the additional therapeutic agent.

In some cases, the additional therapeutic agent comprises a chemotherapeutic agent, an immunotherapeutic agent, a targeted therapy, radiation therapy, or a combination thereof. Illustrative additional therapeutic agents include, but are not limited to, alkylating agents such as altretamine, busulfan, carboplatin, carmustine, chlorambucil, cisplatin, cyclophosphamide, dacarbazine, lomustine, melphalan, oxalaplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some cases, the additional therapeutic agent comprises a first-line therapy. As used herein, "first-line therapy" comprises a primary treatment for a subject with a cancer. In some instances, the cancer is a primary cancer. In other instances, the cancer is a metastatic or recurrent cancer. In some cases, the first-line therapy comprises chemotherapy. In other cases, the first-line treatment comprises radiation therapy. A skilled artisan would readily understand that different first-line treatments may be applicable to different type of cancers.

In some cases, a cytokine conjugate (e.g., IL-2 conjugate) is administered with an additional therapeutic agent selected from an alkylating agent such as altretamine, busulfan, carboplatin, carmustine, chlorambucil, cisplatin, cyclophosphamide, dacarbazine, lomustine, melphalan, oxalaplatin, temozolomide, or thiotepa; an antimetabolite such as 5-fluorouracil (5-FU), 6-mercaptopurine (6-MP), capecitabine, cytarabine, floxuridine, fludarabine, gemcitabine, hydroxyurea, methotrexate, or pemetrexed; an anthracycline such as daunorubicin, doxorubicin, epirubicin, or idarubicin; a topoisomerase I inhibitor such as topotecan or irinotecan (CPT-11); a topoisomerase II inhibitor such as etoposide (VP-16), teniposide, or mitoxantrone; a mitotic inhibitor such as docetaxel, estramustine, ixabepilone, paclitaxel, vinblastine, vincristine, or vinorelbine; or a corticosteroid such as prednisone, methylprednisolone, or dexamethasone.

In some instances, a cytokine conjugate (e.g., IL-2 conjugate) described herein is administered with an inhibitor of the enzyme poly ADP ribose polymerase (PARP). Exemplary PARP inhibitors include, but are not limited to, olaparib (AZD-2281, Lynparza®, from Astra Zeneca), rucaparib (PF-01367338, Rubraca®, from Clovis Oncology), niraparib (MK-4827, Zejula®, from Tesaro), talazoparib (BMN-673, from BioMarin Pharmaceutical Inc.), veliparib (ABT-888, from AbbVie), CK-102 (formerly CEP 9722, from Teva Pharmaceutical Industries Ltd.), E7016 (from Eisai), iniparib (BSI 201, from Sanofi), and pamiparib (BGB-290, from BeiGene). In some cases, the cytokine conjugate (e.g., IL-2 conjugate) is administered in combination with a PARP inhibitor such as olaparib, rucaparib, niraparib, talazoparib, veliparib, CK-102, E7016, iniparib, or pamiparib.

In some instances, a cytokine conjugate (e.g., IL-2 conjugate) described herein is administered with an immune checkpoint inhibitor. Exemplary checkpoint inhibitors include:
- PD-L1 inhibitors such as Genentech's MPDL3280A (RG7446), Anti-mouse PD-L1 antibody Clone 10F.9G2 (Cat #BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, and AstraZeneca's MEDI4736;
- PD-L2 inhibitors such as GlaxoSmithKline's AMP-224 (Amplimmune), and rHIgM12B7;
- PD-1 inhibitors such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG4 monoclonal antibody nivolumab (Opdivo®, BMS-936558, MDX1106), AstraZeneca's AMP-514 and AMP-224, and Pidilizumab (CT-011) from CureTech Ltd;
- CTLA-4 inhibitors such as Bristol Meyers Squibb's anti-CTLA-4 antibody ipilimumab (also known as Yervoy®, MDX-010, BMS-734016 and MDX-101), anti-CTLA4 antibody clone 9H10 from Millipore, Pfizer's tremelimumab (CP-675,206, ticilimumab), and anti-CTLA4 antibody clone BNI3 from Abcam;
- LAG3 inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12;
- B7-H3 inhibitors such as MGA271;
- MR inhibitors such as Lirilumab (IPH2101);
- CD137 inhibitors such as urelumab (BMS-663513, Bristol-Myers Squibb), PF-05082566 (anti-4-1BB, PF-2566, Pfizer), or XmAb-5592 (Xencor);
- PS inhibitors such as Bavituximab;
- and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some instances, the cytokine conjugate (e.g., IL-2 conjugate) is administered in combination with pembrolizumab, nivolumab, tremelimumab, or ipilimumab.

In some instances, a cytokine conjugate (e.g., IL-2 conjugate) described herein is administered with an antibody such as alemtuzumab, trastuzumab, ibritumomab tiuxetan, brentuximab vedotin, ado-trastuzumab emtansine, or blinatumomab.

In some instances, a cytokine conjugate (e.g., IL-2 conjugate) is administered with an additional therapeutic agent selected from an additional cytokine. In some instances, the additional cytokine enhances and/or synergizes T effector cell expansion and/or proliferation. In some cases, the additional cytokine comprises IL-1β, IL-6, IL-7, IL-10, IL-12, IL-15, IL-21, or TNFα. In some cases, the additional cytokine is IL-7. In some cases, the additional cytokine is IL-15. In some cases, the additional cytokine is IL-21. In some cases, the additional cytokine is TNFα.

In some instances, a cytokine conjugate (e.g., IL-2 conjugate) is administered with an additional therapeutic agent selected from a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2β, CFA, or Flagellin. In some cases, the cytokine conjugate (e.g., IL-2 conjugate) is administered with one or more TLR agonists selected from TLR1, TLR2, TLR3, TLR4, TLR5, TLR6, TLR7, TLR8, and TLR9. In some cases, the cytokine conjugate (e.g., IL-2 conjugate) is administered with one or more TLR agonists selected from Pam3Cys, CFA, MALP2, Pam2Cys, FSL-1, Hib-OMPC, Poly I:C, poly A:U, AGP, MPL A, RC-529, MDF2β, CFA, and Flagellin.

In some embodiments, a cytokine conjugate (e.g., IL-2 conjugate) is used in conjunction with an adoptive T cell transfer (ACT) therapy. In one embodiment, ACT involves identification of autologous T lymphocytes in a subject with, e.g., anti-tumor activity, expansion of the autologous T lymphocytes in vitro, and subsequent reinfusion of the expanded T lymphocytes into the subject. In another embodiment, ACT comprises use of allogeneic T lymphocytes with, e.g., anti-tumor activity, expansion of the T lymphocytes in vitro, and subsequent infusion of the expanded allogeneic T lymphocytes into a subject in need thereof. In some instances, a cytokine conjugate (e.g., IL-2 conjugate) described herein is used in conjunction with an autologous T lymphocytes as part of an ACT therapy. In other instances, a cytokine conjugate (e.g., IL-2 conjugate) described herein is used in conjunction with an allogeneic T lymphocytes as part of an ACT therapy. In some cases, the cytokine conjugate (e.g., IL-2 conjugate) is administered simultaneously with the ACT therapy to a subject in need thereof. In other cases, the cytokine conjugate (e.g., IL-2 conjugate) is administered sequentially with the ACT therapy to a subject in need thereof.

In some embodiments, a cytokine conjugate (e.g., IL-2 conjugate) is used for an ex vivo activation and/or expansion of an autologous and/or allogenic T cell transfer. In such cases, the cytokine conjugate (e.g., IL-2 conjugate) is used to activate and/or expand a sample comprising autologous and/or allogenic T cells and the cytokine conjugate (e.g., IL-2 conjugate) is optionally removed from the sample prior to administering the sample to a subject in need thereof.

In some embodiments, a cytokine conjugate (e.g., IL-2 conjugate) is administered with a vaccine. In some instances, a cytokine conjugate (e.g., IL-2 conjugate) is utilized in combination with an oncolytic virus. In such cases, the cytokine conjugate (e.g., IL-2 conjugate) acts as a stimulatory agent to modulate the immune response. In some instances, the cytokine conjugate (e.g., IL-2 conjugate) is used with an oncolytic virus as part of an adjuvant therapy. Exemplary oncolytic viruses include T-Vec (Amgen), G474 (Todo et al.), JX-594 (Sillajen), CG0070 (Cold Genesys), and Reolysin (Oncolytics Biotech). In some cases, the cytokine conjugate (e.g., IL-2 conjugate) is used in combination with an oncolytic virus such as T-Vec, G47Δ, JX-594, CG0070, or Reolysin.

In some embodiments, a cytokine conjugate (e.g., IL-2 conjugate) is administered in combination with a radiation therapy.

In some embodiments, a cytokine conjugate (e.g., IL-2 conjugate) is administered in combination with surgery.

Pathogenic Infections

In some embodiments, described herein is a method of treating a pathogenic infection in a subject in need thereof, which comprises administering to the subject a therapeutically effective amount of a cytokine conjugate (e.g., an IL-2 conjugate) described herein. In some instances, the IL-2 conjugate comprises an isolated and purified IL-2 polypeptide and a conjugating moiety, wherein the IL-2 conjugate has a decreased affinity to an IL-2 receptor α (IL-2Rα) subunit relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid position selected from K35, T37, R38, T41, F42, K43, F44, Y45, E60, E61, E62, K64, P65, E68, V69, N71, L72, M104, C105, and Y107, wherein the numbering of the amino acid residues corresponds to SEQ ID NO: 1. In some cases, the IL-2 conjugate preferentially interact with the IL-2R13 and IL-2Rβγ subunits to form a IL-2/IL-2Rβγ complex, which stimulates and/or enhances expansion of CD4+ helper cells, CD8+ effector naïve and memory cells, NK cells, and/or NKT cells. In additional cases, the IL-2 conjugate facilitates recognition of pathogenic reservoir by CD8+ T-cells.

In some embodiments, the pathogenic infection is a viral infection, in which upon treatment with an antiviral therapy, a viral reservoir (e.g., resting CD4+ T cells) persists in a treated host. In such instances, a cytokine conjugate (e.g., an IL-2 conjugate) described herein induces recognition of the viral reservoir by CD8+ T cells (or cytotoxic T cells). In some cases, the cytokine conjugate (e.g., IL-2 conjugate) is utilized as a monotherapy to redirect CD8+ T cells to infected resting cells for elimination. In some cases, the cytokine conjugate (e.g., IL-2 conjugate) is utilized in combination with an additional therapy to redirect CD8+ T cells to infected resting cells for elimination. Exemplary additional therapy comprises antiviral treatments such as acyclovir, brivudine, docosanol, famciclovir, foscarnet, idoxuridine, penciclovir, trifluridine, valacyclovir, and pritelivir.

In some embodiments, the virus is a DNA virus or an RNA virus. The DNA viruses include single-stranded (ss) DNA viruses, double-stranded (ds) DNA viruses, or DNA viruses that contain both ss and ds DNA regions. The RNA viruses include single-stranded (ss) RNA viruses or double-stranded (ds) RNA viruses. In some cases, the ssRNA viruses are further classified into positive-sense RNA viruses or negative-sense RNA viruses.

Exemplary dsDNA viruses include viruses from the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

Exemplary ssDNA viruses include viruses from the family: Anelloviridae, Bacillariodnaviridae, Bidnaviridae, Circoviridae, Geminiviridae, Inoviridae, Microviridae, Nanoviridae, Parvoviridae, and Spiraviridae.

Exemplary DNA viruses that contain both ss and ds DNA regions include viruses from the group of pleolipoviruses. In some cases, the pleolipoviruses include *Haloarcula hispanica* pleomorphic virus 1, *Halogeometricum pleomorphic virus 1, Halorubrum pleomorphic virus 1, Halorubrum pleomorphic virus 2, Halorubrum pleomorphic virus 3*, and *Halorubrum pleomorphic virus 6*.

Exemplary dsRNA viruses include viruses from the family: Birnaviridae, Chrysoviridae, Cystoviridae, Endomaviridae, Hypoviridae, Megavirnaviridae, Partitiviridae, Picobimaviridae, Reoviridae, Rotavirus, and Totiviridae.

Exemplary positive-sense ssRNA viruses include viruses from the family: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Marnaviridae, Mesoniviridae, Namaviridae, Nodaviridae, Permutotetraviridae, Picornaviridae, Potyviridae, Roniviridae, Retroviridae, Secoviridae, Togaviridae, Tombusviridae, Tymoviridae, and Virgaviridae.

Exemplary negative-sense ssRNA viruses include viruses from the family: Arenaviridae, Bornaviridae, Bunyaviridae, Filoviridae, Nyamiviridae, Ophioviridae, Orthomyxoviridae, Paramyxoviridae, and Rhabdoviridae.

In some embodiments, the pathogenic infection is caused by Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group. Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, bourn virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type Concovirus, bovine viral diarrhea virus, Buggy Creek virus, bullet shaped virus group, Bunyamwera virus supergroup. Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus; deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, FEE virus, ETA virus, ETA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillornavirus. European swine fever virus, Everglades virus, Eyach virus, fetid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus; feline syncytial virus, Filovirus, Flanders virus. Flavivirus, foot and mouth disease virus, Fort Morgan virus, Four Corners hantavirus, fowl adenovirus 1, fowlpox virus. Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, *Herpesvirus ateles*, *Herpesvirus hominis*, *Herpesvirus* infection, *Herpesvirus saimiri*, *Herpesvirus suis*, *Herpesvirus varicellae*, Highlands J virus, Hiratne rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gamtnaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immodeficiency virus, human immodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphotna virus II, human T cell lymphotropic virus type 1, human T cell lymphotropic virus type 2, human T lymphotropic virus 1, human T lymphotropic virus H, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirits, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus. Mason Pfizer monkey virus, Mastadenovirus, Mayaro virus, ME virus, measles virus, Malangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nainavirus, Nanimavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus, Pixuna virus, pneumonia virus of mice, Pneumovirus, poliomyelitis virus, poliovirus, Polydnavirus, polyhedral virus, polyoma virus. *Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi,* Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A vinis, simian human immunodeficiency virus, simian immunodeficiency virus, simian parainfluenza virus, simian cell lymphotrophic virus, simian virus, simian virus 40, Simplexvirus, Sin Nonibre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type 1, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tiornan virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus. Varicellovirus, Varicola, virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, or the Yug Bogdanovac virus.

In some embodiments, the pathogenic infection is caused by a retrovirus. Exemplary retroviruses include, but are not limited to, human immunodefiency virus (HIV), human T-cell leukemia viruses (HTLV), moloney murine leukemia virus (MuLV), murine mammary tumor virus (MMTV), avian leucosis and sarcoma viruses, or Mason-Pfizer monkey virus.

In some embodiments, a cytokine conjugate (e.g., an IL-2 conjugate) described herein is administered to a subject with a retroviral infection or during a latency period to reduce and/or eliminate infected cells that are in a resting period. In some cases, the retrovirus comprises human immunodefiency virus (HIV), human T-cell leukemia viruses (HTLV), moloney murine leukemia virus (MuLV), murine mammary tumor virus (MMTV), avian leucosis and sarcoma viruses, or Mason-Pfizer monkey virus. In some cases, the cytokine conjugate redirects CD8+ T cells to recognize and eliminate infected cells that are in a resting period.

In some cases, the cytokine conjugate is an IL-2 conjugate. In some instances, the IL-2 conjugate is administered to a subject with a retroviral infection or during a latency period to reduce and/or eliminate infected cells that are in a resting period. In some cases, the retrovirus comprises human immunodeficiency virus (HIV), human T-cell leukemia viruses (HTLV), moloney murine leukemia virus (MuLV), murine mammary tumor virus (MMTV), avian leucosis and sarcoma viruses, or Mason-Pfizer monkey virus. In some cases, the IL-2 conjugate redirects CD8+ T cells to recognize and eliminate infected cells that are in a resting period. In additional cases, the IL-2 conjugate is administered to the subject in combination with an antiretroviral therapy.

In some embodiments, the retrovirus is HIV. In some instances, a cytokine conjugate (e.g., an IL-2 conjugate) described herein is administered to a subject having acquired immune deficiency syndrome (AIDS) or during a latency period to reduce and/or eliminate HIV-infected cells (e.g., CD4+ T cells) that are in a resting period. In some cases, the cytokine conjugate is an IL-2 conjugate. In some cases, the IL-2 conjugate is administered to the subject in combination with an antiretroviral therapy. Exemplary HIV antiretroviral therapy includes:

nucleoside reverse transcriptase inhibitors (NRTIs) such as abacavir, emtricitabine, lamivudine, tenofovir disoproxil fumarate, and zidovudine;
non-nucleoside reverse transcriptase inhibitors (NNRTIs) such as efavirenz, etravirine, nevirapine, or rilpivirine;
protease inhibitors (PIs) such as atazanavir, darunavir, fosamprenavir, ritonavir, saquinavir, and tipranavir;
fusion inhibitors such as enfuvirtide;
CCR5 antagonists such as maraviroc;
integrase inhibitors such as dolutegravir and raltegravir;
post-attachment inhibitors such as ibalizumab;
pharmacokinetic enhancers such ac cobicistat; and cocktails such as abacavir and lamivudine; abacavir, dolutegravir, and lamivudine; abacavir, lamivudine, and zidovudine; atazanavir and cobicistat; bictegravir, emtricitabine, and tenofovir alafenamide; darunavir and cobicistat; dolutegravir and rilpivirine; efavirenz, emtricitabine, and tenofovir disoproxil fumarate; efavirenz, lamivudine, and tenofovir disoproxil fumarate; efavirenz, lamivudine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and tenofovir disoproxil fumarate; lamivudine and zidovudine; and lopinavir and ritonavir.

In some cases, the IL-2 conjugate is administered to the subject in combination with an antiretroviral therapy such as nucleoside reverse transcriptase inhibitors (NRTIs) such as abacavir, emtricitabine, lamivudine, tenofovir disoproxil fumarate, and zidovudine; non-nucleoside reverse transcriptase inhibitors (NNRTIs) such as efavirenz, etravirine, nevirapine, or rilpivirine; protease inhibitors (PIs) such as atazanavir, darunavir, fosamprenavir, ritonavir, saquinavir, and tipranavir; fusion inhibitors such as enfuvirtide; CCR5 antagonists such as maraviroc; integrase inhibitors such as dolutegravir and raltegravir; post-attachment inhibitors such as ibalizumab; pharmacokinetic enhancers such ac cobicistat; or cocktails such as abacavir and lamivudine; abacavir, dolutegravir, and lamivudine; abacavir, lamivudine, and zidovudine; atazanavir and cobicistat; bictegravir, emtricitabine, and tenofovir alafenamide; darunavir and cobicistat; dolutegravir and rilpivirine; efavirenz, emtricitabine, and tenofovir disoproxil fumarate; efavirenz, lamivudine, and tenofovir disoproxil fumarate; efavirenz, lamivudine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and tenofovir disoproxil fumarate; lamivudine and zidovudine; and lopinavir and ritonavir.

In some embodiments, the virus is a hepatitis virus, e.g., hepatitis A, B, C, D, or E. In some instances, a cytokine conjugate (e.g., an IL-2 conjugate) described herein is administered to a subject with a hepatitis infection or during a latency period to reduce and/or eliminate infected cells that are in a resting period. In some cases, the cytokine conjugate redirects CD8+ T cells to recognize and eliminate infected cells that are in a resting period.

In some cases, the cytokine conjugate is an IL-2 conjugate. In some instances, the IL-2 conjugate is administered to a subject with a hepatitis infection or during a latency period to reduce and/or eliminate infected cells that are in a resting period. In some cases, the IL-2 conjugate redirects CD8+ T cells to recognize and eliminate infected cells that are in a resting period. In some cases, the IL-2 conjugate is administered to the subject in combination with an antiviral therapy. Exemplary antiviral therapy for hepatitis include ribavirin; NS3/4A protease inhibitors such as paritaprevir, simeprevir, and grazoprevir; NS5A protease inhibitors such as ledipasvir, ombitasvir, elbasvir, and daclatasvir; NS5B nucleotide/nucleoside and nonnucleoside polymerase inhibitors such as sofosbuvir and dasabuvir; and combinations such as ledipasvir-sofosbuvir, dasabuvir-ombitasvir-paritaprevir-ritonavir; elbasvir-grazoprevir, ombitasvir-paritaprevir-ritonavir, sofosbuvir-velpatasvir, sofosbuvir-velpatasvir-voxilaprevir, and glecaprevir-pibrentasvir; and interferons such as peginterferon alfa-2a, peginterferon alfa-2b, and interferon alfa-2b. In some cases, e IL-2 conjugate is administered to the subject in combination with an antiviral therapy such as ribavirin; NS3/4A protease inhibitors such as paritaprevir, simeprevir, and grazoprevir; NS5A protease inhibitors such as ledipasvir, ombitasvir, elbasvir, and daclatasvir; NS5B nucleotide/nucleoside and nonnucleoside polymerase inhibitors such as sofosbuvir and dasabuvir; and combinations such as ledipasvir-sofosbuvir, dasabuvir-ombitasvir-paritaprevir-ritonavir; elbasvir-grazoprevir, ombitasvir-paritaprevir-ritonavir, sofosbuvir-velpatasvir, sofosbuvir-velpatasvir-voxilaprevir, and glecaprevir-pibrentasvir; and interferons such as peginterferon alfa-2a, peginterferon alfa-2b, and interferon alfa-2b.

Methods of Cell Population Expansion

In some embodiments, additionally described herein are methods of expanding lymphocyte populations, e.g., CD4+ helper cell, CD8+ effector naïve and memory cell, NK cell, and/or NKT cell populations, or methods of expanding a Treg cell population. In some instances, the method comprises contacting a cell with a cytokine conjugate described herein and interacting the cytokine with a cytokine receptor to form a complex, wherein the complex stimulates expansion of a distinct lymphocyte population.

In some instances, the method of expanding a CD4+ helper cell, CD8+ effector naïve and memory cell, Natural Killer (NK) cell, or Natural killer T (NKT) cell population comprises contacting a cell population with an isolated and modified IL-2 polypeptide described above for a time sufficient to induce formation of a complex with an IL-2Rβ, thereby stimulating the expansion of the Teff and/or NK cell population. In some instances, the method of expanding CD4+ helper cell, CD8+ effector naïve and memory cell, NK cell, and/or NKT cell populations comprises (a) contacting a cell population with an IL-2 conjugate described herein; and (b) interacting the IL-2 with IL-2R13 and IL-2Rγ subunits to form an IL-2/IL-2Rβγ complex; wherein the IL-2 conjugate has a decreased affinity to IL-2Rα subunit, and wherein the IL-2/IL-2Rβγ complex stimulates the expansion of CD4+ helper cells, CD8+ effector naïve and memory cells, NK cells, and/or NKT cells. As described above, the IL-2 conjugate comprises an isolated and purified IL-2 polypeptide; and a conjugating moiety that binds to the isolated and purified IL-2 polypeptide at an amino acid position selected from K35, T37, R38, T41, F42, K43, F44, Y45, E60, E61, E62, K64, P65, E68, V69, N71, L72, M104, C105, and Y107, wherein the numbering of the amino acid residues corresponds to SEQ ID NO: 1. In some instances, the amino acid position is selected from K35, T37, R38, T41, F42, K43, F44, Y45, E61, E62, E68, K64, P65, V69, L72, and Y107. In some instances, the amino acid position is selected from T37, R38, T41, F42, F44, Y45, E61, E62, E68, K64, P65, V69, L72, and Y107. In some instances, the amino acid position is selected from T37, R38, T41, F42, F44, Y45, E61, E62, E68, P65, V69, L72, and Y107. In some instances, the amino acid position is selected from T37, T41, F42, F44, Y45, P65, V69, L72, and Y107. In some instances, the amino acid position is selected from R38 and K64. In some instances, the amino acid position is selected from E61, E62, and E68. In some cases, the amino acid position is at E62.

In some instances, the IL-2 conjugate expands CD4+ T regulatory (Treg) cells by less than 20%, 15%, 10%, 5%, or 1% in the cell population. In some instances, the IL-2 conjugate does not expand CD4+ Treg cells in the cell population. In some instances, the ratio of the Teff cells to Treg cells in the cell population after incubation with the isolated and modified IL-2 polypeptide is at least 2:1, 3:1, 4:1, 5:1, 6:1, 7:1, 8:1, 9:1, 10:1, 20:1, 50:1, or 100:1. In some instances, the ratio of the Teff cells to Treg cells in the cell population after incubation with the isolated and modified IL-2 polypeptide is about 2:1, 3:1, 4:1, 5:1, 6:1, 7:1, 8:1, 9:1, 10:1, 20:1, 50:1, or 100:1.

In some instances, the time sufficient to induce formation of a complex with an IL-2R13 is at least 5 minutes, 10 minutes, 15 minutes, 20 minutes, 30 minutes, 1 hour, 2 hours, 3 hours, 4 hours, 5 hours, 8 hours, 10 hours, 12 hours, 18 hours, 24 hours, 2 days, 3 days, 4 days, 5 days, 6 days, or 7 days. In some instances, the time sufficient to induce formation of a complex with an IL-2R13 is about 5 minutes, 10 minutes, 15 minutes, 20 minutes, 30 minutes, 1 hour, 2 hours, 3 hours, 4 hours, 5 hours, 8 hours, 10 hours, 12 hours, 18 hours, 24 hours, 2 days, 3 days, 4 days, 5 days, 6 days, or 7 days.

In some instances, the method is an in vivo method.
In some instances, the method is an in vitro method.
In some instances, the method is an ex vivo method.

Cytokine Polypeptide Production

In some instances, the cytokine (e.g., interleukin, IFN, or TNF) polypeptides described herein, either containing a natural amino acid mutation or an unnatural amino acid mutation, are generated recombinantly or are synthesized chemically. In some instances, the cytokine (e.g., IL-2) polypeptides described herein are generated recombinantly, for example, either by a host cell system, or in a cell-free system.

In some instances, the cytokine (e.g., IL-2) polypeptides are generated recombinantly through a host cell system. In some cases, the host cell is a eukaryotic cell (e.g., mammalian cell, insect cells, yeast cells or plant cell) or a prokaryotic cell (e.g., gram-positive bacterium or a gram-negative bacterium). In some cases, a eukaryotic host cell is a mammalian host cell. In some cases, a mammalian host cell is a stable cell line, or a cell line that has incorporated a genetic material of interest into its own genome and has the capability to express the product of the genetic material after many generations of cell division. In other cases, a mammalian host cell is a transient cell line, or a cell line that has not incorporated a genetic material of interest into its own genome and does not have the capability to express the product of the genetic material after many generations of cell division.

Exemplary mammalian host cells include 293T cell line, 293A cell line, 293FT cell line, 293F cells, 293 H cells, A549 cells, MDCK cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some embodiments, an eukaryotic host cell is an insect host cell. Exemplary insect host cell include Drosophila S2 cells, Sf9 cells, Sf21 cells, High Five™ cells, and expresSF+® cells.

In some embodiments, a eukaryotic host cell is a yeast host cell. Exemplary yeast host cells include Pichia pastoris yeast strains such as GS115, KM71H, SMD1168, SMD1168H, and X-33, and Saccharomyces cerevisiae yeast strain such as INVSc1.

In some embodiments, an eukaryotic host cell is a plant host cell. In some instances, the plant cells comprise a cell from algae. Exemplary plant cell lines include strains from Chlamydomonas reinhardtii 137c, or Synechococcus elongatus PPC 7942.

In some embodiments, a host cell is a prokaryotic host cell. Exemplary prokaryotic host cells include BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, suitable polynucleic acid molecules or vectors for the production of an IL-2 polypeptide described herein include any suitable vectors derived from either a eukaryotic or prokaryotic source. Exemplary polynucleic acid molecules or vectors include vectors from bacteria (e.g., E. coli), insects, yeast (e.g., Pichia pastoris), algae, or mammalian source. Bacterial vectors include, for example, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Insect vectors include, for example, pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

Yeast vectors include, for example, Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 Pichia vector, pFLD1 Pichia pastoris vector, pGAPZA, B, & C Pichia pastoris vector, pPIC3.5K Pichia vector, pPIC6 A, B, & C Pichia vector, pPIC9K Pichia vector, pTEF1/Zeo, pYES2 yeast vector, pYES2/CT yeast vector, pYES2/NT A, B, & C yeast vector, or pYES3/CT yeast vector.

Algae vectors include, for example, pChlamy-4 vector or MCS vector.

Mammalian vectors include, for example, transient expression vectors or stable expression vectors. Exemplary mammalian transient expression vectors include p3xFLAG-CMV 8, pFLAG-Myc-CMV 19, pFLAG-Myc-CMV 23, pFLAG-CMV 2, pFLAG-CMV 6a, b, c, pFLAG-CMV 5.1, pFLAG-CMV 5a, b, c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Exemplary mammalian stable expression vectors include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is used for the production of a cytokine (e.g., IL-2) polypeptide described herein. In some cases, a cell-free system comprises a mixture of cytoplasmic and/or nuclear components from a cell and is suitable for in vitro nucleic acid synthesis. In some instances, a cell-free system utilizes prokaryotic cell components. In other instances, a cell-free system utilizes eukaryotic cell components. Nucleic acid synthesis is obtained in a cell-free system based on, for example, *Drosophila* cell, *Xenopus* egg, Archaea, or HeLa cells. Exemplary cell-free systems include *E. coli* S30 Extract system, *E. coli* T7 S30 system, or PURExpress®, XpressCF, and XpressCF+.

Cell-free translation systems variously comprise components such as plasmids, mRNA, DNA, tRNAs, synthetases, release factors, ribosomes, chaperone proteins, translation initiation and elongation factors, natural and/or unnatural amino acids, and/or other components used for protein expression. Such components are optionally modified to improve yields, increase synthesis rate, increase protein product fidelity, or incorporate unnatural amino acids. In some embodiments, cytokines described herein are synthesized using cell-free translation systems described in U.S. Pat. No. 8,778,631; US 2017/0283469; US 2018/0051065; US 2014/0315245; or U.S. Pat. No. 8,778,631. In some embodiments, cell-free translation systems comprise modified release factors, or even removal of one or more release factors from the system. In some embodiments, cell-free translation systems comprise a reduced protease concentration. In some embodiments, cell-free translation systems comprise modified tRNAs with re-assigned codons used to code for unnatural amino acids. In some embodiments, the synthetases described herein for the incorporation of unnatural amino acids are used in cell-free translation systems. In some embodiments, tRNAs are pre-loaded with unnatural amino acids using enzymatic or chemical methods before being added to a cell-free translation system. In some embodiments, components for a cell-free translation system are obtained from modified organisms, such as modified bacteria, yeast, or other organism.

In some embodiments, a cytokine (e.g., IL-2) polypeptide is generated as a circularly permuted form, either via an expression host system or through a cell-free system.

Production of Cytokine Polypeptide Comprising an Unnatural Amino Acid

An orthogonal or expanded genetic code can be used in the present disclosure, in which one or more specific codons present in the nucleic acid sequence of a cytokine (e.g., IL-2) polypeptide are allocated to encode the unnatural amino acid so that it can be genetically incorporated into the cytokine (e.g., IL-2) by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

In some instances, the codon is the codon amber, ochre, opal or a quadruplet codon. In some cases, the codon corresponds to the orthogonal tRNA which will be used to carry the unnatural amino acid. In some cases, the codon is amber. In other cases, the codon is an orthogonal codon.

In some instances, the codon is a quadruplet codon, which can be decoded by an orthogonal ribosome ribo-Q1. In some cases, the quadruplet codon is as illustrated in Neumann, et al., "Encoding multiple unnatural amino acids via evolution of a quadruplet-decoding ribosome," *Nature,* 464(7287): 441-444 (2010).

In some instances, a codon used in the present disclosure is a recoded codon, e.g., a synonymous codon or a rare codon that is replaced with alternative codon. In some cases, the recoded codon is as described in Napolitano, et al., "Emergent rules for codon choice elucidated by editing rare argine codons in *Escherichia coli*," PNAS, 113(38): E5588-5597 (2016). In some cases, the recoded codon is as described in Ostrov et al., "Design, synthesis, and testing toward a 57-codon genome," Science 353(6301): 819-822 (2016).

In some instances, unnatural nucleic acids are utilized leading to incorporation of one or more unnatural amino acids into the cytokine (e.g., IL-2). Exemplary unnatural nucleic acids include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and O-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CH$_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thio-guanine, 2-thio-thymine, 4-thio-thymine, 5-propynyl-uracil, 4-thiouracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272;

5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke- and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acids in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo[2.3-d] pyrimidin-5-yl, 2-amino-4-oxopyrolo[2,3-d]pyrimidin-5-yl, 2-amino-4-oxopyrrolo[2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hatter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or $C(R_1)(R_2)$ (R═H, $C_1$-$C_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$O]$_m$CH$_3$, —O$(CH_2)_n$OCH$_3$, —O$(CH_2)_n$NH$_2$, —O$(CH_2)_n$CH$_3$, —O$(CH_2)_n$ONH$_2$, and —O$(CH_2)_n$ON[$(CH_2)_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'—OCH$_3$, and 2'-O(CH$_2$)$_2$OCH$_3$ substituent groups. The substituent at the 2' position can also be selected from allyl, amino, azido, thio, O-allyl, O—($C_1$-$C_{10}$ alkyl), OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted $C_1$-$C_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845); 4'-C(CH$_3$)(CH$_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N*-dimethylhydrazine (—CH$_2$—N(CH$_3$)—N(CH$_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake.

Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMSOJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some cases, the unnatural nucleic acids further form unnatural base pairs. Exemplary unnatural nucleotides capable of forming an unnatural DNA or RNA base pair (UBP) under conditions in vivo includes, but is not limited to, SSICS, dSSICS, NAM, dNaM, and combinations thereof. In some embodiments, unnatural nucleotides include:

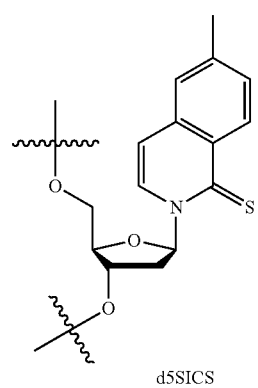

d5SICS

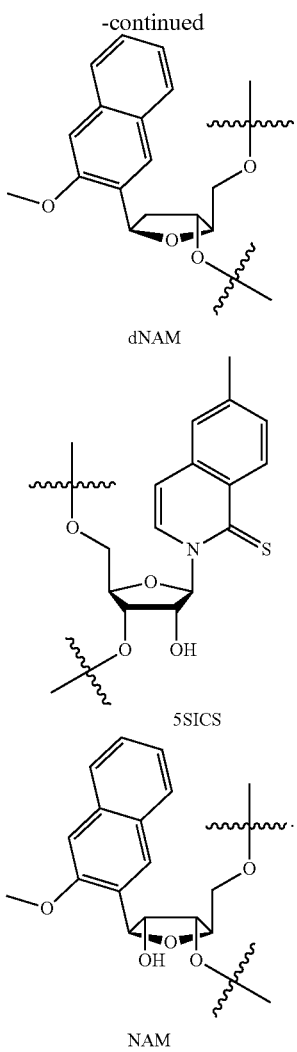

dNAM

5SICS

NAM

In some embodiments, an unnatural base pair generate an unnatural amino acid described in Dumas et al., "Designing logical codon reassignment—Expanding the chemistry in biology," *Chemical Science*, 6: 50-69 (2015).

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s).

The orthogonal tRNA synthetase/tRNA pair charges a tRNA with an unnatural amino acid and incorporates the unnatural amino acid into the polypeptide chain in response to the codon. Exemplary aaRS-tRNA pairs include, but are not limited to, Methanococcus jannaschii (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs.

A cytokine (e.g., IL-2) polypeptide comprising an unnatural amino acid(s) are prepared by introducing the nucleic acid constructs described herein comprising the tRNA and tRNA synthetase and comprising a nucleic acid sequence of interest with one or more in-frame orthogonal (stop) codons into a host cell. The host cell is exposed to a physiological solution comprising the unnatural amino acid(s), and the host cells are then maintained under conditions which permit expression of the protein of interest's encoding sequence. The unnatural amino acid(s) is incorporated into the polypeptide chain in response to the codon. For example, one or more unnatural amino acids are incorporated into the cytokine (e.g., IL-2) polypeptide. Alternatively, two or more unnatural amino acids may be incorporated into the cytokine (e.g., IL-2) polypeptide at two or more sites in the protein.

When multiple unnatural amino acids are to be incorporated into a cytokine (e.g., IL-2) polypeptide, it will be understood that multiple codons will need to be incorporated into the encoding nucleic acid sequence at the desired positions such that the tRNA synthetase/tRNA pairs can direct the incorporation of the unnatural amino acids in response to the codon(s). At least 1, 2, 3, 4, or more codon encoding nucleic acids may be incorporated into the nucleic acid sequence of interest.

When it is desired to incorporate more than one type of unnatural amino acid into the protein of interest into a single protein, a second or further orthogonal tRNA-tRNA synthetase pair may be used to incorporate the second or further unnatural amino acid; suitably said second or further orthogonal tRNA-tRNA synthetase pair recognizes a different codon in the nucleic acid encoding the protein of interest so that the two or more unnatural amino acids can be specifically incorporated into different defined sites in the protein in a single manufacturing step. In certain embodiments, two or more orthogonal tRNA-tRNA synthetase pairs may therefore be used.

Once the cytokine (e.g., IL-2) polypeptide incorporating the unnatural amino acid(s) has been produced in the host cell it can be extracted therefrom by a variety of techniques known in the art, including enzymatic, chemical and/or osmotic lysis and physical disruption. The cytokine (e.g., IL-2) polypeptide can be purified by standard techniques known in the art such as preparative chromatography, affinity purification or any other suitable technique.

Suitable host cells may include bacterial cells (e.g., *E. coli*), but most suitably host cells are eukaryotic cells, for example insect cells (e.g. *Drosophila* such as *Drosophila melanogaster*), yeast cells, nematodes (e.g. *Celegans*), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers may be carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

Pharmaceutical Compositions and Formulations

In some embodiments, the pharmaceutical composition and formulations described herein are administered to a subject by multiple administration routes, including but not limited to, parenteral, oral, buccal, rectal, sublingual, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intratechal administration. In some instances, the pharmaceutical composition is formulated for local administration. In other instances, the pharmaceutical composition is formulated for systemic administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pennsylvania 1975, Liberman, H. A. and Lachman, L., Eds., *Pharmaceutical Dosage Forms*, Marcel Decker, New York, N.Y., 1980, and *Pharmaceutical Dosage Forms and Drug Delivery Systems*, Seventh Ed. (Lippincott Williams & Wilkins 1999).

In some cases, the pharmaceutical composition is formulated as an immunoliposome, which comprises a plurality of IL-2 conjugates bound either directly or indirectly to lipid bilayer of liposomes. Exemplary lipids include, but are not limited to, fatty acids; phospholipids; sterols such as cholesterols; sphingolipids such as sphingomyelin; glycosphingolipids such as gangliosides, globocides, and cerebrosides; surfactant amines such as stearyl, oleyl, and linoleyl amines. In some instances, the lipid comprises a cationic lipid. In some instances, the lipid comprises a phospholipid. Exemplary phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, CabOSil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more of the cytokine (e.g., IL-2) polypeptides or cytokine (e.g., IL-2) conjugates disclosed herein, and optionally one or more pharmaceutical excipients described herein to facilitate the delivery of cytokine (e.g., IL-2) polypeptides or cytokine (e.g., IL-2) conjugates. Such kits further optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error, such as for example, within 15%, 10%, or 5%.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "significant" or "significantly" in reference to binding affinity means a change in the binding affinity of the cytokine (e.g., IL-2 polypeptide) sufficient to impact binding of the cytokine (e.g., IL-2 polypeptide) to a target receptor. In some instances, the term refers to a change of at least 10%, 20%, 30%, 40%, 50%, 60%, 70%, 80%, 90%, 95%, or more. In some instances, the term means a change of at least 2-fold, 3-fold, 4-fold, 5-fold, 6-fold, 7-fold, 8-fold, 9-fold, 10-fold, 50-fold, 100-fold, 500-fold, 1000-fold, or more.

In some instances, the term "significant" or "significantly" in reference to activation of one or more cell populations via a cytokine signaling complex means a change sufficient to activate the cell population. In some cases, the change to activate the cell population is measured as a receptor signaling potency. In such cases, an EC50 value may be provided. In other cases, an ED50 value may be provided. In additional cases, a concentration or dosage of the cytokine may be provided.

As used herein, the term "potency" refers to the amount of a cytokine (e.g., IL-2 polypeptide) required to produce a target effect. In some instances, the term "potency" refers to the amount of cytokine (e.g., IL-2 polypeptide) required to activate a target cytokine receptor (e.g., IL-2 receptor). In other instances, the term "potency" refers to the amount of cytokine (e.g., IL-2 polypeptide) required to activate a target cell population. In some cases, potency is measured as ED50 (Effective Dose 50), or the dose required to produce 50% of a maximal effect. In other cases, potency is measured as EC50 (Effective Concentration 50), or the dose required to produce the target effect in 50% of the population.

EXAMPLES

These examples are provided for illustrative purposes only and not to limit the scope of the claims provided herein.

Example 1

Kinase and Cytokine Receptor Dimerization Assays

Cell Handling

PathHunter cell lines were expanded from freezer stocks according to standard procedures. Cells were seeded in a total volume of 204 into white walled, 384-well microplates and incubated for the appropriate time prior to testing.

Agonist Format

For agonist determination, cells were incubated with sample to induce response. Intermediate dilution of sample stocks was performed to generate 5× sample in assay buffer. About 5 µL of 5× sample was added to cells and incubated at 37° C. for 6 to 16 hours depending on the assay. Vehicle concentration was 1%.

Signal Detection

Assay signal was generated through a single addition of 12.5 or 15 µL (50% v/v) of PathHunter Detection reagent cocktail for agonist and antagonist assays respectively, followed by a one hour incubation at room temperature. For some assays, activity was detected using a high sensitivity detection reagent (PathHunter Flash Kit) to improve assay performance. In these assays, an equal volume of detection reagent (25 or 30 uL) was added to the wells, followed by a one hour incubation at room temperature. Microplates were read following signal generation with a PerkinElmer Envision™ instrument for chemilumine-scent signal detection.

Data Analysis

Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX RLU control ligand−mean RLU of vehicle control).

For antagonist mode assays, percentage inhibition was calculated using the following formula:

% Inhibition=100%×(1−(mean RLU of test sample−mean RLU of vehicle control)/(mean RLU of EC80 control−mean RLU of vehicle control)).

Example 2

Cell-Based Screening for Identification of Pegylated IL-2 Compounds with No IL-2Rα Engagement Structural data of the IL-2/heterotrimeric receptor signaling complex (PDB: 2ERJ) were used to guide design of nAA-pegylation sites to specifically abrogate the interaction of IL-2 and IL-2 receptor α subunit (IL-2Rα). Exemplary IL-2 conjugates were subjected to functional analysis: K35, F42, K43, E62, and P65. The IL-2 conjugates were expressed as inclusion bodies in *E. coli*, purified and refolded using standard procedures before site-specifically pegylating the IL-2 product using DBCO-mediated copper-free click chemistry to attach stable, covalent mPEG moieties to the AzK.

The IL-2 conjugates were screened for functional activity at Discoverx (Fremont CA) using the PathHunter IL-2 Cytokine Receptor assay. This assay uses recombinant human U2OS cell line that expresses the IL-2 receptor β (IL-2Rβ) and γ (IL-2Rγ) subunits, each fused to half of the split reporter enzyme β-galactosidase. A second cell line has been further engineered to express the IL-2Rα subunit. Parallel testing with these two cell lines allows assessment of variant activation of the IL-2 receptor αβγ as well as the basal βγ complex. IL-2 agonist activity on the IL-2 βγ receptor complex stimulates receptor dimerization and reporter O-galactosidase reconstitution that results in a chemiluminescent signal. The assay was run in agonist mode to determine the $EC_{50}$ of each test article, and comparison of dose-response curve profiles between IL2Rα positive and negative cell types allows determination of the contribution of IL2Rα to the observed activity.

Table 1 shows the EC50 data for IL-2 receptor agonism in cell-based screen for 30kD PEGylated IL-2 conjugates.

| Site | βγ EC50 (nM) | αβγ EC50 (nM) | βγ/αβγ ratio |
|---|---|---|---|
| Native | 1.68 | 0.074 | 23 |
| K35 | 6.75 | 0.15 | 45 |
| F42 | 6.09 | 0.515 | 12 |
| K43 | 9.84 | 0.131 | 75 |
| E62 | 3 | 1.5 | 2 |
| P65 | 23.8 | 4.44 | 5 |

Biochemical Interactions of PEGylated IL-2 with Human IL-2 Receptor Subunits

The kinetics of PEGylated IL-2 compound interactions with human IL-2 receptor subunits were measured using Surface Plasmon Resonance (SPR) at Biosensor Tools LLC (Salt Lake City, UT). For these studies, human IgG1 Fc-fused IL-2 Rα (Sino Biological #10165-H02H) and β (Sino Biological #10696-H02H) extracellular domains were captured on the surface of a Biacore Protein A-coated CM4 sensor chip. These surfaces were probed in duplicate, with two-fold dilution series starting at 2 μM of either native IL-2 (wild-type IL-2; Thermo #PHC0021), P65_30kD, P65_5kD, E62_30kD, or E62_5kD using a Biacore 2000 SPR instrument. Test samples were injected for 60 s to allow measurement of association, followed by buffer only (wash) for 30 s to measure dissociation. Response units (RU, Y-axis) are plotted versus time (s, X-axis).

To evaluate the effect of IL-2 receptor α subunit on IL-2 binding to β, α was captured in about two-fold excess relative to β. To these surfaces, native IL-2 (wild-type IL-2), P65_30kD, P65_5kD, E62_30kD, or E62_5kD were applied in a three-fold dilution series beginning at 2.5 μM. The binding data were fit to a 1:1 interaction model that included a bulk shift, and the extracted kinetic parameters are summarized in Table 2A and Table 2B.

TABLE 2A

Kinetic parameters for IL-2 variant interactions with individual IL-2 receptor subunit surfaces - IL-2 receptor α surface

| | $k_a$ ($M^{-1}s^{-1}$) | $k_d$ ($s^{-1}$) | $K_D$ (μM) |
|---|---|---|---|
| IL-2 native | 4.5 ± 0.3 × $10^7$ | 0.410 ± 0.01 | 0.009 ± 0.002 |
| P65_30kD | 114 ± 36 | 0.018 ± 0.008 | 158 ± 21 |
| P65_5kD | 797 ± 226 | 0.033 ± 0.004 | 42 ± 7 |
| E62_30kD | 333 ± 88 | 0.050 ± 0.01 | 162 ± 7 |
| E62_5kD | 1010 ± 41 | 0.035 ± 0.002 | 34.4 ± 0.3 |

TABLE 2B

Kinetic parameters for IL-2 variant interactions with individual IL-2 receptor subunit surfaces - IL-2 receptor β surface

| | $k_a$ ($M^{-1}s^{-1}$) | $k_d$ ($s^{-1}$) | $K_D$ (μM) |
|---|---|---|---|
| IL-2 native | 1.3 ± 0.2 × $10^6$ | 0.185 ± 0.009 | 0.145 ± 0.005 |
| P65_30kD | 1.8 ± 0.2 × $10^5$ | 0.370 ± 0.01 | 2.09 ± 0.09 |
| P65_5kD | 9.0 ± 0.4 × $10^5$ | 0.270 ± 0.01 | 0.305 ± 0.002 |
| E62_30kD | 1.8 ± 0.4 × $10^5$ | 0.208 ± 0.006 | 1.14 ± 0.01 |
| E62_5kD | 6.6 ± 0.8 × $10^5$ | 0.281 ± 0.004 | 0.428 ± 0.00 |

On sensor surfaces containing immobilized IL-2Rα, native IL-2 showed rapid association and slow dissociation kinetics, demonstrating high-affinity binding (FIG. 4A). In contrast, neither P65_30kD or E62_30kD interact with the IL-2Rα surface even at the highest test concentration of 2 μM (FIG. 4A). Surfaces containing immobilized IL-2 Rβ showed comparable association and dissociation responses with both native IL-2 (wild-type IL-2) and IL-2 P65_30kD (FIG. 4B). The modest difference in $K_D$ observed between compounds for the β subunit is due to the decreased on-rate of IL-2 P65_30kD relative to native IL-2, expected from the change in the hydrodynamic radius of this pegylated compound (lower diffusion coefficient) as well as non-specific shielding effects of the large PEG moiety on distant binding surfaces. These results suggest that P65_30kD and E62_30kD are defective in IL-2Rα interactions while largely retaining binding to IL-2Rβ.

Ex-Vivo Immune Response Profiling of IL-2 P65_30kD and E62_kD in Primary Human Leukocyte Reduction System (LRS)-Derived PBMC Samples To determine how the differential receptor specificity of IL-2 P65_30kD and E62_30kD effects activation of primary immune cell subpopulations, concentration-response profiling of lymphocyte activation in human LRS-derived peripheral blood mononuclear cell (PBMC) samples were performed using multi-color flow cytometry. These studies were performed at PrimityBio LLC (Fremont, CA). Fresh LRS-derived samples were treated with either native IL-2, P65_30kD, or E62_30kD in 5-fold dilution series starting with a top concentration of 30 μg/mL. After a 45 min incubation, samples were fixed and stained with antibodies to detect the phosphorylated form of the transcription factor STAT5 (pSTAT5), a marker of upstream engagement and activation of IL-2 receptor signaling complexes, and a panel of surface markers (Table 3) to follow pSTAT5 formation in specific Tcell and natural killer (NK) cell subpopulations.

TABLE 3

Staining panel for flow cytometry study of LRS-derived PBMC samples

| Cell type | marker profile |
|---|---|
| Effector T cells (Teff) | CD3+, CD4+, CD8+, CD127+ |
| NK cells | CD3−, CD16+ |
| Regulatory T cells (Treg) | CD3+, CD4+, CD8−, IL-2Rα+, CD127− |

Figure 5A:
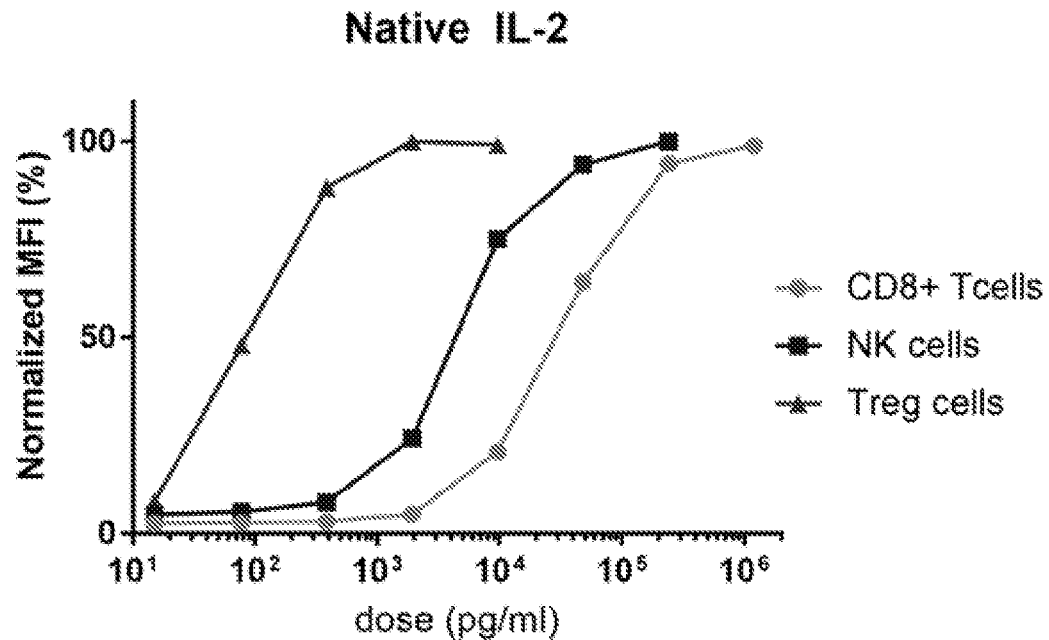
Figure 5B:
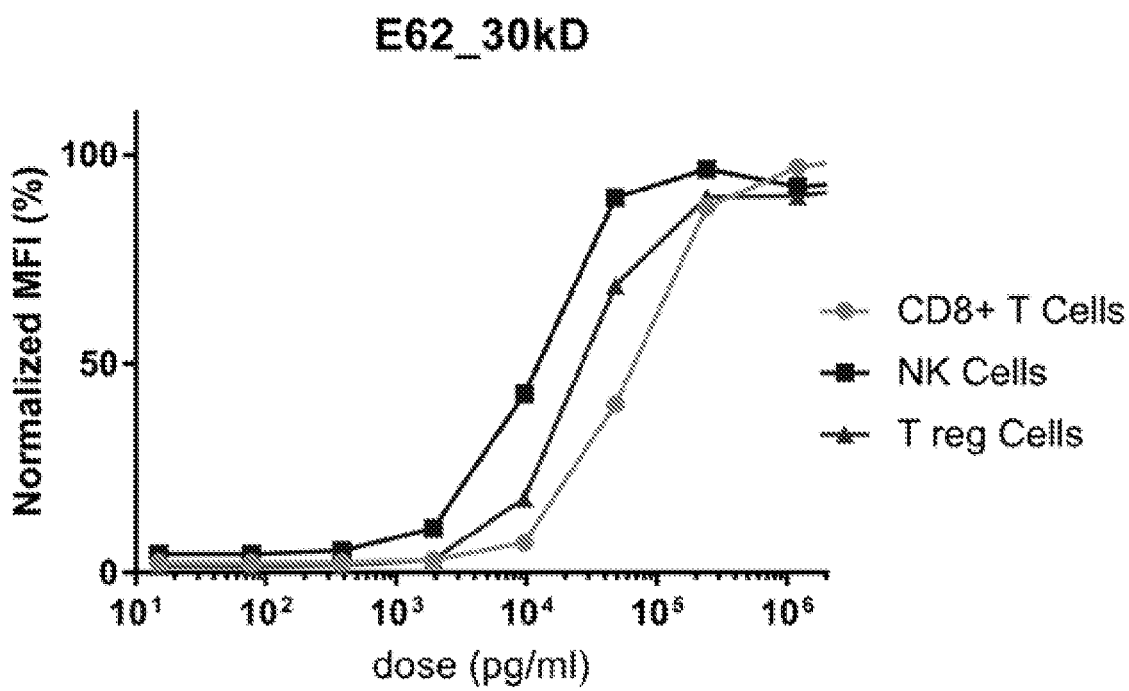
Figure 5C:
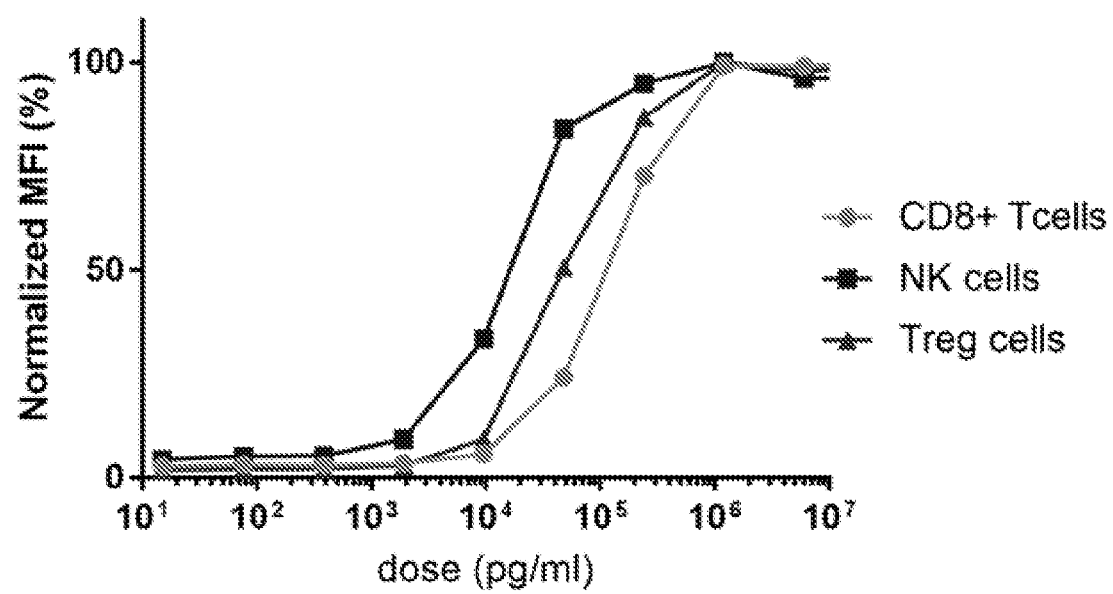

Flow cytometry data were analyzed for activation of different T and NK cell subsets in concentration-response mode, reading pSTAT5 accumulation after treatment with native IL-2 (FIG. 5A), E62_30kD (FIG. 5B), and P65_30kD (FIG. 5C). In NK and effector T cell (CD3+CD8+) populations, IL-2 P65_30kD and IL-2 E62_30kD retained potency relative to the native IL-2, with $EC_{50}$ values for pSTAT5 production within 4-5 fold of the native IL-2 (FIG. 5A). In contrast, the $EC_{50}$ values for pSTAT5 induction for IL-2 P65_30kD in the Treg subpopulation (CD3+CD4+IL-2Rα+ CD127−) was reduced by 900-fold compared to the native IL-2, yet remained similar to the $EC_{50}$ for NK and Teff cell populations (FIG. 5C). This substantial increase in $EC_{50}$ for IL-2 P65_30kD specifically in the Treg population indicates that pegylation of IL-2 at these positions allows agonism of IL-2 receptors, yet eliminates the bias of IL-2 for Treg stimulation relative to effector T cells.

TABLE 4

Dose response EC50 for pSTAT5 signaling (EC50) in human LRS samples or CTLL-2 proliferation treated with indicated IL-2 variant

| treatment | NK Cells | Treg Cells | CD8+ T Cells | CD8/ Treg ratio | CTLL-2 |
|---|---|---|---|---|---|
| Native IL-2 | 5150.5 | 62.5 | 25703.5 | 411.3 | 846 |
| E62_30kD | 12834 | 37213 | 66644 | 1.8 | 398,012 |
| E62_5kD | 5327.5 | 18146 | 41552.5 | 2.3 | 275,590 |
| E62K | 10305 | 11086 | 64037 | 5.8 | 58,213 |
| P65_30kD | 15741 | 40740.5 | 113638 | 2.8 | 677,198 |
| P65_5kD | 1920 | 6324.5 | 13769.5 | 2.2 | 194,924 |
| K35_30kD | 14021 | 358 | 63023 | 176.0 | N.D. |
| F42_30kD | 16397 | 36856 | 107944 | 2.9 | 123,936 |
| K43_30kD | 9004 | 4797 | 50504 | 10.5 | N.D. |

The EC50 values (pg/mL) was calculated from dose response curves generated from MFI plots.

Example 3

PK/PD Studies in Naïve (E3826-U1704) and B16-F10 Tumor-Bearing(E3826-U1803) C57BL/6 Mice The study designs are summarized in Tables 5 and 6. Terminal blood samples were collected via cardiac puncture at the points indicated. Study E3826-U1704, included 13 time points (0.13, 0.25, 0.5, 1, 2, 4, 8, 12, 24, 48, 72, 96 and 120 h) sacrificing 3 mice per each time point and study E3826-U1803 included 9 time points (2, 8, 12, 24, 48, 72, 120, 168, and 240 h) sacrificing 4-7 mice per each time point. Plasma and blood cells (in both studies) and tumors in study E3826-U1803 were collected for PK and PD analyses.

Bioanalysis of plasma samples was performed using a qualified human IL-2 ELISA assay (Abcam, Cambridge, UK). Concentrations of Aldesleukin, E62_30kD and P65_30kD and the internal standard in samples derived from plasma were determined using an ELISA assay. PK data analysis was performed at NW Solutions (Seattle, WA). The PK data were imported into Phoenix WinNonlin v6.4 (Certara/Pharsight, Princeton, NJ) for analysis. The group mean plasma concentration versus time data were analyzed with noncompartmental methods using an IV bolus administration model.

TABLE 5

PK/PD Study No. E3826-U1704 - Control and Test Treatment groups in Naïve C57/BL6 Mice

| Treatment | Dose*(mg/Kg) | Route, Schedule | Time Points | N |
|---|---|---|---|---|
| Control | 0 | IV, single dose | 13 | 3 |
| Aldesleukin | 0.3 | IV, single dose | 13 | 3 |
| P65_30kD | 0.3 | IV, single dose | 13 | 3 |
| E62_30kD | 0.3 | IV, single dose | 13 | 3 |

*Dose refers to P65_30kD IL-2 polypeptide amount

TABLE 6

PK/PD Study No. E3826-U1803 - Control and Test Treatment groups - B16F-10 Melanoma Tumor-Bearing Mice

| Treatment | Dose (mg/kg) | Route, Schedule | Time Point | N |
|---|---|---|---|---|
| None (pre-dose) | 0 mg/kg | None | 1 | 6 |
| Vehicle Control | 0 mg/kg | IV, single dose | 9 | 3 |
| P65_30kD | 1 mg/kg | IV, single dose | 9 | 4 |
| P65_30kD | 3 mg/kg | IV, single dose | 9 | 4 |

Figure 6:
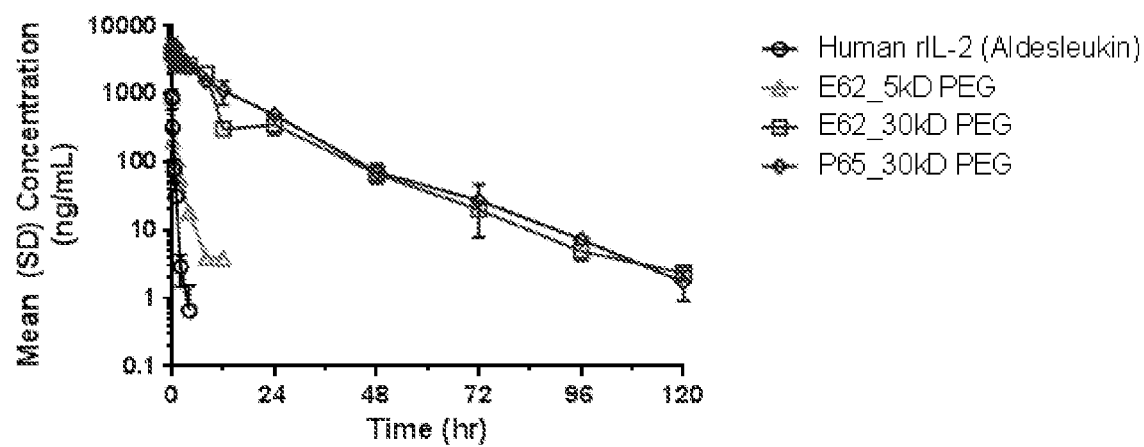
FIG. 6 shows the mean (±SD) plasma concentration versus time profiles following a single IV bolus dose of aldesleukin (IL-2), E62_5, E62_30 and P65_30 to C57BL/6 mice.

The plasma concentration profiles of P65_30kD, E62_30kD, E62_5kD and aldesleukin at 0.3 mg/kg are plotted in FIG. 6.

In study E3826-U1704, both P65_30kD and E62_30kD exhibits a superior PK profile relative to aldesleukin as summarized on Table 3. Following a single IV bolus dose of aldesleukin, the Tmax was observed at 0.03 h post-dose (the first measured timepoint after dosing) and mean plasma concentrations were measurable out to 4 h post-dose. After single IV bolus dosing of P65_30kD and E62_30kD, the Tmax was observed at 0.03 h post-dose and mean plasma concentrations were measurable out to 120 h post-dose (the last measured timepoint). In a separate study, after IV dosing of E62_5kD, the Tmax was observed at 0.133 hr post-dose and mean plasma concentrations were measurable out to 12 hr post-dose.

Exposure based on $C_{max}$ and $AUC_{0-t}$, was as follows: P65_30kD>>E62_30kD>>E62_5kD>aldesleukin.

E62_5kD with a smaller PEG had a PK profile closer to rIL-2. P65_30kD exposure was 5.5 and 200 times higher than aldesleukin based on Cmax and AUC0-t, respectively. In addition, P65_30kD demonstrated 23-fold extended t1/2 (13.3 h vs. 0.57 h) and about 198-fold reduced CL (6.58 vs 1300 mL/h/Kg) compared to the aldesleukin. For both P65_30kD and E62_30kD, the distribution volume (82.4 and 92.3 mL/Kg respectively) was about 4.2 to 4.7-fold reduced relative to aldesleukin, and similar to the blood volume in a mouse (85 mL/Kg; [Boersen 2013]). This suggests that P65_30kD and E62_30kD are mostly distributed within systemic circulation.

TABLE 7

P65_30kD PK Parameters in C57BL/6 Female Mice

| Parameter | Units | P65_30kD | E62_30kD | E62_5kD | Aldesleukin |
|---|---|---|---|---|---|
| $T_{max}$ | h | 0.030 | 0.030 | 0.133 | 0.030 |
| $C_{max}$ | ng/ml | 4,870 | 4,230 | 936 | 884 |
| $AUC_{0-t}$ | h * ng/ml | 45,600 | 37,100 | 798 | 229 |
| $R^2$ | | 0.992 | 0.986 | 0.851 | 0.900 |
| $AUC_{INF}$ | h * ng/ml | 45,600 | 37,100 | 807 | 230 |
| $t_{1/2}$ | h | 13.300 | 14.500 | 2.56 | 0.573 |
| CL | mL/h/Kg | 6.580 | 8.07 | 372 | 1300 |
| $V_{ss}$ | mL/Kg | 82.4 | 92.3 | 404 | 390 |

Note:
$R^2$ is the goodness-of-fit parameter for the terminal phase of each concentration versus time profile
All parameters shown to 3 significant figures.

Example 4

Pharmacodynamic Observations in Peripheral Blood Compartment

Figure 7:
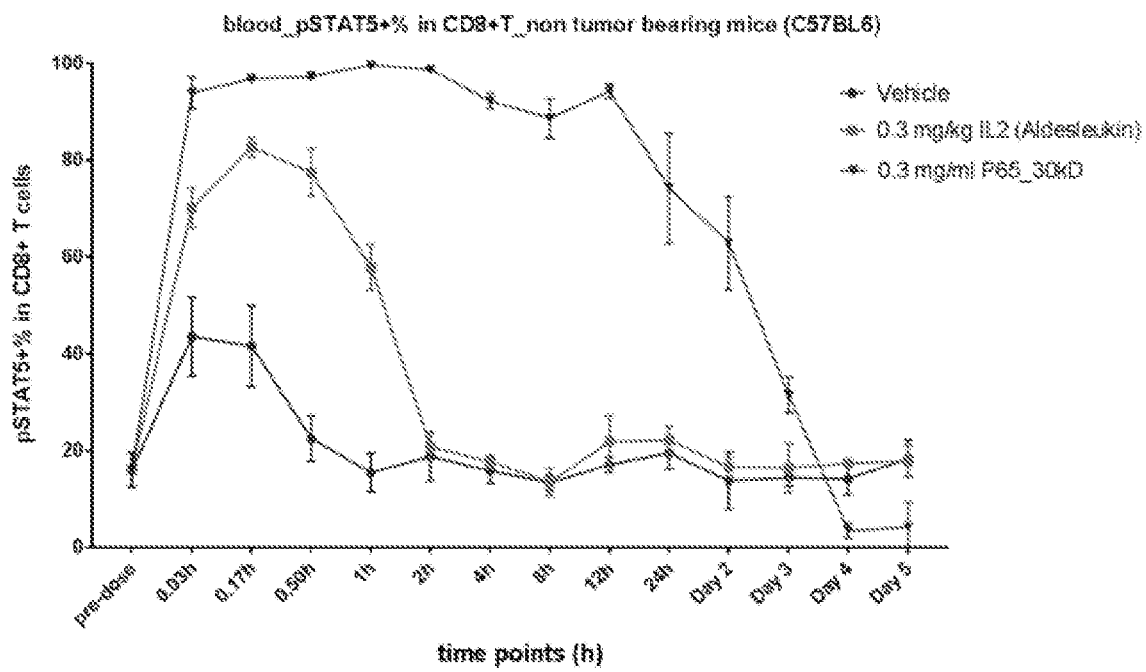
FIG. 7 shows percentage of pSTAT5+ CD8+ T cells vs time cells in peripheral blood following treatment with a single IV bolus dose of P65_30 or aldesleukin to C57BL/6 mice.
Figure 8A:
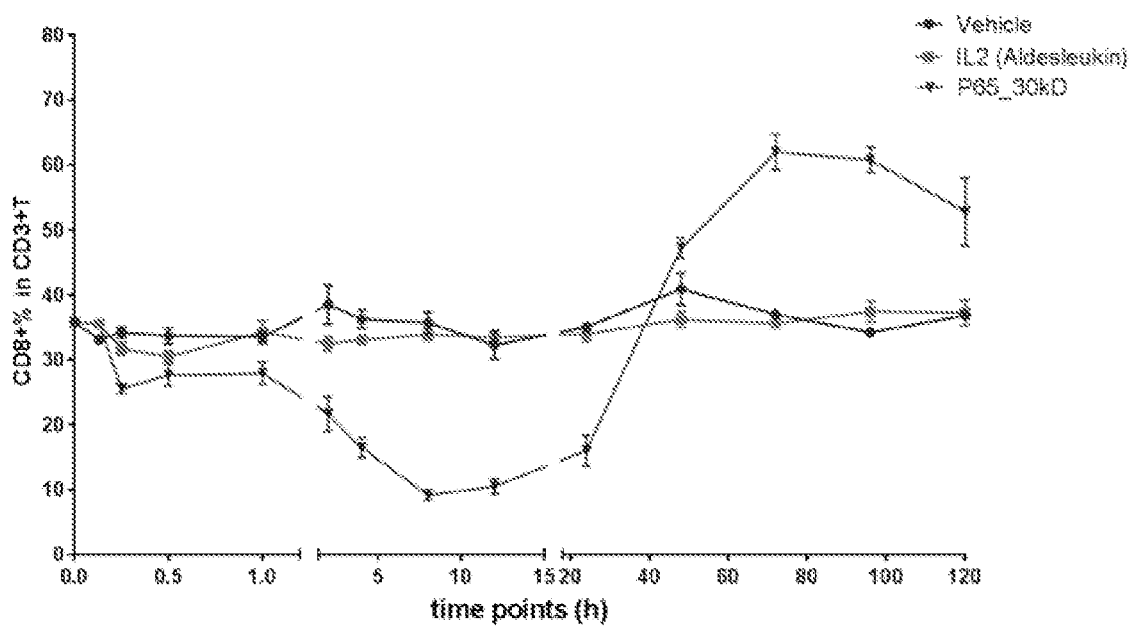
FIG. 8A-FIG. 8C show percentage of CD8+ T cells (FIG. 8A), NK cells (FIG. 8B) and CD4+ Treg cells (FIG. 8C) in the PBMC population following treatment with a single IV bolus dose of P65_30 or aldesleukin (IL-2). Blood was drawn via cardiac puncture at the time points indicated and immune cell populations were assessed by flow cytometry. Each data point represents an average from 3 replicates at each time point, ±SEM.
Figure 8B:
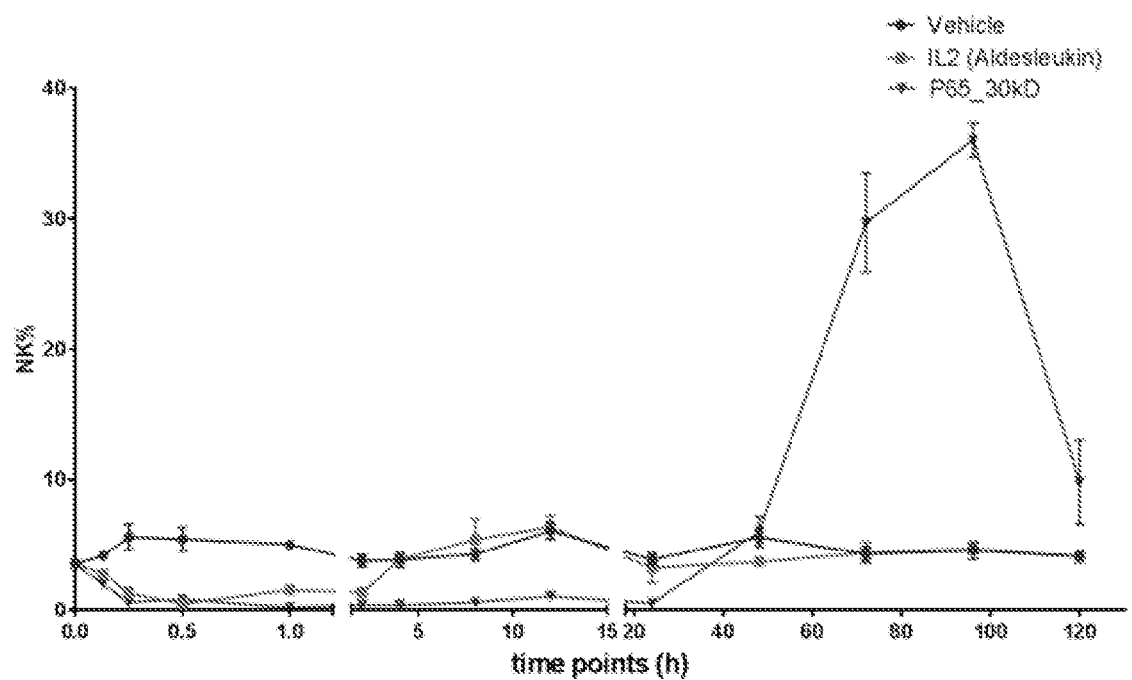
Figure 8C:
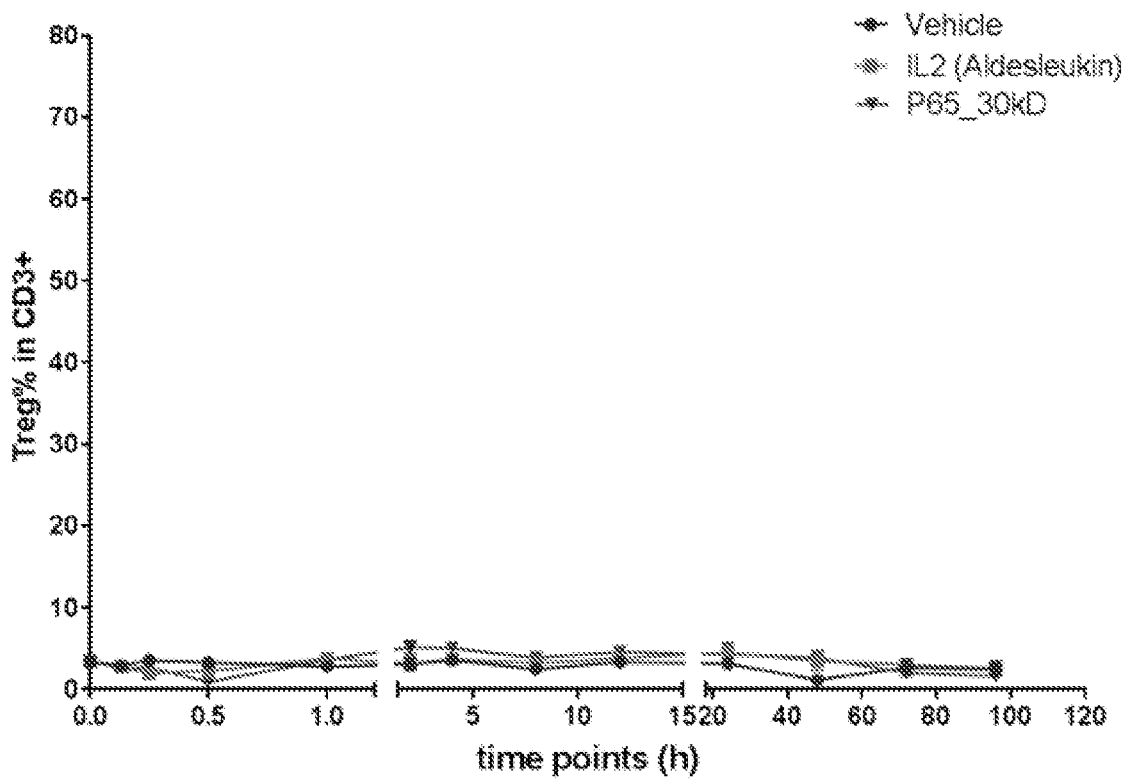
Figure 9A:
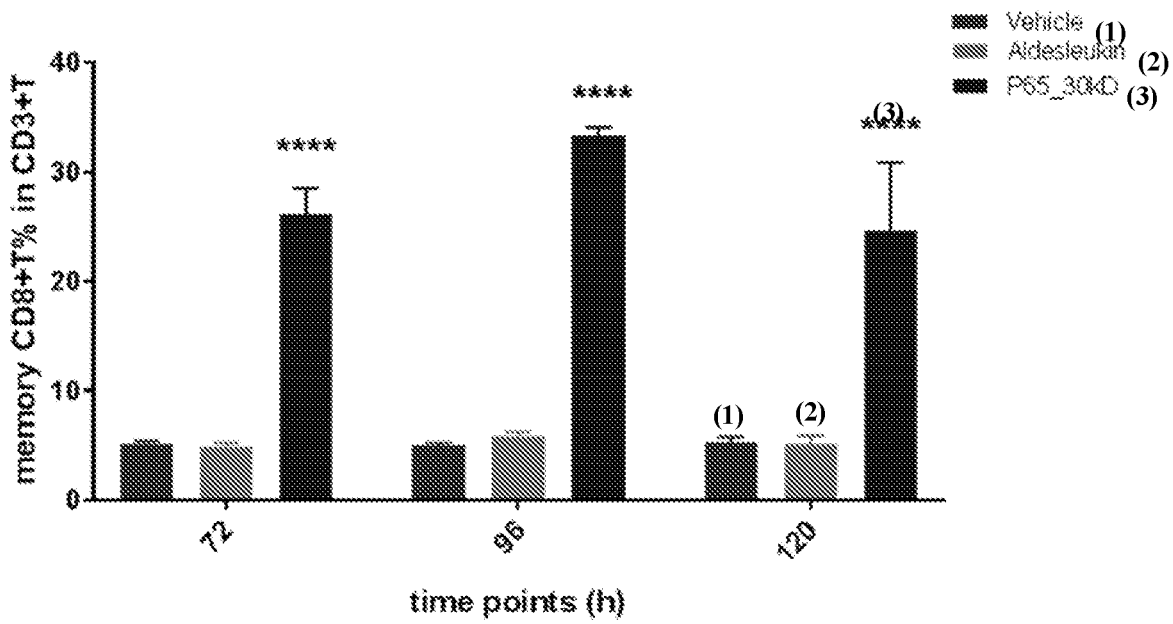
FIG. 9A-FIG. 9B show differences between P65_30 and IL-2 (aldesleukin) in the stimulation of memory CD8+ CD44+ T cell proliferation within the CD3+ population following treatment with a single IV bolus dose of P65_30 or aldesleukin (IL-2). Blood was drawn via cardiac puncture at the time points indicated and immune cell populations were assessed by flow cytometry. Data were analyzed using unpaired Student t test. *** designate P values <0.001.
Figure 9B:
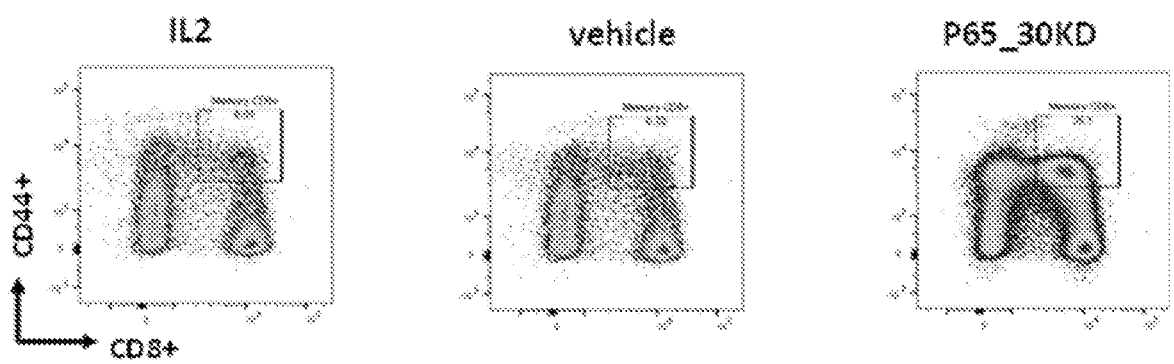

STAT5 phosphorylation and induction of cell proliferation (the early molecular marker Ki-67 and cell counts) was used as pharmacodynamic readouts to assess the pharmacological profile of P65_30kD relative to its pharmacokinetics. The pSTAT5 PD marker showed good correlation with PK for both P65_30kD and aldesleukin in CD8+ effector T cells (Table 7). Persistent elevation of pSTAT5 was observed in both NK and CD8+ T cells up to 72 h, and up to 24 h in Tregs. pSTAT5 induction returned to baseline after only 2 h in mice dosed with aldesleukin (FIG. 7). STAT5 phosphorylation translated into delayed proliferative responses (72-120 hrs) of CD8+ effector T cells and NK cells but not with T regs (FIGS. 8A-8C), Phenotypic analysis of CD8+ effector T cells revealed substantial expansion of CD44+ memory cells within this population (FIGS. 9A-9B).

Pharmacodynamic Observations in Tumor Compartment in Bl6-F10 Tumor-Bearing (E3826-U1803) C57BL/6 Mice Table 8 shows the plasma and tumor drug concentration following a single dose of P65_30kD at 3 mg/kg in Bl6-F10 tumor-bearing mice. The tumor half-life was twice the plasma half-life (24.4 vs 12.6), indicating that the P65_30kD penetrates the tumor and is retained in the tumor. The tail end of the curves cross showing the plasma eliminates faster than the tumor. The tumor:plasma AUC ratio was 9.7% and 8.4% for the 1 and 3 mg/kg doses respectively.

TABLE 8

P65_30kD Plasma and Tumor PK Parameters B16-F10 tumor-bearing C57BL/6 Female Mice

| | P65_30kD (3 mg/kg) | |
|---|---|---|
| Parameter | Plasma | Tumor |
| $T_{max}$ (h) | *2.00 | 8 |
| $C_{max}$ (ng/ml) | 40000 | 1550 |
| t1/2 (h) | 12.60 | 24.4 |
| $AUC_{0-t}$ (h * ng/ml) | 656,000 | 55200 |
| $R^2$ | 0.974 | 0.988 |
| $AUC_{INF}$ (h * ng/ml) | 656,000 | 55200 |

Figure 10A:
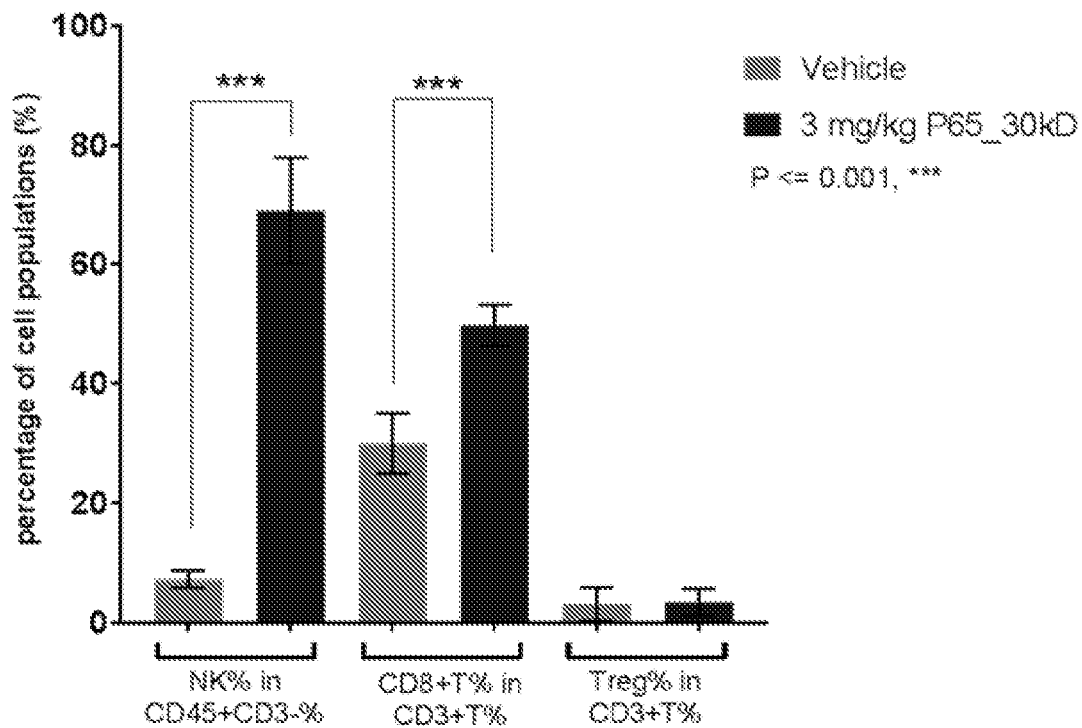
FIG. 10A-FIG. 10B show the increase in tumor-infiltrating lymphocytes (TILs) vs time in C57Bl6 mice bearing syngeneic Bl6F10 tumors following treatment with a single IV bolus dose of P65_30.
Figure 10B:
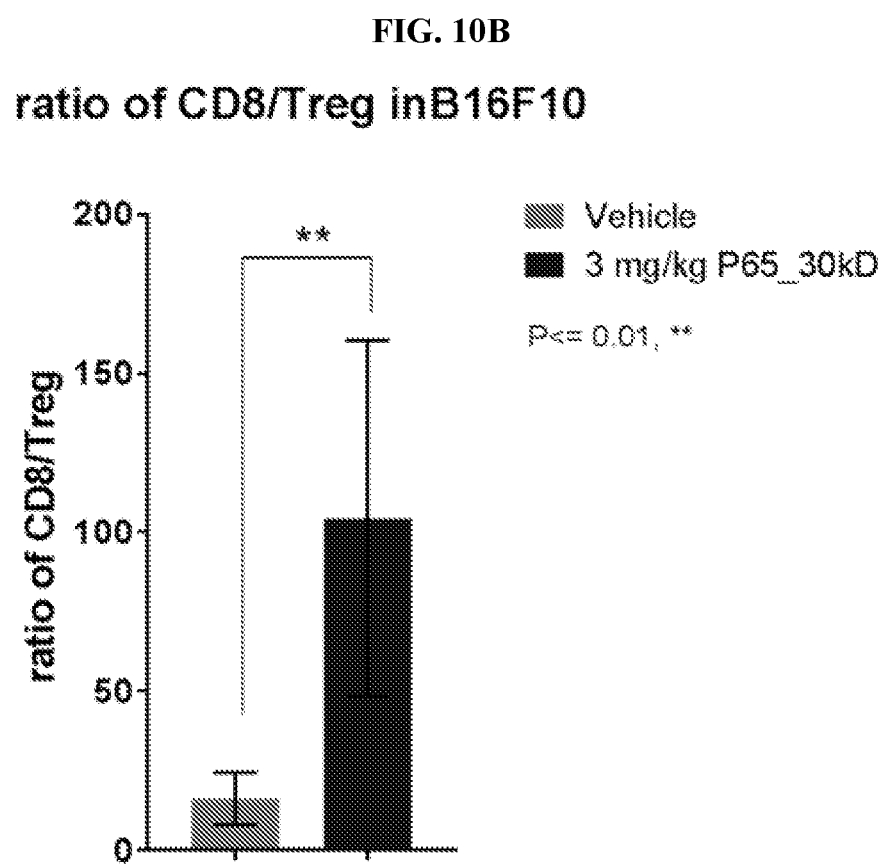

FIG. 10A-FIG. 10B show the expansion of NK and CD+ T cells by P65_30kD in Bl6F10 tumors. FIG. 10A shows of the percentage of NK cells, CD8+ cells and Tregs in the tumor CD3+ T cell population following treatment with a single IV bolus dose of P65_30kD at 3 g/kg. Tumor samples were analyzed for immune cell populations 5 days after treatment by flow cytometry. Each data point represents an average from 3 replicates at each time point, ±SEM. The cell population data represented is from day 5 Tumor samples and the CD8/Treg ratio was calculated from the day 7 samples. FIG. 10B shows the ratio of CD8+ effector over CD4+ regulatory T cells 7 days following treatment with a single IV bolus dose of P65_30kD at 3 mg/kg. Each data point represents an average from 3 replicates at each time point, ±SEM.

MTD Study in Balb/c Mice E3826-U1802

A dose ranging study of P65_30kD was conducted in naïve female Balb/c mice at Crown Biosciences, Inc. (San Diego, CA). The study design is shown in Table 9. Blood samples were drawn via sub mandibular vein at 7 time points (0.25, 1, 4, 12, 24, 34, 48 & 72 h). Both plasma and blood cells were collected for PK and PD analyses.

All plasma samples were analyzed for human IL-2 as well as mouse IL-2, TNF-α, IFNγ, IL-5, and IL-6 cytokines, employing commercially-available ELISA kits.

TABLE 9

PK/PD and MTD Study No. E3826-U1802 - Control and Test Treatment groups in Naïve Balb/C Mice

| Treatment | Dose (mg/kg) | Route, Schedule | Time Point | N |
|---|---|---|---|---|
| Naive | 0 mg/kg | | 0 | 3 |
| Vehicle Control | 0 mg/kg | IV, BID × 3 | 3 | 3 |
| Aldesleukin | 0.01 mg/kg | IV, BID × 3 | 3 | 3 |
| Aldesleukin | 0.03 mg/kg | IV, BID × 3 | 3 | 3 |
| Aldesleukin | 0.1 mg/kg | IV, BID × 3 | 3 | 3 |
| Aldesleukin | 1.0 mg/kg | IV, BID × 3 | 3 | 3 |
| Aldesleukin | 3.0 mg/kg | IV, BID × 3 | 3 | 3 |
| Aldesleukin | 5.0 mg/kg | IV, BID × 3 | 3 | 3 |
| P65_30kD | 0.01 mg/kg | IV, single dose | 3 | 3 |
| P65_30kD | 0.03 mg/kg | IV, single dose | 3 | 3 |
| P65_30kD | 0.1 mg/kg | IV, single dose | 3 | 3 |
| P65_30kD | 1.0 mg/kg | IV, single dose | 3 | 3 |
| P65_30kD | 3.0 mg/kg | IV, single dose | 3 | 3 |
| P65_30kD | 5.0 mg/kg | IV, single dose | 3 | 3 |
| #P65_30kD | 0.3 mg/kg | IV, single dose | 8 | 3 |

Figure 11A:
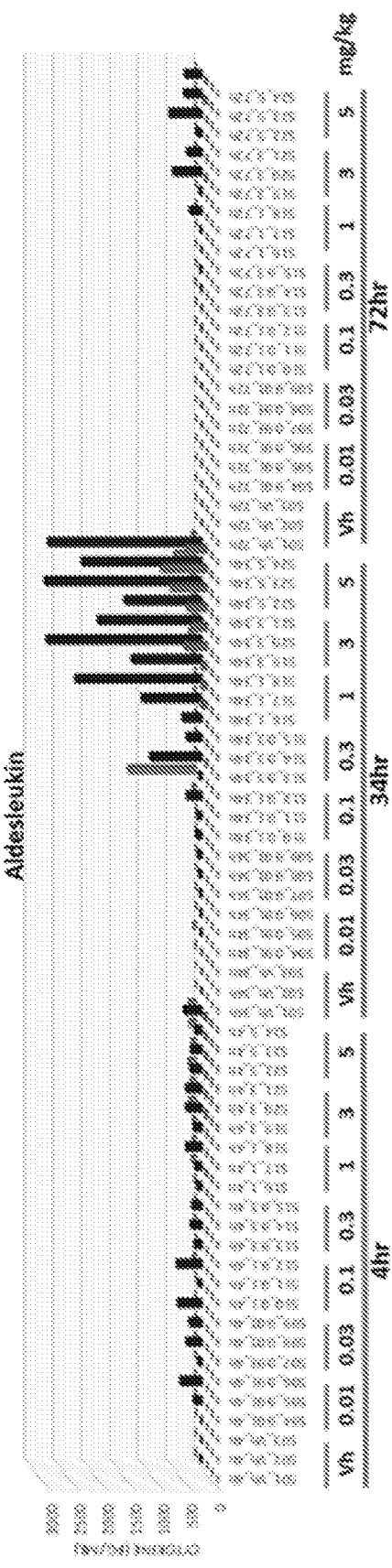
FIG. 11A-FIG. 11B show plasma levels of mouse IL-2, TNF-α, IFNγ, IL-5 and IL-6 following treatment with a single IV bolus dose of P65_30 or aldesleukin (IL-2) at increasing levels (0.01-5 mg/kg). The concentration of each cytokine in plasma was determined via ELISA (Abcam, Cambridge, UK). For each dose group N=3 mice and samples were collected at 4, 34 and 72 h post-dose.
Figure 11B:
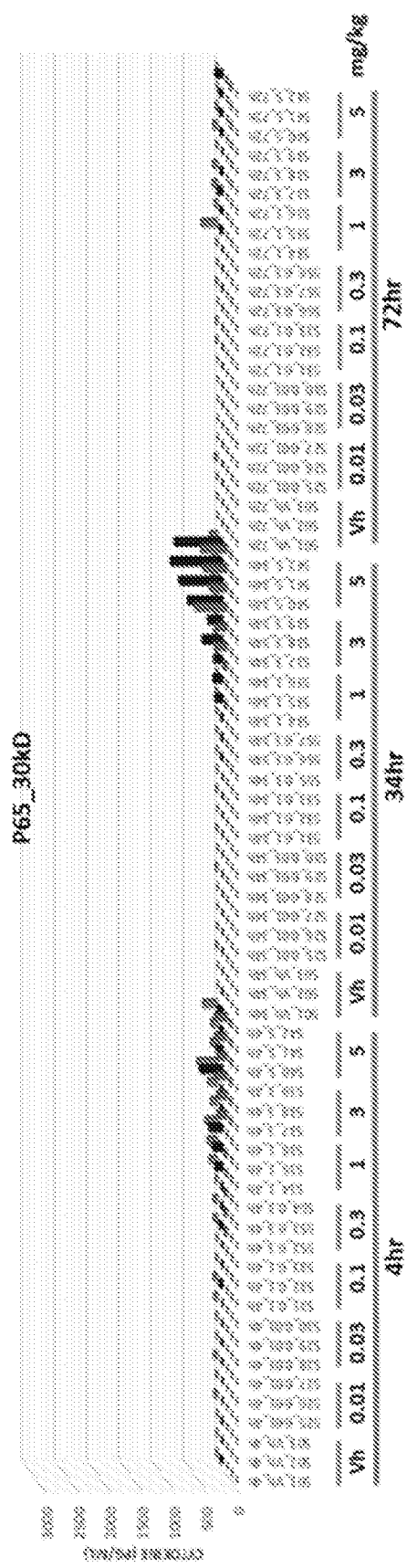

* All time point except the 72 hr time point blood collection was via the sub mandibular vein. The 72 hr time point was terminal blood collection.
Only the 0.3 mg/kg dose of P65_30kD was used for the PKPD evaluation Toxicology Observations in the MTD Study Using Balb/c Mice A major of toxicity associated with High-dose IL-2 is Vascular leak syndrome and associated Cytokine Release Syndrome (CRS). To evaluate this in mice, a single dose IV administration of P65_30kD at doses ranging from 0.01-5.0 mg/kg dose was performed (Table 10). The analysis performed was hematology, histopathology, organ weight, and cytokine analyses. Abnormalities were not observed with hematology, histopathology or body weights relative to the vehicle control mice with both P65_30kD or aldesleukin. With respect to the cytokine analysis, it was observed that aldesleukin elevated plasma IL-5 levels starting at 1 mg/kg to 5 mg/kg (FIG. 11A). With P65_30kD, a moderate increase in IL-5 was seen only at 5 mg/kg dose and this was less compared to aldesleukin (FIG. 11B). A transient elevation in the systemic levels of IFNγ was observed with both aldesleukin and P65_30kD.

Example 5

PK/PD in Cynomolgus Monkeys-Study No.: 20157276

The pharmacokinetic and pharmacodynamic profile of P65_30kD was evaluated in non-naïve cynomolgus monkeys following administration of a single intravenous dose at 0.3 mg/kg. The study was conducted at Charles River Laboratories, Inc. (Reno, NV) and PK data analysis was performed at NW Solutions (Seattle, WA). Blood samples were collected pre-dose and at 21 time points (0.5, 1, 2, 4, 8, 12, 24, 36, 48, 72, 120, 144, 168, 192 and 240 h post-dose. Both plasma and blood cells were collected for PK and PD analyses. Selected time points were used for PK, PD, cell population and hematology analysis.

All plasma samples were analyzed for human IL-2 (PK readout) employing commercially-available ELISA kits.

Table 10 shows P65_30kD PK Parameters in Cynomolgus monkey.

TABLE 10

| | | | 0.3 mg/kg | | |
|---|---|---|---|---|---|
| ROA | Parameter | Units | Animal 2699 | Animal 2705 Estimate | Mean |
| IV | $T_{max}$ | hr | 0.500 | 0.500 | 0.500 |
| | $C_{max}$ | ng/ml | 11000 | 11400 | 11200 |
| | $AUC_{0-t}$ | hr * ng/ml | 121000 | 120000 | 121000 |
| | $t_{1/2}$ | hr | 13.4 | 13.9 | 13.6 |
| CL | | mL/hr/kg | 2.47 | 2.49 | 2.48 |
| $V_{ss}$ | | mL/kg | 29.0 | 32.1 | 30.5 |

After single IV bolus dosing Tmax was observed at 0.5 h post-dose (the first measured timepoint after dosing) and mean plasma concentrations were measurable out to 168 h post-dose (the last measure) The $t_{1/2}$ and AUC for P65_30kD were 13.6 h and 121000 hr*ng/mL respectively.

Hematology Parameters—Cynomolgus Monkeys-Study No.: 20157276

For hematologic parameters the evaluation time points correspond to pre-dose at day −1 and 1, 3, 6, 8, 10, 12, 14, 17, 19, 21 post-dose.

Figure 12:
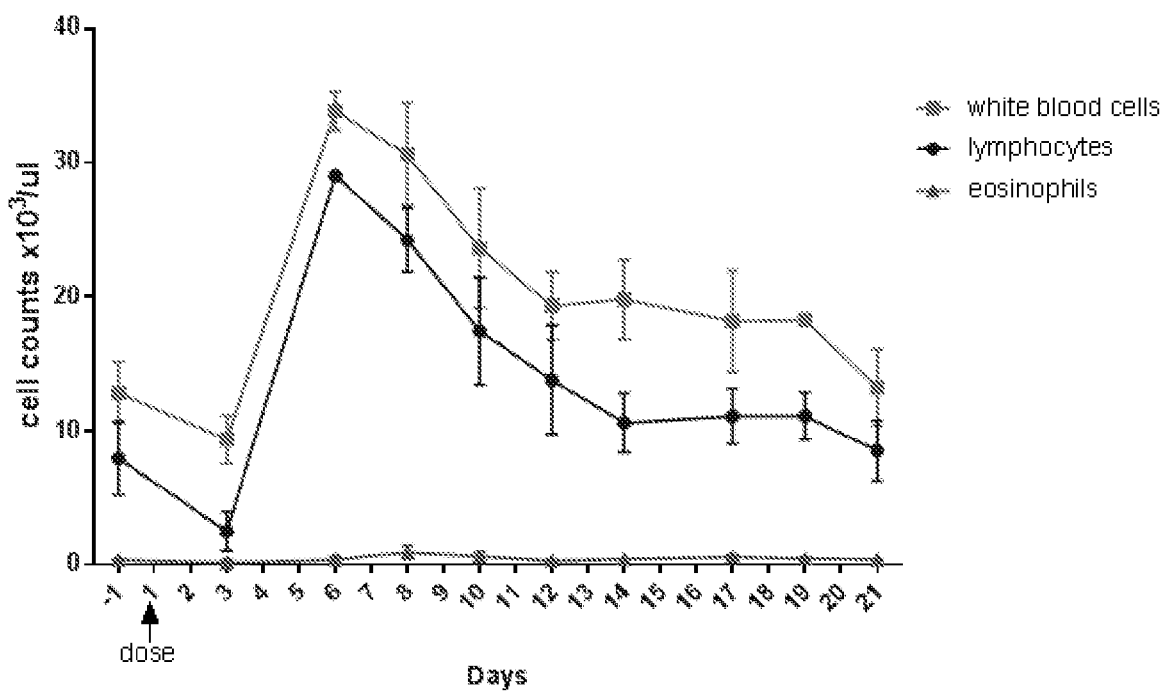
FIG. 12 shows white blood cell, lymphocyte, and eosinophil counts (mean±SD) following a single IV dose of P65_30kD to male Cynomolgus monkeys.

FIG. 12 shows the absolute white blood cell and differential counts. Data represents mean±SD (N=2 animals/dose group).

Analysis of the white blood cell (WBC) subpopulations revealed major increase in WBC count was due an expansion of Lymphocyte cell population which is consistent with the mechanism of P65_30kD. There is no elevation of eosinophils.

Example 6

TABLE 11 illustrates IL-2 sequences described herein.

| Name | Sequence | SEQ ID NO: |
|---|---|---|
| IL-2 (homo sapiens) (mature form) | APTSSSTKKTQLQLEHLLLDLQMILNGINNYKNPKLTRM LTFKFYMPKKATELKHLQCLEEELKPLEEVLNLAQSKNF HLRPRDLISNINVIVLELKGSETTFMCEYADETATIVEFL NRWITFCQSIISTLT | 1 |
| IL-2 (homo sapiens) (precursor) NCBI Accession No.: AAB46883.1 | MYRMQLLSCIALSLALVTNSAPTSSSTKKTQLQLEHLLL DLQMILNGINNYKNPKLTRMLTFKFYMPKKATELKHL QCLEEELKPLEEVLNLAQSKNFHLRPRDLISNINVIVLEL KGSETTFMCEYADETATIVEFLNRWITFCQSIISTLT | 2 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A polynucleic acid molecule encoding a modified interleukin 2 (IL-2) polypeptide, wherein the modified IL-2 polypeptide comprises:

an amino acid sequence that is at least 80% identical to SEQ ID NO: 1, and at least one unnatural amino acid at position K35, T37, R38, T41, F42, K43, F44, Y45, E60, E61, E62, K64, P65, E68, V69, N71, L72, M104, C105, or Y107 in reference to the amino acid positions as set forth in SEQ ID NO: 1, wherein the polynucleic acid molecule comprises a synthetic codon comprising an unnatural nucleotide, and wherein the synthetic codon encodes the at least one unnatural amino acid.

2. The polynucleic acid molecule of claim 1, wherein the unnatural nucleotide is

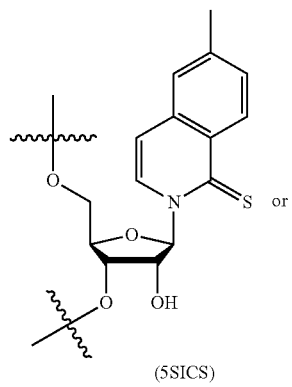

(5SICS)

-continued

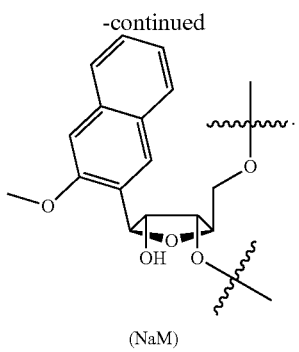

(NaM)

3. The polynucleic acid molecule of claim 1, wherein the polynucleic acid molecule is DNA.

4. The polynucleic acid molecule of claim 1, wherein the modified IL-2 polypeptide comprises at least 90% sequence identity to SEQ ID NO: 1.

5. The polynucleic acid molecule of claim 1, wherein the modified IL-2 polypeptide comprises at least 95% sequence identity to SEQ ID NO: 1.

6. The polynucleic acid molecule of claim 1, wherein the modified IL-2 polypeptide comprises at least 97% sequence identity to SEQ ID NO: 1.

7. The polynucleic acid molecule of claim 1, wherein the position is F42, K43, F44, E62, or P65.

8. The polynucleic acid molecule of claim 7, wherein the position is P65.

9. The polynucleic acid molecule of claim 1, wherein the amino acid sequence that is at least 80% identical to SEQ ID NO: 1 N-terminal deletion comprising a deletion of the first 1, 2, 3, 4, or 5 residues from the N-terminus, wherein the residue positions are in reference to the amino acid positions as set forth in SEQ ID NO: 1.

10. A vector comprising the polynucleic acid molecule of claim 1.

11. A host cell comprising the vector of claim 10.

12. The host cell of claim 11, which is configured to produce the modified IL-2 polypeptide comprising the at least one unnatural amino acid.

13. The host cell of claim 12, wherein the at least one unnatural amino acid is a lysine analogue or comprises an aromatic side chain.

14. The host cell of claim 13, wherein the at least one unnatural amino acid comprises p-acetyl-L-phenylalanine, p-azidomethyl-L-phenylalanine (pAMF), p-iodo-L-phenylalanine, m-acetylphenylalanine, p-propargyloxyphenylalanine, p-propargyl-phenylalanine, 3-methyl-phenylalanine, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, O-allyltyrosine, O-methyl-L-tyrosine, O-4-allyl-L-tyrosine, 4-propyl-L-tyrosine, phosphonotyrosine, L-3-(2-naphthyl) alanine, 2-amino-3-((2-((3-(benzyloxy)-3-oxopropyl)amino)ethyl) selanyl) propanoic acid, or 2-amino-3-(phenylselanyl) propanoic acid.

15. The host cell of claim 11, which is a prokaryotic cell.

16. The host cell of claim 15, wherein the prokaryotic cell is an *E. coli* cell.

17. A method of making an interleukin 2 (IL-2) conjugate, comprising:

reacting an IL-2 polypeptide comprising an unnatural amino acid comprising an azido group, wherein the IL-2 polypeptide comprises at least 80% sequence identity to SEQ ID NO: 1 in which at least one amino acid residue is replaced by the unnatural amino acid, and wherein the at least one amino acid residue is at position K35, T37, R38, T41, F42, K43, F44, Y45, E60, E61, E62, K64, P65, E68, V69, N71, L72, M104, C105, or Y107 in reference to the amino acid positions as set forth in SEQ ID NO: 1, with a conjugating moiety comprising an alkyne group such that the azido group and the alkyne group react together to form a covalent bond, thereby producing the IL-2 conjugate.

18. The method of claim 17, wherein:

the IL-2 polypeptide comprises at least 90% sequence identity to SEQ ID NO: 1 in which the at least one unnatural amino acid residue at position F42, K43, F44, E62, or P65 is replaced by the unnatural amino acid, and the conjugating moiety comprises a water-soluble polymer that comprises the alkyne group.

19. An interleukin 2 (IL-2) conjugate comprising an IL-2 polypeptide that comprises an unnatural amino acid covalently attached to a conjugating moiety, wherein the unnatural amino acid is located at an amino acid residue position in region 35-107, such that the IL-2 conjugate is characterized in that it reduces binding between the IL-2 conjugate and interleukin 2 receptor α (IL-2Rα) but retains significant binding with interleukin 2 By receptor (IL-2Rβγ) signaling complex to form an IL-2/IL-2Rβγ complex, wherein the reduced binding to IL-2Rα is compared to binding between a wild-type IL-2 polypeptide and IL-2Rα, wherein the region 35-107 corresponds to residues K35-Y107 of SEQ ID NO: 1.

20. A method of expressing a modified interleukin 2 (IL-2) polypeptide, comprising culturing the host cell of claim 11 under conditions which permit expression of the encoding sequence of the modified IL-2 polypeptide.

21. The host cell of claim 12, wherein the at least one unnatural amino acid comprises an azido group.

* * * * *

SEQUENCE LISTING

```
Sequence total quantity: 5
SEQ ID NO: 1             moltype = AA  length = 133
FEATURE                  Location/Qualifiers
source                   1..133
                         mol_type = protein
                         organism = Homo sapiens
```

```
SEQUENCE: 1
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 2              moltype = AA  length = 153
FEATURE                   Location/Qualifiers
source                    1..153
                          mol_type = protein
                          organism = Homo sapiens
SEQUENCE: 2
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 3              moltype = AA  length = 5
FEATURE                   Location/Qualifiers
REGION                    1..5
                          note = Synthetic peptide
source                    1..5
                          mol_type = protein
                          organism = synthetic construct
SEQUENCE: 3
GGGGS                                                                5

SEQ ID NO: 4              moltype = AA  length = 5
FEATURE                   Location/Qualifiers
REGION                    1..5
                          note = Synthetic peptide
VARIANT                   4
                          note = Any amino acid except proline
source                    1..5
                          mol_type = protein
                          organism = synthetic construct
SEQUENCE: 4
VPGXG                                                                5

SEQ ID NO: 5              moltype = AA  length = 30
FEATURE                   Location/Qualifiers
REGION                    1..30
                          note = Synthetic polypeptide
source                    1..30
                          mol_type = protein
                          organism = synthetic construct
SEQUENCE: 5
FQSSSSKAPP PSLPSPSRLP GPSDTPILPQ                                    30
```